US008067540B2

(12) United States Patent
Kurochkin et al.

(10) Patent No.: US 8,067,540 B2
(45) Date of Patent: Nov. 29, 2011

(54) HUMAN ALEX1 PROTEINS

(75) Inventors: Igor V. Kurochkin, Ibaraki (JP); Natsumi Yonemitsu, Ibaraki (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 0 days.

(21) Appl. No.: 12/706,647

(22) Filed: Feb. 16, 2010

(65) Prior Publication Data
US 2010/0210818 A1 Aug. 19, 2010

Related U.S. Application Data

(62) Division of application No. 10/204,751, filed as application No. PCT/JP01/01373 on Feb. 23, 2001, now Pat. No. 7,691,992.

(30) Foreign Application Priority Data

Feb. 25, 2000 (JP) ................................. 2000-54466

(51) Int. Cl.
C07K 14/00 (2006.01)
(52) U.S. Cl. ........................................................ 530/350
(58) Field of Classification Search ........................ None
See application file for complete search history.

(56) References Cited

U.S. PATENT DOCUMENTS

| 6,783,961 | B1 | 8/2004 | Edwards et al. |
| 2003/0165831 | A1 | 9/2003 | Lee et al. |

FOREIGN PATENT DOCUMENTS

| JP | 2002-017375 | 1/2002 |
| WO | WO-95/14772 | 6/1995 |
| WO | WO-99/53051 | 10/1999 |

OTHER PUBLICATIONS

Whitmarsh et al. A mammalian scaffold complex that selectively mediates MAP kinase activation. Science. Sep. 11, 1998;281(5383):1671-4.*
Alberts et al., (eds.), Molecular Biology of the Cell, 2nd edition, Garland Publishing, Inc., New York & London (1989).
Alberts et al., Molecular Biology of the Cell, p. G-12 (1994).
Behrens, J. et al., "Functional Interaction of β-Catenin with the Transcription Factor LEF-1" Nature 382:638-642 (1996).
Hatzfeld, M., "The Armadillo Family of Structural Poteins" Int. Rev. Cytol. 186:179-224 (1999).
Kinch, M.S. et al., "Tyrosine Phosphorylation Regulates the Adhesion of Ras-Transformed Breast Epithelia" J. Cell Biol. 130:461-471 (1995).
Kinzler, K.W. and Vogelstein, B., "Lessons from Hereditary Colorectal Cancer" Cell 87:159-170 (1996).
Kurochkin, I.V. et al., "ALEX1, A Novel Human Armadillo Repeat Protein that is Expressed Differentially in Normal Tissues and Carcinomas" Biochem. Biophys. Res. Commun. 280(1):340-347 (2001).
Kurochkin, I.V. and Goto, S., "Alzheimer's β-Amyloid Peptide Specifically Interacts with and is Degraded by Insulin Degrading Enzyme" FEBS Lett. 345:33-37 (1994).
Marshall, Science 269:1050-1055 (1995).
McDermott, J.R. and Gibson, A.M., "Degradation of Alzheimer's β-Amyloid Protein by Human and Rat Brain Peptidases: Involvement of Insulin-Degrading Enzyme" Neurochem. Res. 22(1):49-56 (1997).

Molenaar, M. et al., "XTcf-3 Transcription Factor Mediates β-Catenin-Induced Axis Formation in Xenopus Embryos" Cell 86:391-399 (1996).
Murayama, M. et al., "Direct Association of Presenilin-1 with β-Catenin" FEBS Lett. 433:73-77(1998).
Orkin et al., "Report and Recommendations of the Panel to Assess the NIH Investment in Research on Gene Therapy" (1995).
Ozawa, M. et al., "The Fourth Armadillo Repeat of Plakoglobin (γ-Catenin) is Required for Its High Affinity Binding to the Cytoplasmic Domains of E-Cadherin and Desmosomal Cadherin Dsg2, and the Tumor Suppressor APC Protein" J. Biochem. (Tokyo) 118:1077-1082 (1995).
Peifer, M. et al., "A Repeating Amino Acid Motif Shared by Proteins with Diverse Cellular Roles" Cell 76:789-791 (1994).
Price, D.L. and Sisodia, S.S., "Mutant Genes in Familial Alzheimer's Disease and Transgenic Models" Annu. Rev. Neurosci. 21:479-505 (1998).
Qiu, W.Q. et al., "Insulin-Degrading Enzyme Regulates Extracellular Levels of Amyloid β-Protein by Degradation" J. Biol. Chem. 273(49):32730-32738 (1998).
Riggleman, B. et al., "Molecular Analysis of the Armadillo Locus: Uniformly Distributed Transcripts and a Protein with Novel Internal Repeats are Associated with a *Drosophila* Segment Polarity Gene" Genes Dev. 3:96-113 (1989).
Rubinfeld, B. et al., "The APC Protein and E-Cadherin Form Similar but Independent Complexes with α-Catenin, β-Catenin, and Plakoglobin" J. Biol. Chem. 270(10):5549-5555 (1995).
Schendel, Current Protocols in Molecular Biology, pp. 16.1.1-16.1.3 (1998).
Strauss, Current Protocols in Molecular Biology, pp. 6.3.1-6.3.6 (1993). Stahl, B. et al., "Direct Interaction of Alzheimer's Disease-Related Presenilin 1 with Armadillo Protein p0071" J. Biol. Chem. 274(14):9141-9148 (1999).
Stratagene 1991 catalog, p. 66.
Su, L.K. et al., "Association of the APC Tumor Suppressor Protein with Catenins" Science 262:1734-1737 (1993).
Suzuki et al., Gene 200(1-2):149-156 (1997).
Troyanovsky, R.B. et al., "Cadherin Binding Sites of Plakoglobin: Localization, Specificity and Role in Targeting to Adhering Junctions" J. Cell. Sci. 109:3069-3078 (1996).
Verma et al., Nature 389:239-242 (1997).
Wieschaus, E. and Riggleman, R., "Autonomous Requirements for the Segment Polarity Gene Armadillo During *Drosophila* Embryogenesis" Cell 49:177-184 (1987).
Wojciechowska et al., Endocr. Regul. 40(4):129-138 (2006).
Zhang, Z. et al., "Destabilization of β-Catenin by Mutations in Presenilin-1 Potentiates Neuronal Apoptosis" Nature 395:698-702 (1997).
Zhou, J. et al., "Presenilin 1 Interaction in the Brain with a Novel Member of the Armadillo Family" NeuroReport 8:2085-2090 (1997).
GenBank Accession No. AB039670, Kurochkin IV et al., Jan. 26, 2001.
GenBank Accession No. AW952052, Hegde et al., Jun. 1, 2000.
Zhang et al., Nature (1998) 395(6703):698-702.

\* cited by examiner

*Primary Examiner* — Zachariah Lucas
*Assistant Examiner* — Gregory S Emch
(74) *Attorney, Agent, or Firm* — Morrison & Foerster LLP

(57) ABSTRACT

The present invention provides a novel protein containing an armadillo repeat, a gene encoding this protein, and production and use thereof. The present inventors identified a gene named ALEX1 encoding a human-derived novel armadillo repeat-containing protein. It was clarified that ALEX1 interacts with several proteins including insulin-degrading enzyme, presenilin-1, and JNK interacting protein 1. This gene shows significantly decreased expression in cancer cells. The protein ALEX1 and the gene encoding this protein are usable as tools in testing for diseases such as cancer and Alzheimer's disease and developing pharmaceutical agents.

7 Claims, 10 Drawing Sheets

FIGURE 2

```
ALEX1           1 MGRTREAGCVAAGVVIGAGACYCVYRLAWGRDENEKIWDEDEESTDT----------------
ALEX2/KIAA0512  1 MSRVRDAGCVAAGIVIGAGAWYCVYKYTRGRDQTKKRMAKPKNRAVAGTGARARAGLRAG
ALEX3           1 MGYARKVGWVTAGLVIGAGACYCIYRLTRGRKQNK--------------------------

ALEX1          48 -----------------------------------------SEIGVETVKGAKTNAGAGSGAKLQGD
ALEX2/KIAA0512 61 FTIDLGSGFSPPTPVRAEAEDRAQDEASALDTVGAEAVAPAASSAEAQSGAGSQAQEADG
ALEX3          36 ----------------------------------------------EKMAEGGSGDVDDAGDCSGARYNDW

ALEX1          74 SEVKPEVSLGL----------------------------------------------
ALEX2/KIAA0512 121 AGVGPKAESVVGAAMASAIAPPPGVTEALGAEAEAPAMAGAPKVAEAPREAETSRAAVPPG
ALEX3          61 SDDDDDSNE-----------------------------------------------

ALEX1          85 -------------------------EDCPGVKEKAHSGSHSGGGLEAKAKALFNTLKEQA
ALEX2/KIAA0512 181 TVVPTEAAAPTEVTEGPGVAAPTKVAEAAPGVASPTEAAAEAPVPATPTGAAAPTGAAESPG
ALEX3          70 -----------------------------------------------------S------

ALEX1         120 SAKAGKGARVGTISGNRTLAPSLPC-----------------PGGRGGCHPTRSGSRAGGRAS
ALEX2/KIAA0512 241 TSGSPRTAVPGTSAAKKATPGAHTGAIPKATSATGAVPKGGKGVTRSRNGGKGKCKKS
ALEX3          71 -----IVWYPP------------------------------WARIGTEAGTRAR---

ALEX1         167 -----------------------------------------GKSKGKARSKSTR
ALEX2/KIAA0512 301 KVEVDELGMGFRPGDGAAAAAASANGGQAFLAEVPDSEEGESGWTDTESDSDSEPETQR
ALEX3          92 ----------------------------------------AR-------AR
```

FIGURE 3

```
                              Arm 1
ALEX1        180 APATTWPVRRGKFNFPYKIDDILSAPDLQKVINILERTNDPFIQEVALVTLGNNAAYSFN
ALEX2/KIAA0512 361 RGRGRRPVAMQKRPFPYEIDEILGVRDLRKVIALLQKSDDPFIQQVALLTLSNNANYSCN
ALEX3         96 ARATRARRAVQKRASPNSDDTVLSPQELQKVLCIVEMSEKPYILEAALIALGNNAAYAFN
                           Arm 2
ALEX1        240 QNAIRELGGVPIIAKLIKTKDPIIREKTYNALNNLSVNAENQGKIKTYISQVCDDTMVCR
ALEX2/KIAA0512 421 QETIRKLGGLPIIANMINKTDPHIKEKALMAMNNLSENYENQGRLQVYMNKVMDDIMASN
ALEX3        156 RDIIRDLGGLPIVAKILNTRDPIVKEKALIVLNNLSVNAENQRRLKVYMNQVCDDTITSR

ALEX1        300 LDSAVQMAGLRLLTNMTVTNHYQHLLSYSFPDFFALLFLGNHFTKIQIMKLIINFTENPA
ALEX2/KIAA0512 481 LNSAVQVVGLKFLTNMTITNDYQHLLVNSIANFFRLLSQGGKIKVEILKILSNFAENPD
ALEX3        216 LNSSVQLAGLRLLTNMTVTNEYQHMLANSISDFFRLFSAGNEETKLQVLKLLLNLAENPA

ALEX1        360 MTRELVSCKVPSELISLFNKEWDREILLNILTLFENINDNIKNEGLASSRKEFSRSSLFF
ALEX2/KIAA0512 541 MLKKLLSTQVPASFSSLYNSYVESEILINALTLFEIIYDNLRAEVFN--YREFNKGSLFY
ALEX3        276 MTRELLRAQVPSSLGSLFNKKENKEVILKLVIFENINDNFKWEENEPTQNQFGEGSLFF

ALEX1        420 LFKESGVCVKKIKALANHNDLVVKVKVLTKL-------
ALEX2/KIAA0512 599 LCTTSGVCVKKIRALANHHDLLVKVKVIKLVNKF-------
ALEX3        336 FLKEFQVCADKVLGIESHHDFLVKVKVGKFMAKLAEHMFPKSQE
``` ps2-0201-1

SEQUENCE LISTING

```
<160> NUMBER OF SEQ ID NOS: 15

<210> SEQ ID NO 1
<211> LENGTH: 2141
<212> TYPE: DNA
<213> ORGANISM: Homo sapiens
<220> FEATURE:
<221> NAME/KEY: CDS
<222> LOCATION: (372)...(1730)

<400> SEQUENCE: 1
gccgacgcgt gcagacgtcc ttctaatcct agtcttcgtt tggtccggtt gcactcttcc      60
tatagcccag agggcgagag ggcctgtggc ctgggggaag gaggacgagg ttctgcctgg     120
atcccagcag taggacgctg tgccatttgg gaacaaagga atagtctgcc tggaatccct     180
gcagatcttg gggccggagg ccagtccaac ccttggagca ggaagaaacg caaagttgtc     240
aagaaccaag tcgagctgcc tcagagccgg cccgcagtag ctgcagactc cgcccgcgac     300
gtgtgcgcgc ttctctgggc cagagcgagc ctgttttgtg ctcgggttaa gagatttgtc     360
ccagctatac c atg ggc cgc act cgg gaa gct ggc tgc gtg gcc gct ggt     410
             Met Gly Arg Thr Arg Glu Ala Gly Cys Val Ala Ala Gly
               1               5                  10
```

-continued

| | |
|---|---|
| gtg gtt atc ggg gct ggt gcc tgc tac tgt gta tac aga ctg gct tgg<br>Val Val Ile Gly Ala Gly Ala Cys Tyr Cys Val Tyr Arg Leu Ala Trp<br>    15                    20                    25 | 458 |
| gga aga gac gag aac gag aaa atc tgg gac gaa gac gag gag tct acg<br>Gly Arg Asp Glu Asn Glu Lys Ile Trp Asp Glu Asp Glu Glu Ser Thr<br>30                 35                   40                  45 | 506 |
| gac acc tca gag att ggg gtt gag act gtg aaa gga gct aaa act aac<br>Asp Thr Ser Glu Ile Gly Val Glu Thr Val Lys Gly Ala Lys Thr Asn<br>            50                    55                    60 | 554 |
| gct ggg gca ggg tct ggg gcc aaa ctt cag ggt gat tca gag gtc aag<br>Ala Gly Ala Gly Ser Gly Ala Lys Leu Gln Gly Asp Ser Glu Val Lys<br>                65                    70                    75 | 602 |
| cct gag gtg agt ttg gga ctc gag gat tgt ccg ggt gta aaa gag aag<br>Pro Glu Val Ser Leu Gly Leu Glu Asp Cys Pro Gly Val Lys Glu Lys<br>80                     85                   90 | 650 |
| gcc cat tca gga tcc cac agc gga ggt ggc cta gag gcc aag gcc aag<br>Ala His Ser Gly Ser His Ser Gly Gly Gly Leu Glu Ala Lys Ala Lys<br>       95                   100                 105 | 698 |
| gcc ctt ttc aac acg ctg aag gaa cag gca agt gca aag gca ggc aaa<br>Ala Leu Phe Asn Thr Leu Lys Glu Gln Ala Ser Ala Lys Ala Gly Lys<br>110                   115                120                125 | 746 |
| ggg gct agg gtg ggt acc atc tct ggg aac agg acc ctt gca ccg agt<br>Gly Ala Arg Val Gly Thr Ile Ser Gly Asn Arg Thr Leu Ala Pro Ser<br>                 130                   135                140 | 794 |
| tta ccc tgc cca gga ggc agg ggt gga ggc tgc cac ccc acc agg agt<br>Leu Pro Cys Pro Gly Gly Arg Gly Gly Gly Cys His Pro Thr Arg Ser<br>                    145                   150                155 | 842 |
| gga tct agg gcc ggg ggc agg gca agt gga aaa tcc aag gga aag gcc<br>Gly Ser Arg Ala Gly Gly Arg Ala Ser Gly Lys Ser Lys Gly Lys Ala<br>               160                    165                170 | 890 |
| cga agt aag agc acc agg gct cca gct aca aca tgg cct gtc cgg aga<br>Arg Ser Lys Ser Thr Arg Ala Pro Ala Thr Thr Trp Pro Val Arg Arg<br>175                 180                185 | 938 |
| ggc aag ttc aac ttt cct tat aaa att gat gat att ctg agt gct ccc<br>Gly Lys Phe Asn Phe Pro Tyr Lys Ile Asp Asp Ile Leu Ser Ala Pro<br>190                   195                200                205 | 986 |
| gac ctc caa aag gtc ctc aac atc ctg gag cga aca aat gat cct ttt<br>Asp Leu Gln Lys Val Leu Asn Ile Leu Glu Arg Thr Asn Asp Pro Phe<br>               210                   215                220 | 1034 |
| att caa gaa gta gcc ttg gtc act ctg ggt aac aat gca gca tat tca<br>Ile Gln Glu Val Ala Leu Val Thr Leu Gly Asn Asn Ala Ala Tyr Ser<br>                   225                  230                235 | 1082 |
| ttt aac cag aat gcc ata cgt gaa ttg ggt ggt gtc cca att att gca<br>Phe Asn Gln Asn Ala Ile Arg Glu Leu Gly Gly Val Pro Ile Ile Ala<br>               240                    245                250 | 1130 |
| aaa ctg ata aaa aca aaa gac ccc ata att agg gaa aag act tac aat<br>Lys Leu Ile Lys Thr Lys Asp Pro Ile Ile Arg Glu Lys Thr Tyr Asn<br>255                   260                265 | 1178 |
| gcc ctt aat aac ttg agt gtg aac gca gaa aat cag ggc aag att aag<br>Ala Leu Asn Asn Leu Ser Val Asn Ala Glu Asn Gln Gly Lys Ile Lys<br>270                   275                280                285 | 1226 |
| acg tac atc agt caa gtg tgt gat gac acc atg gtc tgt cgc ttg gac<br>Thr Tyr Ile Ser Gln Val Cys Asp Asp Thr Met Val Cys Arg Leu Asp<br>               290                   295                300 | 1274 |
| tca gct gtg cag atg gct ggg cta aga ctg tta acc aac atg act gtg<br>Ser Ala Val Gln Met Ala Gly Leu Arg Leu Leu Thr Asn Met Thr Val<br>                  305                  310                315 | 1322 |
| act aat cat tac caa cat ttg ctt tcc tat tct ttt cca gac ttt ttt<br>Thr Asn His Tyr Gln His Leu Leu Ser Tyr Ser Phe Pro Asp Phe Phe<br>320                   325                330 | 1370 |

```
gct ttg tta ttc ctg gga aat cac ttc acc aag ata cag att atg aaa    1418
Ala Leu Leu Phe Leu Gly Asn His Phe Thr Lys Ile Gln Ile Met Lys
    335                 340                 345 cta att ata aac ttt act gaa aat cca gcc atg aca aga gag ctg gtc    1466
Leu Ile Ile Asn Phe Thr Glu Asn Pro Ala Met Thr Arg Glu Leu Val
350                 355                 360                 365 agt tgt aaa gta cca tca gaa ttg att tcc ctc ttt aat aaa gaa tgg    1514
Ser Cys Lys Val Pro Ser Glu Leu Ile Ser Leu Phe Asn Lys Glu Trp
                370                 375                 380 gat aga gag att ctt ctt aat atc ctt acc cta ttt gag aat ata aat    1562
Asp Arg Glu Ile Leu Leu Asn Ile Leu Thr Leu Phe Glu Asn Ile Asn
            385                 390                 395 gac aac ata aaa aat gaa ggg ctc gca tca tcc agg aaa gaa ttc agc    1610
Asp Asn Ile Lys Asn Glu Gly Leu Ala Ser Ser Arg Lys Glu Phe Ser
        400                 405                 410 aga agt tca ctt ttt ttc tta ttc aaa gag tct gga gtt tgt gtt aag    1658
Arg Ser Ser Leu Phe Phe Leu Phe Lys Glu Ser Gly Val Cys Val Lys
    415                 420                 425 aaa atc aaa gca cta gca aat cac aat gat ctg gtg gtg aaa gta aaa    1706
Lys Ile Lys Ala Leu Ala Asn His Asn Asp Leu Val Val Lys Val Lys
430                 435                 440                 445 gtc ctg aaa gta tta acc aaa ctc taatttggag tctgtcccaa acaatattga   1760
Val Leu Lys Val Leu Thr Lys Leu
                450 gatatttgca gttggtacga tgtgatttgt aaattctttg ttttcattg tgcgtatatg    1820 gtaaagagat cttttcagct gctattttgg aataatgact atcatatatc ataacagtga   1880 ctgatgttgg ttgtaatggt tgggtttagg atgaaccatt ttaaggatgc caaatgaaat   1940 attagtattt gtacacagaa agaatttatt gatttgatct tattacctag attgagattt   2000 tttaatcttt cctctaccta aactgacaat gaattggtta tacatcatgc ataagctaca   2060 cttttatatt agtttatatt tgttattcta agacttgtgt ttcatcaata aagttgtgtt   2120 ttaagcagca gaaaaaaaaa a                                             2141

<210> SEQ ID NO 2
<211> LENGTH: 2124
<212> TYPE: DNA
<213> ORGANISM: Homo sapiens
<220> FEATURE:
<221> NAME/KEY: CDS
<222> LOCATION: (364)...(1725)

<400> SEQUENCE: 2
cctcaaggta cggtccggaa ttcccgggtc gacccacgcg tccggcactc ttcctatagc     60
ccagagggcg aagagggcct gtggcctggg ggaaggagga cgaggttctg cctggatccc    120
agcaggacgc tgtgccattt gggaacaaag gaatagtctg cctggaatcc ctgcagatct    180
tggggccgga ggccagtcca acccttggag caggaagaaa cgcaaagttg tcaagaacca    240
agtcgagctg cctcagagcc ggcccgcagt agctgcagac tccgcccgcg acgtgtgcgc    300
gcttctctgg gccagagcga gcctgttttg tgctcgggtt aagagatttg tcccagctat    360 acc atg ggc cgc act cgg gaa gct ggc tgc gtg gcc gct ggt gtg gtt    408
    Met Gly Arg Thr Arg Glu Ala Gly Cys Val Ala Ala Gly Val Val
    1               5                   10                  15 atc ggg gct ggt gcc tgc tac tgt gta tac aga ctg gct tgg gga aga    456
Ile Gly Ala Gly Ala Cys Tyr Cys Val Tyr Arg Leu Ala Trp Gly Arg
                20                  25                  30 gac gag aac gag aaa atc tgg gac gaa gac gag gag tct acg gac acc    504
Asp Glu Asn Glu Lys Ile Trp Asp Glu Asp Glu Glu Ser Thr Asp Thr
```

```
                      35                  40                  45
tca gag att ggg gtt gag act gtg aaa gga gct aaa act aac gct ggg    552
Ser Glu Ile Gly Val Glu Thr Val Lys Gly Ala Lys Thr Asn Ala Gly
         50                  55                  60 gca ggg tct ggg gcc aaa ctt cag ggt gat tca gag gtc aag cct gag    600
Ala Gly Ser Gly Ala Lys Leu Gln Gly Asp Ser Glu Val Lys Pro Glu
 65                  70                  75 gtg agt ttg gga ctc gag gat tgt ccg ggt gta aaa gag aag gcc cat    648
Val Ser Leu Gly Leu Glu Asp Cys Pro Gly Val Lys Glu Lys Ala His
             80                  85                  90                  95 tca gga tcc cac agc gga ggt ggc cta gag gcc aag gcc aag gcc ctt    696
Ser Gly Ser His Ser Gly Gly Gly Leu Glu Ala Lys Ala Lys Ala Leu
                100                 105                 110 ttc aac acg ctg aag gaa cag gca agt gca aag gca ggc aaa ggg gct    744
Phe Asn Thr Leu Lys Glu Gln Ala Ser Ala Lys Ala Gly Lys Gly Ala
            115                 120                 125 agg gtg ggt acc atc tct ggg aac agg acc ctt gca ccg agt tta ccc    792
Arg Val Gly Thr Ile Ser Gly Asn Arg Thr Leu Ala Pro Ser Leu Pro
130                 135                 140 tgc cca gga ggc agg ggt gga ggc tgc cac ccc acc agg agt gga tct    840
Cys Pro Gly Gly Arg Gly Gly Gly Cys His Pro Thr Arg Ser Gly Ser
            145                 150                 155 agg gcc ggg ggc agg gca agt gga aaa tcc aag gga aag gcc cga agt    888
Arg Ala Gly Gly Arg Ala Ser Gly Lys Ser Lys Gly Lys Ala Arg Ser
160                 165                 170                 175 aag agc acc agg gct cca gct aca aca tgg cct gtc cgg aga ggc aag    936
Lys Ser Thr Arg Ala Pro Ala Thr Thr Trp Pro Val Arg Arg Gly Lys
            180                 185                 190 ttc aac ttt cct tat aaa att gat gat att ctg agt gct ccc gac ctc    984
Phe Asn Phe Pro Tyr Lys Ile Asp Asp Ile Leu Ser Ala Pro Asp Leu
            195                 200                 205 caa aag gtc ctc aac atc ctg gag cga aca aat gat cct ttt att caa   1032
Gln Lys Val Leu Asn Ile Leu Glu Arg Thr Asn Asp Pro Phe Ile Gln
            210                 215                 220 gaa gta gcc ttg gtc act ctg ggt aac aat gca gca tat tca ttt aac   1080
Glu Val Ala Leu Val Thr Leu Gly Asn Asn Ala Ala Tyr Ser Phe Asn
225                 230                 235 cag aat gcc ata cgt gaa ttg ggt ggt gtc cca att att gca aaa ctg   1128
Gln Asn Ala Ile Arg Glu Leu Gly Gly Val Pro Ile Ile Ala Lys Leu
240                 245                 250                 255 ata aaa aca aaa gac ccc ata att agg gaa aag act tac aat gcc ctt   1176
Ile Lys Thr Lys Asp Pro Ile Ile Arg Glu Lys Thr Tyr Asn Ala Leu
            260                 265                 270 aat aac ttg agt gtg aac gca gaa aat cag ggc aag att aag acg tac   1224
Asn Asn Leu Ser Val Asn Ala Glu Asn Gln Gly Lys Ile Lys Thr Tyr
            275                 280                 285 atc agt caa gtg tgt gat gac acc atg gtc tgt cgc ttg gac tca gct   1272
Ile Ser Gln Val Cys Asp Asp Thr Met Val Cys Arg Leu Asp Ser Ala
            290                 295                 300 gtg cag atg gct ggg cta aga ctg tta acc aac atg act gtg act aat   1320
Val Gln Met Ala Gly Leu Arg Leu Leu Thr Asn Met Thr Val Thr Asn
305                 310                 315 cat tac caa cat ttg ctt tcc tat tct ttt cca gac ttt ttt gct ttg   1368
His Tyr Gln His Leu Leu Ser Tyr Ser Phe Pro Asp Phe Phe Ala Leu
320                 325                 330                 335 tta ttc ctg gga aat cac ttc acc aag ata cag att atg aaa cta att   1416
Leu Phe Leu Gly Asn His Phe Thr Lys Ile Gln Ile Met Lys Leu Ile
            340                 345                 350 ata aac ttt act gaa aat cca gcc atg aca aga gag ctg gtc agt tgt   1464
Ile Asn Phe Thr Glu Asn Pro Ala Met Thr Arg Glu Leu Val Ser Cys
```

```
                     355                 360                 365
aaa gta cca tca gaa ttg att tcc ctc ttt aat aaa gaa tgg gat aga   1512
Lys Val Pro Ser Glu Leu Ile Ser Leu Phe Asn Lys Glu Trp Asp Arg
        370                 375                 380 gag att ctt ctt aat atc ctt acc cta ttt gag aat ata aat gac aac   1560
Glu Ile Leu Leu Asn Ile Leu Thr Leu Phe Glu Asn Ile Asn Asp Asn
385                 390                 395 ata aaa aat gaa ggg ctc gca tca tcc agg aaa gaa ttc agc aga agt   1608
Ile Lys Asn Glu Gly Leu Ala Ser Ser Arg Lys Glu Phe Ser Arg Ser
400                 405                 410                 415 tca ctt ttt ttc tta ttc aaa gag tct gga gtt tgt gtt aag aaa atc   1656
Ser Leu Phe Phe Leu Phe Lys Glu Ser Gly Val Cys Val Lys Lys Ile
            420                 425                 430 aaa gca cta gca aat cac aat gat ctg gtg gtg aaa gta aaa gtc ctg   1704
Lys Ala Leu Ala Asn His Asn Asp Leu Val Val Lys Val Lys Val Leu
        435                 440                 445 aaa gta tta acc aaa ctc taa tttggagtct gtcccaaaca atattgagat      1755
Lys Val Leu Thr Lys Leu
        450 atttgcagtt ggtacgatgt gatttgtaaa ttctttgttt ttcattgtgc gtatatggta 1815 aagagatctt ttcagctgct attttggaat aatgactatc atatatcata acagtgactg 1875 atgttggttg taatggttgg gtttaggatg aaccatttta aggatgccaa atgaaatatt 1935 agtatttgta cacagaaaga atttattgat ttgatcttat tacctagatt gagattttt  1995 aatctttcct ctacctaaac tgacaatgaa ttggttatac atcatgcata agctacactt 2055 ttatattagt ttatatttgt tattctaaga cttgtgtttc atcaataaag ttgtgtttta 2115 agcagccgg                                                        2124

<210> SEQ ID NO 3
<211> LENGTH: 453
<212> TYPE: PRT
<213> ORGANISM: Homo sapiens

<400> SEQUENCE: 3

Met Gly Arg Thr Arg Glu Ala Gly Cys Val Ala Ala Gly Val Val Ile
1               5                   10                  15

Gly Ala Gly Ala Cys Tyr Cys Val Tyr Arg Leu Ala Trp Gly Arg Asp
            20                  25                  30

Glu Asn Glu Lys Ile Trp Asp Glu Asp Glu Glu Ser Thr Asp Thr Ser
        35                  40                  45

Glu Ile Gly Val Glu Thr Val Lys Gly Ala Lys Thr Asn Ala Gly Ala
    50                  55                  60

Gly Ser Gly Ala Lys Leu Gln Gly Asp Ser Glu Val Lys Pro Glu Val
65                  70                  75                  80

Ser Leu Gly Leu Glu Asp Cys Pro Gly Val Lys Glu Lys Ala His Ser
                85                  90                  95

Gly Ser His Ser Gly Gly Leu Glu Ala Lys Ala Lys Ala Leu Phe
            100                 105                 110

Asn Thr Leu Lys Glu Gln Ala Ser Ala Lys Ala Gly Lys Gly Ala Arg
        115                 120                 125

Val Gly Thr Ile Ser Gly Asn Arg Thr Leu Ala Pro Ser Leu Pro Cys
    130                 135                 140

Pro Gly Gly Arg Gly Gly Gly Cys His Pro Thr Arg Ser Gly Ser Arg
145                 150                 155                 160

Ala Gly Gly Arg Ala Ser Gly Lys Ser Lys Gly Lys Ala Arg Ser Lys
                165                 170                 175
```

```
Ser Thr Arg Ala Pro Ala Thr Thr Trp Pro Val Arg Arg Gly Lys Phe
        180                 185                 190

Asn Phe Pro Tyr Lys Ile Asp Asp Ile Leu Ser Ala Pro Asp Leu Gln
        195                 200                 205

Lys Val Leu Asn Ile Leu Glu Arg Thr Asn Asp Pro Phe Ile Gln Glu
    210                 215                 220

Val Ala Leu Val Thr Leu Gly Asn Asn Ala Ala Tyr Ser Phe Asn Gln
225                 230                 235                 240

Asn Ala Ile Arg Glu Leu Gly Gly Val Pro Ile Ile Ala Lys Leu Ile
            245                 250                 255

Lys Thr Lys Asp Pro Ile Ile Arg Glu Lys Thr Tyr Asn Ala Leu Asn
        260                 265                 270

Asn Leu Ser Val Asn Ala Glu Asn Gln Gly Lys Ile Lys Thr Tyr Ile
        275                 280                 285

Ser Gln Val Cys Asp Asp Thr Met Val Cys Arg Leu Asp Ser Ala Val
    290                 295                 300

Gln Met Ala Gly Leu Arg Leu Leu Thr Asn Met Thr Val Thr Asn His
305                 310                 315                 320

Tyr Gln His Leu Leu Ser Tyr Ser Phe Pro Asp Phe Phe Ala Leu Leu
            325                 330                 335

Phe Leu Gly Asn His Phe Thr Lys Ile Gln Ile Met Lys Leu Ile Ile
        340                 345                 350

Asn Phe Thr Glu Asn Pro Ala Met Thr Arg Glu Leu Val Ser Cys Lys
        355                 360                 365

Val Pro Ser Glu Leu Ile Ser Leu Phe Asn Lys Glu Trp Asp Arg Glu
    370                 375                 380

Ile Leu Leu Asn Ile Leu Thr Leu Phe Glu Asn Ile Asn Asp Asn Ile
385                 390                 395                 400

Lys Asn Glu Gly Leu Ala Ser Ser Arg Lys Glu Phe Ser Arg Ser Ser
            405                 410                 415

Leu Phe Phe Leu Phe Lys Glu Ser Gly Val Cys Val Lys Lys Ile Lys
        420                 425                 430

Ala Leu Ala Asn His Asn Asp Leu Val Val Lys Val Lys Val Leu Lys
        435                 440                 445

Val Leu Thr Lys Leu
    450

<210> SEQ ID NO 4
<211> LENGTH: 23
<212> TYPE: DNA
<213> ORGANISM: Artificial Sequence
<220> FEATURE:
<223> OTHER INFORMATION: Synthetically constructed primer sequence

<400> SEQUENCE: 4
gtgctcgggt taagagattt gtc                                             23

<210> SEQ ID NO 5
<211> LENGTH: 19
<212> TYPE: DNA
<213> ORGANISM: Artificial Sequence
<220> FEATURE:
<223> OTHER INFORMATION: Synthetically constructed primer sequence

<400> SEQUENCE: 5
tcacaatgat ctggtggtg                                                  19
```

```
<210> SEQ ID NO 6
<211> LENGTH: 20
<212> TYPE: DNA
<213> ORGANISM: Artificial Sequence
<220> FEATURE:
<223> OTHER INFORMATION: Synthetically constructed primer sequence

<400> SEQUENCE: 6
caacatgact gtgactaatc                                                 20

<210> SEQ ID NO 7
<211> LENGTH: 18
<212> TYPE: DNA
<213> ORGANISM: Artificial Sequence
<220> FEATURE:
<223> OTHER INFORMATION: Synthetically constructed primer sequence

<400> SEQUENCE: 7
agctcctttc acagtctc                                                   18

<210> SEQ ID NO 8
<211> LENGTH: 25
<212> TYPE: DNA
<213> ORGANISM: Artificial Sequence
<220> FEATURE:
<223> OTHER INFORMATION: Synthetically constructed primer sequence

<400> SEQUENCE: 8
acccaaccat tacaaccaac atcag                                           25

<210> SEQ ID NO 9
<211> LENGTH: 28
<212> TYPE: DNA
<213> ORGANISM: Artificial Sequence
<220> FEATURE:
<223> OTHER INFORMATION: Synthetically constructed primer sequence

<400> SEQUENCE: 9
ggccatgttg tagctggagc cctggtgc                                        28

<210> SEQ ID NO 10
<211> LENGTH: 21
<212> TYPE: DNA
<213> ORGANISM: Artificial Sequence
<220> FEATURE:
<223> OTHER INFORMATION: Synthetically constructed primer sequence

<400> SEQUENCE: 10
tagcagcacc taccaaggta g                                               21

<210> SEQ ID NO 11
<211> LENGTH: 20
<212> TYPE: DNA
<213> ORGANISM: Artificial Sequence
<220> FEATURE:
<223> OTHER INFORMATION: Synthetically constructed primer sequence

<400> SEQUENCE: 11
tgccttgctt cagaaatctg                                                 20

<210> SEQ ID NO 12
<211> LENGTH: 21
<212> TYPE: DNA
<213> ORGANISM: Artificial Sequence
<220> FEATURE:
<223> OTHER INFORMATION: Synthetically constructed primer sequence

<400> SEQUENCE: 12
```

-continued

```
cccagttcgt ctacttcaac t                                              21
```

<210> SEQ ID NO 13
<211> LENGTH: 21
<212> TYPE: DNA
<213> ORGANISM: Artificial Sequence
<220> FEATURE:
<223> OTHER INFORMATION: Synthetically constructed primer sequence

<400> SEQUENCE: 13

```
cttccacact gcaaaatcat g                                              21
```

<210> SEQ ID NO 14
<211> LENGTH: 632
<212> TYPE: PRT
<213> ORGANISM: Homo sapiens

<400> SEQUENCE: 14

```
Met Ser Arg Val Arg Asp Ala Gly Cys Val Ala Ala Gly Ile Val Ile
1               5                   10                  15

Gly Ala Gly Ala Trp Tyr Cys Val Tyr Lys Tyr Thr Arg Gly Arg Asp
            20                  25                  30

Gln Thr Lys Lys Arg Met Ala Lys Pro Lys Asn Arg Ala Val Ala Gly
        35                  40                  45

Thr Gly Ala Arg Ala Arg Ala Gly Leu Arg Ala Gly Phe Thr Ile Asp
    50                  55                  60

Leu Gly Ser Gly Phe Ser Pro Pro Thr Pro Val Arg Ala Glu Ala Glu
65                  70                  75                  80

Asp Arg Ala Gln Asp Glu Ala Ser Ala Leu Asp Thr Val Gly Ala Glu
                85                  90                  95

Ala Val Ala Pro Ala Ala Ser Ser Ala Glu Ala Gln Ser Gly Ala Gly
            100                 105                 110

Ser Gln Ala Gln Glu Ala Asp Gly Ala Gly Val Gly Pro Lys Ala Glu
        115                 120                 125

Ser Val Val Gly Ala Ala Met Ala Ser Ala Ile Ala Pro Pro Pro Gly
    130                 135                 140

Val Thr Glu Ala Leu Gly Ala Ala Glu Ala Pro Ala Met Ala Gly Ala
145                 150                 155                 160

Pro Lys Val Ala Glu Ala Pro Arg Glu Ala Glu Thr Ser Arg Ala Ala
                165                 170                 175

Val Pro Pro Gly Thr Val Val Pro Thr Glu Ala Ala Pro Thr Glu
            180                 185                 190

Val Thr Glu Gly Pro Gly Val Ala Ala Pro Thr Lys Val Ala Glu Ala
        195                 200                 205

Pro Gly Val Ala Ser Pro Thr Glu Ala Ala Glu Ala Pro Val Pro Ala
    210                 215                 220

Thr Pro Thr Gly Ala Ala Ala Pro Thr Gly Ala Ala Glu Ser Pro Gly
225                 230                 235                 240

Thr Ser Gly Ser Pro Arg Thr Ala Val Val Pro Gly Thr Ser Ala Ala
                245                 250                 255

Lys Lys Ala Thr Pro Gly Ala His Thr Gly Ile Pro Lys Ala Thr
            260                 265                 270

Ser Ala Thr Gly Ala Val Pro Lys Gly Gly Lys Gly Val Thr Arg
        275                 280                 285

Ser Arg Asn Gly Gly Lys Gly Lys Gly Lys Lys Ser Lys Val Glu Val
    290                 295                 300
```

Asp Glu Leu Gly Met Gly Phe Arg Pro Gly Asp Ala Ala Ala
305                 310                 315                 320

Ala Ala Ala Ser Ala Asn Gly Gly Gln Ala Phe Leu Ala Glu Val Pro
            325                 330                 335

Asp Ser Glu Glu Gly Glu Ser Gly Trp Thr Asp Thr Gly Ser Asp Ser
        340                 345                 350

Asp Ser Glu Pro Glu Thr Gln Arg Arg Gly Arg Gly Arg Pro Val
        355                 360                 365

Ala Met Gln Lys Arg Pro Phe Pro Tyr Glu Ile Asp Glu Ile Leu Gly
    370                 375                 380

Val Arg Asp Leu Arg Lys Val Leu Ala Leu Leu Gln Lys Ser Asp Asp
385                 390                 395                 400

Pro Phe Ile Gln Gln Val Ala Leu Leu Thr Leu Ser Asn Asn Ala Asn
                405                 410                 415

Tyr Ser Cys Asn Gln Glu Thr Ile Arg Lys Leu Gly Gly Leu Pro Ile
            420                 425                 430

Ile Ala Asn Met Ile Asn Lys Thr Asp Pro His Ile Lys Glu Lys Ala
        435                 440                 445

Leu Met Ala Met Asn Asn Leu Ser Glu Asn Tyr Glu Asn Gln Gly Arg
    450                 455                 460

Leu Gln Val Tyr Met Asn Lys Val Met Asp Asp Ile Met Ala Ser Asn
465                 470                 475                 480

Leu Asn Ser Ala Val Gln Val Gly Leu Lys Phe Leu Thr Asn Met
                485                 490                 495

Thr Ile Thr Asn Asp Tyr Gln His Leu Leu Val Asn Ser Ile Ala Asn
                500                 505                 510

Phe Phe Arg Leu Leu Ser Gln Gly Gly Lys Ile Lys Val Glu Ile
            515                 520                 525

Leu Lys Ile Leu Ser Asn Phe Ala Glu Asn Pro Asp Met Leu Lys Lys
530                 535                 540

Leu Leu Ser Thr Gln Val Pro Ala Ser Phe Ser Ser Leu Tyr Asn Ser
545                 550                 555                 560

Tyr Val Glu Ser Glu Ile Leu Ile Asn Ala Leu Thr Leu Phe Glu Ile
                565                 570                 575

Ile Tyr Asp Asn Leu Arg Ala Glu Val Phe Asn Tyr Arg Glu Phe Asn
            580                 585                 590

Lys Gly Ser Leu Phe Tyr Leu Cys Thr Thr Ser Gly Val Cys Val Lys
            595                 600                 605

Lys Ile Arg Ala Leu Ala Asn His His Asp Leu Leu Lys Val Lys
        610                 615                 620

Val Ile Lys Leu Val Asn Lys Phe
625                 630

<210> SEQ ID NO 15
<211> LENGTH: 379
<212> TYPE: PRT
<213> ORGANISM: Homo sapiens

<400> SEQUENCE: 15

Met Gly Tyr Ala Arg Lys Val Gly Trp Val Thr Ala Gly Leu Val Ile
1               5                   10                  15

Gly Ala Gly Ala Cys Tyr Cys Ile Tyr Arg Leu Thr Arg Gly Arg Lys
            20                  25                  30

Gln Asn Lys Glu Lys Met Ala Glu Gly Gly Ser Gly Asp Val Asp Asp
        35                  40                  45

-continued

```
Ala Gly Asp Cys Ser Gly Ala Arg Tyr Asn Asp Trp Ser Asp Asp Asp
    50                  55                  60

Asp Asp Ser Asn Glu Ser Lys Ser Ile Val Trp Tyr Pro Pro Trp Ala
65                  70                  75                  80

Arg Ile Gly Thr Glu Ala Gly Thr Arg Ala Arg Ala Arg Ala Arg Ala
                85                  90                  95

Arg Ala Thr Arg Ala Arg Arg Ala Val Gln Lys Arg Ala Ser Pro Asn
            100                 105                 110

Ser Asp Asp Thr Val Leu Ser Pro Gln Glu Leu Gln Lys Val Leu Cys
            115                 120                 125

Leu Val Glu Met Ser Glu Lys Pro Tyr Ile Leu Glu Ala Ala Leu Ile
        130                 135                 140

Ala Leu Gly Asn Asn Ala Ala Tyr Ala Phe Asn Arg Asp Ile Ile Arg
145                 150                 155                 160

Asp Leu Gly Gly Leu Pro Ile Val Ala Lys Ile Leu Asn Thr Arg Asp
                165                 170                 175

Pro Ile Val Lys Glu Lys Ala Leu Ile Val Leu Asn Asn Leu Ser Val
            180                 185                 190

Asn Ala Glu Asn Gln Arg Arg Leu Lys Val Tyr Met Asn Gln Val Cys
            195                 200                 205

Asp Asp Thr Ile Thr Ser Arg Leu Asn Ser Ser Val Gln Leu Ala Gly
        210                 215                 220

Leu Arg Leu Leu Thr Asn Met Thr Val Thr Asn Glu Tyr Gln His Met
225                 230                 235                 240

Leu Ala Asn Ser Ile Ser Asp Phe Phe Arg Leu Phe Ser Ala Gly Asn
                245                 250                 255

Glu Glu Thr Lys Leu Gln Val Leu Lys Leu Leu Leu Asn Leu Ala Glu
            260                 265                 270

Asn Pro Ala Met Thr Arg Glu Leu Leu Arg Ala Gln Val Pro Ser Ser
            275                 280                 285

Leu Gly Ser Leu Phe Asn Lys Lys Glu Asn Lys Glu Val Ile Leu Lys
        290                 295                 300

Leu Leu Val Ile Phe Glu Asn Ile Asn Asp Asn Phe Lys Trp Glu Glu
305                 310                 315                 320

Asn Glu Pro Thr Gln Asn Gln Phe Gly Glu Gly Ser Leu Phe Phe Phe
                325                 330                 335

Leu Lys Glu Phe Gln Val Cys Ala Asp Lys Val Leu Gly Ile Glu Ser
            340                 345                 350

His His Asp Phe Leu Val Lys Val Lys Val Gly Lys Phe Met Ala Lys
            355                 360                 365

Leu Ala Glu His Met Phe Pro Lys Ser Gln Glu
        370                 375
```

HUMAN ALEX1 PROTEINS

CROSS-REFERENCE TO RELATED APPLICATIONS

This application is a division of U.S. Ser. No. 10/204,751 filed Jan. 15, 2003, now U.S. Pat. No. 7,691,992, issued 6 Apr. 2010, which is a national phase of International Application No. PCT/JP2001/001373 filed 23 Feb. 2001 and claims priority from Japanese Patent Application No. 2000-54466 filed 25 Feb. 2000. The contents of the applications listed in this paragraph are fully incorporated by reference herein.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 532842000210Seqlist.txt | Apr. 13, 2010 | 27,970 bytes |

TECHNICAL FIELD

This invention relates to a novel protein comprising a repetitive sequence called armadillo repeat, and a gene encoding this protein. In addition, this invention relates to the use of the obtained cDNA and proteins encoded by the cDNA in diagnosis of human cancer or Alzheimer's disease pathology.

BACKGROUND ART

Members of the armadillo (Arm) family of proteins are homologous to the product of the armadillo gene of *Drosophila* and have been implicated in a variety of important cell functions. The common characteristic of all armadillo-related proteins is a series of imperfect 42-amino acid repeats (Arm motifs) (Peifer, M. et al. (1994) Cell 76, 789-791). The motif was first described in 1989 in the armadillo locus in *Drosophila* (Riggleman, B. et al. (1989) Genes Dev. 3, 96-113). Since then, a number of genes encoding proteins containing homologous motifs have been cloned and sequenced. These include: human α-, β-, γ-, δ-catenins; the tumor suppressor adenoma polyposis coli (APC); p120, the substrate of src protein kinases; importin involved in the nuclear import of proteins; and smgGDS involved in the guanine nucleotide conversion of low molecular weight G-proteins such as ras (Hatzfeld, M. (1999) Int. Rev. Cytol. 186, 179-224). Arm motifs are found throughout evolution and are conserved even between distant species like yeast and human. Arm repeats in proteins usually occur in tandem and, so far, no proteins with less than six repeats have been described. It is known that armadillo-related proteins interact with numerous different proteins through their Arm domains (Ozawa, M. et al. (1995) J. Biochem. (Tokyo) 118, 1077-1082; Rubinfeld, B. et al. (1995) J. Biol. Chem. 270, 5549-5555; Troyanovsky, R. B. et al. (1996) J. Cell Sci. 109, 3069-3078; Murayama, M. et al. (1998) FEBS Lett. 433, 73-77).

Recent studies have implicated Arm proteins in Alzheimer's disease. Human Arm-proteins β-, γ-, δ-catenins and p0071 have been found to interact with presenilin-1 (PS1) protein (Zhou, J. et al. (1997) NeuroReport 8, 2085-2090; Zhang, Z. et al. (1998) Nature 395, 698-702; Stahl, B. et al. (1999) J. Biol. Chem. 274, 9141-9148). Mutations of the PS1 and presenilin-2 (PS2) genes are responsible for the majority of cases of early-onset familiar Alzheimer's disease (Price, D. L., and Sisodia, S. S. (1998) Annu. Rev. Neurosci. 21, 479-505). PS1 and PS2 mutations increase the levels of the β-amyloid peptide 1-42 deposited at the core of amyloid plaques suggesting that presenilins are involved in the processing of amyloid precursor proteins (APP). The significance of interaction of catenins with presenilins is unclear, although it appears that wild-type PS1 can stabilize β-catenin, whereas PS1 mutants show loss of the stabilizing function.

As mentioned above, Arm proteins serve different functions in cells. The *Drosophila* armadillo gene was first identified as a component of the wingless signaling cascade (Wieschaus, E., and Riggleman, R. (1987) Cell 49, 177-184). Similarly, the vertebrate equivalent of armadillo, β-catenin, is known as a critical component of the Wnt/Wingless growth factor signaling pathway that governs cell fate choice in early embryogenesis. The mechanism of how β-catenin transduces the Wnt/wingless signal has been elucidated by the discovery that β-catenin forms a complex with members of the TCF/LEF-1 family of transcription factors that enters the nucleus (Behrens, J. et al. (1996) Nature 382, 638-642; Molenaar, M. et al. (1996) Cell 86, 391-399). TCFs are poor transcriptional activators, but complexes of TCF/LEF-1 and β-catenin act as strong transcriptional activators.

In addition to its role in signaling functions, β-catenin has an essential role in the morphogenesis of solid tissues and the subsequent maintenance of tissue integrity. β-catenin binds to the highly conserved cytoplasmic domain of cadherins and to α-catenin, which binds to actin. The cadherin-catenin complex is a target of regulatory signals that govern cellular adhesiveness and mobility (Kinch, M. S. et al. (1995) J. Cell. Biol. 130, 461-471).

In mammalian cells, β-catenin interacts with the tumor suppressor gene product APC (Su, L. K. et al. (1993) Science 262, 1734-1737). Mutations in APC gene are associated with familial and sporadic colorectal cancer (Kinzler, K. W., and Vogelstein, B. (1996) Cell 87, 159-170). APC is thought to function to decrease β-catenin stability since APC mutant proteins lacking β-catenin binding site display elevated levels of cytosolic β-catenin and constitutive transcriptional activation of the β-catenin/TCF complex.

Thus, Arm proteins are involved in the maintenance of tissue structures as well as intracellular signaling functions. They play a central role in tumorigenesis and are implicated in Alzheimer's disease. Therefore, it is thought that newly discovered members of the Arm family of proteins might be involved in these pathologies and, thus, represent useful targets for the development of therapeutics.

Recent studies from several laboratories demonstrated that insulin-degrading enzyme (IDE) is the main amyloid β peptide-degrading enzyme at neutral pH in rat and human nervous tissues (Kurochkin, I. V., and Goto, S. (1994) FEBS Lett. 345, 33-37; McDermott, J. R., and Gibson, A. M. (1997) Neurochem. Res. 22, 49-56; Qiu, W. Q. et al. (1998) J. Biol. Chem. 273, 32730-32738). Since most of IDE is localized to the cytoplasm, it is unclear how the protease could gain access to amyloid β peptide generated in a secretory organelle from an amyloid precursor protein (APP).

DISCLOSURE OF THE INVENTION

An objective of this invention is to provide a novel protein comprising a repetitive sequence called armadillo repeat, and a gene encoding this protein. Another objective of this invention is to provide the use of the obtained cDNA and proteins encoded by the cDNA in diagnosis of human cancer or Alzheimer's disease pathology and development of pharmaceutical agents.

The present inventors hypothesized that IDE might get into contact with amyloid β peptide if adapter proteins exist linking the protease to compartments where the peptide is generated. The inventors also thought that a defect in function of putative adapter protein might be responsible for accumulation of amyloid β peptide observed in Alzheimer's disease. Based on this hypothesis, the inventors used the yeast two-hybrid screen as an approach to find IDE potential protein partners that could fulfill the above-mentioned role. This led the inventors to the cloning of novel cDNA for a novel armadillo (Arm) repeat protein named ALEX1 (Arm protein Lost in Epithelial cancers on chromosome X-1), which has 453 amino acids.

In vitro experiments suggest a direct interaction between IDE and ALEX1 protein. The protein predicted from its nucleotide sequence contains two regions called armadillo repeats that are thought to be involved in the interaction with other proteins. Homology search using the NCBI database showed that ALEX1 shares significant homology with uncharacterized KIAA0512, KIAA0443, and THC257925 corresponding to an open reading frame consisting of several ESTs. The genes encoding ORF KIAA0512 and ORF based on THC257925 are named as ALEX2 and ALEX3, correspondingly. Comparative amino acid sequence analysis allowed the inventors to conclude that ALEX1, ALEX2, ALEX3, and, probably, KIAA0443 constitute a separate previously unidentified family of proteins. The genes for all four members of the family are located at the same region on chromosome X suggesting that these four ALEX genes evolved as a result of amplification and divergence of a common ancestral gene related to classical members of Arm repeat family of proteins.

Although overall homology of ALEX1 protein to other members of the Arm-repeat family of proteins is insignificant, the region that spans Arm repeats in ALEX1 is highly homologous to corresponding parts of importin-α and yeast Vac8p and to a less extent to segments in armadillo, β-catenin, and plakoglobin Importin-α (α-karyopherin), which is known as a nuclear localization signal sequence receptor, is involved in nuclear transport of proteins. It is known that yeast's Vac8p is involved in vacuole inheritance from mother cells to daughter cells (Wang, Y.-X. et al. (1998) J. Cell Biol. 140, 1063-1074). It may also be an essential component of the cytoplasm-to-vacuole targeting pathway as Vac8p mutant yeast cells are defective in targeting of aminopeptidase I from the cytoplasm to the vacuole. Interestingly, Vac8p protein is usually myristoylated in vivo (Wang, Y.-X. et al. (1998) J. Cell Biol. 140, 1063-1074). Likewise, ALEX1 contains four putative myristoylation sites close to the N-terminus. ALEX1 protein may be involved in targeting cytosolic proteins into membrane-enclosed cell compartments in a manner similar to Vac8p.

Recent studies established that several members of Arm repeat family including p0071, β-, γ-, and δ-catenins bind to presenilin-1 (PS1) Alzheimer's disease-linked PS1 mutations result in increased production of the longer form of amyloid β peptide. New findings suggested that PS1 regulates γ-secretase cleavage of APP or is itself a γ-secretase (De Strooper, B. et al. (1998) Nature 391, 387-390; Wolfe, M. S. et al. (1999) Nature 398, 513-517). In this invention, the present inventors demonstrate that IDE interacts with ALEX 1 in vitro. Further, it is shown that ALEX1 can interact with PS1. Thus, ALEX1 protein could serve as an adapter protein for IDE to bring the protease into close proximity to PS1 and, therefore, to the site of amyloid β peptide production. Interestingly, PS1 mutations, which cause Alzheimer's disease, do not abolish its binding to Arm repeat proteins (Zhang, Z. et al. (1998) Nature 395, 698-702). It is considered that if ALEX1 forms a complex with PS1, then mutations in ALEX1 or its reduced expression may disrupt or weaken the complex formation to contribute to the pathology. In this connection, recent full genome scan for a causative gene of late onset Alzheimer's disease identified amongst several candidate gene loci, a susceptibility locus in the region of X-chromosome (Kehoe et al. (1999) Hum. Mol. Genet. 8, 237-245) where ALEX1 is mapped, and another susceptibility locus in the long arm region of chromosome 10 (Bertram et al. (2000) Science, 290, 2302-2303, Ertekin-Taner et al. (2000) ibid, 2303-2304, Myers et al. (2000) ibid, 2304-2305) where IDE is mapped. By analogy with functions of β-catenin and other members of Arm repeat family, it is suggested that ALEX1 may bind to presenilin-1 (PS1) through armadillo repeats in normal brain tissues, introduce IDE into the site of amyloid β peptide production to contribute to the degradation of amyloid β peptide, and regulate the accumulation of amyloid β peptide.

Therefore, the ALEX1 protein can be a target molecule for preventing or treating Alzheimer's disease, screening for drugs using the ALEX1 gene. Thus, ALEX1 protein enables the development of novel therapeutic agents for Alzheimer's disease, and in addition, by detecting the expression of ALEX, it enables the diagnosis and testing of Alzheimer's disease.

Expression studies demonstrated that ALEX1 is expressed in almost all human tissues, except leukocytes (FIG. 4). The highest expression was revealed in the heart, skeletal muscle, brain, ovary, and prostate. It was barely detectable in liver and thymus. ALEX1 was expressed in all regions of the human brain tested. The lack of ALEX1 expression only in peripheral blood leukocytes suggests that this protein might be involved in signal transduction mediated by some sort of intercellular adhesion or establishment of cell polarity. Indeed, of all tissues examined, only leukocytes exist as single cells and only leukocytes lack any long-term established polarity and display highest motility. On the other hand, tissues with maximal ALEX1 expression, brain, heart, and skeletal muscle, consist of cells with the most striking polarized organization of any cell type in the body.

Mouse ortholog of ALEX1 is developmentally regulated with significant induction between days of 7 and 11 of embryo development (FIG. 8). This period in the development is associated with early organogenesis suggesting that ALEX1 might be involved in the morphogenesis and/or specification of embryonic patterning as another Arm repeat protein β-catenin, a component of Wnt-signaling pathway.

ALEX1 and ALEX2 showed remarkably similar expression patterns Like ALEX1, ALEX2 protein contains an N-terminal transmembrane domain with a most likely targeting to the endoplasmic reticulum membrane. The most striking finding is significantly reduced or undetectable expression of ALEX1 and ALEX2 in human tumors and tumor-derived cell lines (FIGS. 5, 6, and 7). In this invention, the inventors demonstrated that ALEX1 and ALEX2 transcripts are lost or reduced in cell lines derived from human carcinomas, but not from neuroblastomas, glioblastomas, or sarcomas. Carcinomas, the cancers of epithelial tissues, represent about 70% of all human tumors. The fact that ALEX1 and ALEX2 expression is impaired in carcinomas of multiple tissues suggests that these proteins are general factors involved in regulation of normal cell growth. Very similar expression patterns in normal and cancer tissues indicate that both genes are under the control of the same transcription factors.

Expression of ALEX1 and ALEX2 mRNA is lost or significantly reduced in human carcinoma samples and in cell lines established from various human carcinomas. These genes are however normally expressed in cell lines derived from other types of human tumors, i.e. sarcomas, neuroblastomas, and gliomas. Based on these findings, the present invention provides novel methods for diagnosing epithelial tumors using, as an index, the presence or absence of mutations in ALEX1 and ALEX2 genes, or reduced expression thereof. Cancer may be prevented or treated by using drugs regulating the expression of ALEX1 gene, or the activity of ALEX1 protein.

In order to gain insight into ALEX1's physiological role, the present inventors employed the yeast two-hybrid screen to identify potential ALEX1-interacting proteins. Thereby, the inventors identified a group of three overlapping clones derived from cDNA for JNK interacting protein-1 (JIP-1). JIP-1 is a recently cloned scaffold protein for the components of JNK signaling pathway: MLK3 (MAPKKK)->MKK7 (MAPKK)->JNK (MAPK). JIP-1 facilitates signaling by the bound protein kinases (Whitmarsh, A. J. et al. (1998) Science 281, 1671-1674). MKK7 is a major activator for JNK in the TNFα-stimulated pathway and in osmotically shocked cells. The inventors utilized c-Jun-dependent reporter gene system to analyze in vivo effect of ALEX1 on c-Jun-dependent transcriptional activation. As a result, expression of ALEX1 markedly inhibited c-Jun-dependent transcriptional activation in a dose-dependent manner Studies with various JIP-1 deletion mutants established that the binding site for ALEX1 on JIP-1 overlaps with the reported MKK7-binding domain, but not JNK and MLK3. Therefore, ALEX1 might negatively regulate JNK signaling cascade by competitively inhibiting the binding of MKK7 and the scaffold protein JIP-1. In this scenario, since ALEX1 inhibits the step of MKK7, the signal transduction from upstream component of the cascade, MLK3, to downstream effector, JNK, will be interrupted. This negative regulation disappears in cancer cells where the expression of ALEX1 is reduced or lost, and thus, c-Jun as well as JNK may be activated, contributing to tumorigenesis.

Furthermore, as a result of screening for proteins that interact with ALEX1 using yeast two-hybrid screening that uses ALEX1 lacking the transmembrane domain at the N-terminus(amino acid numbers 1 to 27) as a bait, the present inventors found that p0071 (plakophilin-4), SART-1, MSP58, ATRX, CSA2 (RED protein), p68 (RNA helicase/ATPase), OS-9, ZNF189, KIAA1221, α-Actinin4, and ZIP kinase interact with the above-mentioned ALEX1 protein lacking the N-terminal transmembrane domain.

By using these activities of the ALEX1 protein as indexes to screen for compounds that regulate the activity of the ALEX1 protein, drugs effective for the prevention and treatment of cancer and Alzheimer's disease can be obtained.

That is, the ALEX1 protein of this invention and the gene encoding this protein are thought to be useful as indexes for testing diseases such as cancer and Alzheimer's disease, as tools to elucidate the pathological mechanism of these diseases, and furthermore, as targets for developing pharmaceutical agents against these diseases.

This invention relates to a novel "ALEX1" protein, a gene encoding this protein, and production and use thereof, and more specifically relates to, (1) a DNA encoding a protein having an armadillo repeat structure, wherein the DNA is selected from the group consisting of:

(a) a DNA encoding a protein comprising the amino acid sequence of SEQ ID NO:3,
(b) a DNA comprising a coding region of the nucleotide sequence of SEQ ID NO:1 or 2,
(c) a DNA encoding a protein in which one or more amino acids of the amino acid sequence of SEQ ID NO:3 has been substituted, deleted, inserted, and/or added, and
(d) a DNA that hybridizes under stringent conditions to a DNA comprising the nucleotide sequence of SEQ ID NO:1 or 2, (2) a DNA encoding a protein that binds to a protein selected from the group consisting of insulin-degrading enzyme (IDE), presenilin-1 (PS-1), p0071 (plakophilin-4), SART-1, MSP58, ATRX, CSA2 (RED protein), p68 (RNA helicase/ATPase), OS-9, ZNF189, KIAA1221, α-Actinin4, and ZIP kinase, wherein the DNA is selected from the group consisting of:

(a) a DNA encoding a protein comprising the amino acid sequence of SEQ ID NO:3,
(b) a DNA comprising a coding region of the nucleotide sequence of SEQ ID NO:1 or 2,
(c) a DNA encoding a protein in which one or more amino acids of the amino acid sequence of SEQ ID NO:3 has been substituted, deleted, inserted, and/or added, and
(d) a DNA that hybridizes under stringent conditions to a DNA comprising the nucleotide sequence of SEQ ID NO:1 or 2, (3) a DNA encoding a protein that binds to JNK interacting protein 1 (JIP-1), wherein the DNA is selected from the group consisting of:

(a) a DNA encoding a protein comprising the amino acid sequence of SEQ ID NO:3,
(b) a DNA comprising a coding region of the nucleotide sequence of SEQ ID NO:1 or 2,
(c) a DNA encoding a protein in which one or more amino acids of the amino acid sequence of SEQ ID NO:3 has been substituted, deleted, inserted, and/or added, and
(d) a DNA that hybridizes under stringent conditions to a DNA comprising the nucleotide sequence of SEQ ID NO:1 or 2, (4) the DNA of (3) that encodes a protein that inhibits c-Jun-dependent transcription,
(5) a DNA encoding a partial peptide of a protein comprising the amino acid sequence of SEQ ID NO:3,
(6) a protein or peptide encoded by the DNA of any one of (1) to (5),
(7) a vector into which the DNA of any one of (1) to (5) has been inserted,
(8) a host cell carrying the DNA of any one of (1) to (5) or the vector of (7),
(9) a method of producing the protein or peptide of (6), the method comprising the steps of cultivating the host cell of (8) and collecting the expressed protein from the host cell or culture supernatant thereof,
(10) an antibody that binds to the protein of (6),
(11) a polynucleotide comprising at least 15 nucleotides complementary to a DNA comprising the nucleotide sequence of SEQ ID NO:1 or 2, or to complementary strand thereof,
(12) a polynucleotide comprising at least 15 nucleotides complementary to the DNA of any one of (1) to (4) or to complementary strand thereof, wherein the polynucleotide is used for testing Alzheimer's disease or cancer,
(13) a method of screening for a compound that binds to the protein of (6), the method comprising the steps of,
(a) contacting a test sample with the protein or partial peptide thereof, (b) detecting binding activity between the test sample and the protein or partial peptide thereof, and
(c) selecting a compound that binds to the protein or partial peptide thereof,
(14) a method of screening for a compound that regulates the expression of the DNA of any one of (1) to (4), the method comprising the steps of,
(a) contacting a test sample with a cell that endogenously expresses the DNA,
(b) detecting the expression, and
(c) selecting a compound that promotes or inhibits the expression compared to when the cell is not contacted with the test sample,
(15) a method of screening for a compound that regulates the expression of the DNA of any one of (1) to (4), the method comprising the steps of,
(a) contacting a test sample with a cell into which a vector having a reporter gene operably linked downstream of an endogenous transcription regulatory sequence of the DNA of any one of (1) to (4) has been introduced,
(b) detecting expression of the reporter gene within the cell, and
(c) selecting a compound that promotes or inhibits expression of the reporter gene compared to when the cell is not contacted with the test sample,
(16) a method of screening for a compound that regulates binding between a protein encoded by the DNA of (2) and a protein selected from the group consisting of insulin-degrading enzyme (IDE), presenilin-1 (PS-1), p0071 (plakophilin-4), SART-1, MSP58, ATRX, CSA2 (RED protein), p68 (RNA helicase/ATPase), OS-9, ZNF189, KIAA1221, α-Actinin4, and ZIP kinase, wherein the method comprises the steps of,
(a) contacting a protein encoded by the DNA of (2) with a protein selected from the group consisting of insulin-degrading enzyme (IDE), presenilin-1 (PS-1), p0071 (plakophilin-4), SART-1, MSP58, ATRX, CSA2 (RED protein), p68 (RNA helicase/ATPase), OS-9, ZNF189, KIAA1221, α-Actinin4, and ZIP kinase, in the presence of a test sample,
(b) detecting binding of these proteins, and
(c) selecting a compound that promotes or inhibits binding of these proteins compared to when detected in the absence of the test sample,
(17) a method of screening for a compound that regulates the binding between a protein encoded by a DNA of (3) and JIP-1 protein, wherein the method comprises the steps of,
(a) contacting the protein encoded by the DNA of (3) with JIP-1 protein in the presence of a test sample,
(b) detecting the binding of these proteins, and
(c) selecting a compound that promotes or inhibits the binding of these proteins compared to when the detection is performed in the absence of the test sample,
(18) a method of screening for a compound that regulates the activity of a protein encoded by a DNA of (3), wherein the method comprises the steps of,
(a) contacting a test sample with a cell expressing the protein encoded by the DNA of (3),
(b) detecting MKK7/JNK-mediated signal transduction in the cell, and
(c) selecting a compound that promotes or inhibits the signal transduction,
(19) the method of (18), wherein the MKK7/JNK-mediated signal transduction is detected using c-Jun-dependent transcription as an index in step (b),
(20) a compound that can be isolated by the method of any one of (13) to (19),
(21) a pharmaceutical composition comprising the compound of (20) as an active ingredient,
(22) the pharmaceutical composition of (21) for preventing or treating Alzheimer's disease or cancer,
(23) a method for testing Alzheimer's disease or cancer, the method comprising the step of detecting the expression level of DNA encoding the protein of (6) in a patient-derived test sample,
(24) the method of (23), wherein the expression level of the DNA is detected by a method comprising the steps of,
(a) contacting the polynucleotide of (12) with a patient-derived RNA sample, and
(b) detecting the binding of the polynucleotide to the RNA sample,
(25) the method of (24), wherein the expression level of the DNA is detected by a method comprising the steps of,
(a) synthesizing cDNA from a patient-derived RNA sample,
(b) performing polymerase chain reaction using the synthetic cDNA as template and the polynucleotide of (12) as a primer, and
(c) detecting DNA amplified by polymerase chain reaction,
(26) a method for testing Alzheimer's disease or cancer, wherein the method comprises the step of detecting the level of the protein of (6) present in a patient-derived test sample,
(27) the method of (26), wherein the level of protein present is detected by a method comprising the steps of,
(a) contacting the antibody of (10) with a patient-derived protein sample, and
(b) detecting the binding of the antibody to the protein sample,
(28) a method for testing Alzheimer's disease or cancer, the method comprising detecting a mutation in DNA encoding the protein of (6),
(29) the method for testing Alzheimer's disease or cancer of (28), the method comprising the steps of determining the nucleotide sequence of DNA encoding the protein of (6) and comparing it with the sequence of a healthy person,
(30) the method of (29), wherein the mutation is detected by a method comprising the steps of,
(a) preparing a DNA sample from a patient,
(b) amplifying the patient-derived DNA using the polynucleotide of (12) as a primer,
(c) cleaving the amplified DNA,
(d) separating the DNA fragments according to their size,
(e) hybridizing the polynucleotide of (12) that has a detectable label as a probe to the separated DNA fragments, and
(f) comparing the detected DNA fragment size to a control from a healthy person,
(31) the method of (29), wherein the mutation is detected by a method comprising the steps of,
(a) preparing an RNA sample from a patient,
(b) separating the prepared RNA according to size,
(c) hybridizing the polynucleotide of (12) that has a detectable label as a probe to the separated RNA, and
(d) comparing the detected RNA size to a control from a healthy person,
(32) the method of (29), wherein the mutation is detected by a method comprising the steps of,
(a) preparing a DNA sample from a patient,
(b) amplifying the patient-derived DNA using the polynucleotide of (12) as a primer, (c) dissociating the amplified DNA into single stranded DNA, (d) separating the dissociated single stranded DNA on a non-denaturing gel, and (e) comparing the mobility of the separated single stranded DNA on the gel with that of a control from a healthy person,

(33) the method of (29), wherein the mutation is detected by a method comprising the steps of, (a) preparing a DNA sample from a patient, (b) amplifying the patient-derived DNA using the polynucleotide of (12) as a primer, (c) separating the amplified DNA on a gel in which DNA denaturant concentration gradually rises, and (d) comparing the mobility of the separated DNA on the gel with that of a control from a healthy person,

(34) a method for testing Alzheimer's disease or cancer, the method comprising detecting a mutation in the protein of (6),

(35) the method of (34), wherein the mutation is detected using the binding activity with a protein selected from the group consisting of IDE, PS-1, JIP-1, p0071 (plakophilin-4), SART-1, MSP58, ATRX, CSA2 (RED protein), p68 (RNA helicase/ATPase), OS-9, ZNF189, KIAA1221, α-Actinin4, and ZIP kinase as an index,

(36) a testing reagent for Alzheimer's disease or cancer, comprising the antibody of (10), and

(37) a testing reagent for Alzheimer's disease or cancer, comprising the polynucleotide of (12).

This invention relates to a gene "ALEX1" encoding a novel armadillo repeat-containing protein. The nucleotide sequences of human-derived ALEX1 cDNA are shown in SEQ ID NOS: 1 and 2, and the amino acid sequence of the protein encoded by these cDNA is shown in SEQ ID NO:3. As SEQ ID NOS: 1 and 2 indicate, human ALEX1 cDNA has an ORF encoding a protein comprising 453 amino acids. Since human ALEX1 protein of this invention binds to IDE, and interacts with presenilin-1, it is thought to be involved with the onset of Alzheimer's disease.

In addition, by Northern blotting and RT-PCR analysis, expression of human ALEX1 gene was observed in various tissues, and was especially high in the ovary, heart, testis, prostate, brain, spleen, skeletal muscle, and colon, and in contrast, expression was weak in the liver and thymus. Also, mRNA expression in the peripheral leukocytes was at or below the detection limit Also, as a result of analyzing expression of ALEX1 using cancer cells and cancer tissues, it was elucidated that expression of ALEX1 is significantly reduced in epithelial cancer. Therefore, by testing the expression of ALEX1 of this invention, it is possible to test for cancer.

Furthermore, this invention includes proteins functionally equivalent to human "ALEX1" protein (SEQ ID NO:3). Such proteins include, for example, mutants of human "ALEX1" protein and homologues of organisms other than human. Such proteins include for example, proteins having an armadillo repeat structure. Whether a protein has an armadillo repeat structure can be determined through analysis by Pfam algorithm (Bateman, A. et al., Nucleic Acids Research 27:260-262 (1999)) using the obtained amino acid sequence as a query.

Analysis by Pfam can be performed for example, by using the system at Sanger centre (located on the World Wide Web at: sanger.ac.uk/Software/Pfam/search.shtml). The cutoff value for E-value is set at 20. If the E-value is 20 or less (at higher precision, 15 or less), the amino acid sequence of the searched protein is determined to have an armadillo repeat structure. For example, for ALEX1 (SEQ ID NO:3), the first arm repeat (amino acid numbers 193 to 235) is detected at E-value=11 and the second arm repeat is detected at E-value=2.1. Similarly, for KIAA0152 (ALEX2) and ALEX3, one arm repeat is detected at amino acid numbers 416 to 457 (E-value=0.56) and at amino acid numbers 151 to 192 (E-value=9.3), respectively. Also, in an analysis performed on ProfileScan Server, one arm repeat is detected at a normalized score of 8.802 at amino acid numbers 247 to 284 of ALEX1, and the obtained result is a significant match.

In addition, proteins functionally equivalent to the human "ALEX1" protein (SEQ ID NO:3), include a protein that has an activity to bind to insulin-degrading enzyme (IDE) protein (Kurochkin, I. V., and Goto, S. (1994) FEBS Lett. 345, 33-37; McDermott, J. R., and Gibson, A. M. (1997) Neurochem. Res. 22, 49-56; Qiu, W. Q. et al. (1998) J. Biol. Chem. 273, 32730-32738).

The binding activity of a certain protein with an IDE protein can be detected with high sensitivity, for example, by immunoprecipitation of the IDE protein by an anti-IDE antibody, or precipitation of IDE to which a specific tag has been added by an anti-tag antibody, and when detecting the co-precipitating protein, a tag is added to the target protein, and detection can be made by an antibody against this tag, or by using a specific antibody against the target protein. Other methods for detecting the binding activity with the IDE protein include pull-down method, which does not use antibodies and analyzes proteins adsorbed by mixing IDE bound to beads with a cell extract solution. Alternatively, a method that directly observes the binding by BIAcore, and furthermore, a method that functionally observes the binding in a living cell by Two-Hybrid method can also be used.

For the IDE protein used above, a wild type protein may be used, but an IDE protein to which mutations have been introduced may also be used. For example, H108Q mutation shown in Examples maintains substrate binding activity of IDE protein while destroying protease activity. By introducing this mutation, when binding assay is performed within yeast cells and such, cytotoxic activity of the IDE protein toward host cells can be removed, and when a protein bound to IDE is the substrate of IDE, bond breakage upon dissociation can be avoided. Therefore, for a more stable detection of binding, it is considered preferable to use H108Q. Also, as long as proteins binding to IDE can be detected stably, other mutant IDE proteins may be used.

In addition, as proteins functionally equivalent to human "ALEX1" protein (SEQ ID NO:3), proteins having activity to bind to presenilin-1 protein (Kimberly, W T et al. J. Biol. Chem. 2000, 275 (5) 3173-8; Selkoe, D J. Trends Cell Biol. 1998, 8, 447-453) are included. Furthermore, proteins having activity to bind to JNK interacting protein 1 (JIP-1) (Whitmarsh, A. J. et al. (1998) Science 281, 1671-1674) are included. Whether or not there is a binding activity with the PS-1 protein or the JIP-1 protein can be determined by immunoprecipitation, pull-down method, BIAcore, Two-Hybrid method, and such, similarly to the detection of the binding activity with the IDE protein mentioned above.

The protein of this invention having activity to bind to JIP-1 preferably has the activity to inhibit c-Jun-dependent transcription. Whether or not there is an activity to inhibit c-Jun-dependent transcription or not can be determined for example, as indicated in Examples, by using a c-Jun-dependent luciferase reporter construct, and by transfecting a vector expressing the test protein of interest with MEKK1 expression vector for example, and whether the activation of c-Jun-dependent transcription by MEKK1 is inhibited by the test protein or not can be determined using expression of the reporter gene as an index.

Furthermore, proteins functionally equivalent to human "ALEX1" protein (SEQ ID NO:3) include proteins having activity to bind to the proteins selected from the group consisting of p0071 (plakophilin-4), SART-1, MSP58, ATRX, CSA2 (RED protein), p68 (RNA helicase/ATPase), OS-9, ZNF189, KIAA1221, α-Actinin4, and ZIP kinase. Whether or not there is a binding activity with these proteins can be determined by immunoprecipitation, pull-down method, BIAcore, Two-Hybrid method, and such, similarly to the detection of binding activity with the IDE protein mentioned above. Examples of these proteins are, specifically, proteins encoded by the genes shown below.

p0071 (plakophilin-4): Arm repeat-containing presenilin-binding protein

GenBank Ac. No. X81889; *H. sapiens* mRNA for p0071 protein, GenBank Ac. No. NM_003628; *Homo sapiens* plakophilin 4 (PKP4), mRNA SART-1: human squamous cell carcinoma antigen, expressed in growing cells only GenBank Ac. No. AB006198; *Homo sapiens* mRNA for SART-1, GenBank Ac. No. Y14314; *Homo sapiens* mRNA for IgE autoantigen MSP58: nucleoprotein, interacting to the growth-related nucleoprotein p120, expressed in growing cells only GenBank Ac. No. AF015308; *Homo sapiens* nucleolar protein (MSP58) mRNA, GenBank Ac. No. AF068007; *Homo sapiens* cell cycle-regulated factor p78 mRNA ATRX: murine colon adenocarcinoma antigen, cell cycle-dependently phosphorylated, a helicase/ATPase member of the SNF2 family GenBank Ac. No. U72938; *Homo sapiens* putative DNA dependent ATPase and helicase (ATRX) mRNA, alternatively spliced product 3, GenBank Ac. No. NM_000489; *Homo sapiens* alpha thalassemia/mental retardation syndrome X-linked (RAD54 (*S. cerevisiae*) homolog) (ATRX), mRNA CSA2 (RED protein): chondrosarcoma-associated protein, distributed in nuclei as dots, transcription-related function?

GenBank Ac. No. AF182645; *Homo sapiens* chondrosarcoma-associated protein 2 (CSA2) mRNA p68: RNA helicase/ATPase GenBank Ac. No. X52104; Human mRNA for p68 protein, GenBank Ac. No. NM_004396; *Homo sapiens* DEAD/H (Asp-Glu-Ala-Asp/His) box polypeptide 5 (RNA helicase, 68 kD) (DDX5), mRNA OS-9: amplified in human sarcoma, containing nuclear localization signal GenBank Ac. No. NM_006812; *Homo sapiens* amplified in osteosarcoma (OS-9), mRNA ZNF189: $C_2H_2$ Zinc Finger protein GenBank Ac. No. AF025770; *Homo sapiens* $C_2H_2$ zinc finger protein (ZNF189) mRNA KIAA1221: $C_2H_2$ Zinc Finger protein GenBank Ac. No. AB033047; *Homo sapiens* mRNA for KIAA1221 protein, partial cds α-Actinin4: involved in actin polymerization, cell motility, and cancer infiltration GenBank Ac. No. NM_004924; *Homo sapiens* actinin, alpha 4 (ACTN4), mRNA ZIP kinase GenBank Ac. No. AB022341; *Homo sapiens* mRNA for ZIP kinase One method well known to those skilled in the art for preparing functionally equivalent proteins is to introduce mutations into proteins. For example, one skilled in the art can prepare proteins functionally equivalent to the human "ALEX1" protein by introducing appropriate mutations into the amino acid sequence of the protein (SEQ ID NO:3), by using site-specific mutagenesis (Hashimoto-Gotoh, T. et al. (1995) Gene 152, 271-275; Zoller, M J, and Smith, M. (1983) Methods Enzymol. 100, 468-500; Kramer, W. et al. (1984) Nucleic Acids Res. 12, 9441-9456; Kramer W, and Fritz H J (1987) Methods Enzymol. 154, 350-367; Kunkel, T A (1985) Proc Natl Acad Sci USA. 82, 488-492; Kunkel (1988) Methods Enzymol. 85, 2763-2766), and such. Mutation of amino acids may occur in nature, too. Furthermore, the proteins of the present invention include a protein comprising an amino acid sequence of the "ALEX1" protein (SEQ ID NO:3) in which one or more amino acids have been mutated, which is functionally equivalent to the ALEX1 protein. In such a mutant protein, the number of amino acids mutated are considered to be usually 100 residues or less, preferably 50 residues or less, more preferably 30 residues or less, even more preferably 10 residues or less (e.g. 5 residues or less).

It is preferable to mutate an amino acid residue into one that allows the properties of the amino acid side-chain to be conserved. Examples of properties of amino acid side chains include: hydrophobic amino acids (A, I, L, M, F, P, W, Y, V), hydrophilic amino acids (R, D, N, C, E, Q, G, H, K, S, T), and amino acids comprising the following side chains: aliphatic side-chains (G, A, V, L, I, P); hydroxyl group-containing side-chains (S, T, Y); sulfur atom-containing side-chains (C, M); carboxylic acid- and amide-containing side-chains (D, N, E, Q); base-containing side-chain (R, K, H); and aromatic-containing side-chains (H, F, Y, W)(The letters within parenthesis indicate the one-letter codes of amino acids). Proteins whose amino acids have been conservatively substituted are included in the proteins of this invention.

It is well known that a protein having a deletion, addition, and/or substitution of one or more amino acid residues in the sequence of the protein can retain the original biological activity (Mark D. F. et al. Proc. Natl. Acad. Sci. U.S.A. 81:5662-5666 (1984); Zoller M. J. and Smith M. Nucleic Acids Res. 10:6487-6500 (1982); Wang A. et al. Science 224:1431-1433 (1984); Dalbadie-McFarland G. et al. Proc. Natl. Acad. Sci. U.S.A. 79:6409-6413 (1982)).

A protein in which amino acid residues have been added to the amino acid sequence of the human "ALEX1" protein includes a fusion protein comprising the human "ALEX1" protein. The present invention includes a fusion protein in which the human "ALEX1" protein and one or more other proteins or peptides are fused. Methods well known in the art may be used to generate a fusion protein of the present invention. For example, DNA encoding the human "ALEX1" protein (SEQ ID NO:3) and DNA encoding another protein or peptide are linked in frame and introduced into an expression vector. The fusion protein is then expressed in a host cell. The protein or peptide fused to a protein of the present invention is not limited to any specific protein or peptide.

Known peptides, for example, FLAG (Hopp, T. P. et al., Biotechnology (1988) 6, 1204-1210), 6× His containing six His (histidine) residues, 10× His, Influenza agglutinin (HA), human c-myc fragment, VSV-GP fragment, p18HIV fragment, T7-tag, HSV-tag, E-tag, SV40T antigen fragment, lck tag, α-tubulin fragment, B-tag, Protein C fragment, and such, can be used as peptides that are fused to a protein of the present invention. Examples of proteins that are fused to a protein of the invention are, GST (glutathione-S-transferase), Influenza agglutinin (HA), immunoglobulin constant region, β-galactosidase, MBP (maltose-binding protein), and such. Fusion proteins can be prepared by fusing commercially available DNA encoding these peptides or proteins with DNA encoding a protein of the present invention and expressing the fused DNA prepared.

An alternative method known to those skilled in the art for preparing functionally equivalent proteins is, for example, the method utilizing the hybridization technique (Sambrook, J. et al., Molecular Cloning 2nd ed. 9.47-9.58, Cold Spring Harbor Lab. Press, 1989). Generally, one skilled in the art can isolate DNA highly homologous to the whole or part of a DNA sequence encoding the human "ALEX1" protein (SEQ ID NO:1 or 2), and then isolate a protein functionally equivalent to the human "ALEX1" protein from those DNA isolated. The present invention includes proteins encoded by DNA that hybridize with the whole or part of DNA encoding the human "ALEX1" protein, in which the proteins are functionally equivalent to the human "ALEX1" protein. These proteins include homologues of nonhuman mammal (e.g. proteins encoded by genes of monkeys, mice, rats, rabbits, and cattle). Also, since the ALEX genes form a family, it is possible to isolate other ALEX family genes using DNA encoding human "ALEX1" protein as probes and primers. For example, a probe or a primer can be constructed based on the amino acid sequence of ALEX1, particularly the 226 amino acid-long sequence from amino acid number 200 to the C-terminal end containing an Arm repeat, or a portion thereof. Thereafter, hybridization and amplification by PCR may be performed under an appropriate stringency. When isolating animal-derived cDNA highly homologous to DNA encoding human "ALEX1" protein, many tissues and cells, including ovary, heart, testis, prostate, brain, spleen, skeletal muscle, and colon, expected to express the protein of this invention may be used, but the source is not limited thereto.

Hybridization conditions for isolating DNA encoding a protein functionally equivalent to the human "ALEX1" protein may be appropriately selected by a person skilled in the art. A stringent hybridization condition is, for example, washing in 42° C., 2×SSC, 0.1% SDS, after hybridization, and preferably, in 50° C., 2×SSC, 0.1% SDS. More preferably, for example, washing is conducted in 65° C., 2×SSC, 0.1% SDS. Under these conditions, the higher the temperature, the higher the homology of the obtained DNA will be. However, several factors, such as temperature and salt concentration, can influence the stringency of hybridization and one skilled in the art can suitably select the factors to accomplish a similar stringency.

In place of hybridization, a gene amplification method using primers synthesized based on the sequence information of the DNA (SEQ ID NO:1 or 2) encoding the human "ALEX1" protein, for example, the polymerase chain reaction (PCR) method, can be utilized.

A protein functionally equivalent to the human "ALEX1" protein encoded by the DNA isolated through the above hybridization technique or gene amplification techniques normally has a high homology to the amino acid sequence of the human "ALEX1" protein (SEQ ID NO:3). The proteins of the present invention also include proteins that are functionally equivalent to the human "ALEX1" protein and are highly homologous to the amino acid sequence shown in SEQ ID NO:3. "Highly homologous" refers to, normally an identity of at least 60% or higher, preferably 75% or higher, more preferably 90% or higher, and even more preferably 95% or higher, at the amino acid level. The homology of a protein can be determined by following the algorithm in "Wilbur, W. J. and Lipman, D. J. (1983) Proc. Natl. Acad. Sci. USA 80:726-730".

The proteins of the present invention may have variations in the amino acid sequence, molecular weight, isoelectric point, the presence or absence of sugar chains, form, and so on, depending on the cell or host used to produce it or the purification method utilized (described below). Nevertheless, as long as the obtained protein has a function equivalent to the human "ALEX1" protein, it is within the scope of the present invention.

The proteins of the present invention can be prepared as recombinant proteins or naturally occurring proteins, using methods commonly known in the art. When the protein is a recombinant protein, it may be produced by inserting DNA (for example, DNA having the nucleotide sequence of SEQ ID NO:1 or 2) encoding a protein of the present invention into an appropriate expression vector, collecting the transformant obtained by introducing the vector into an appropriate host cell, obtaining an extract, and then purifying and preparing the protein using ion exchange, reverse phase, gel filtration, or affinity chromatography. Affinity chromatography may be done using a column in which an antibody against a protein of the present invention is immobilized. A combination of such columns may also be used.

Alternatively, when a protein of the invention is expressed in host cells (e.g., animal cells or $E.\ coli$) as a fusion protein with glutathione S transferase protein, or a recombinant protein with multiple histidine residues, the expressed recombinant protein can be purified using a glutathione column or nickel column. After the fusion protein is purified, if necessary, regions of the fusion protein (apart from the desired protein) can be digested and removed with thrombin, factor Xa, etc.

The native protein of the invention can be isolated by methods well known in the art, for example, purifying an extract of tissues or cells that express a protein of the invention with an affinity column to which an antibody binding to a protein of the present invention described below is bound. The antibody may be a polyclonal or monoclonal antibody.

The present invention also includes partial peptides of the proteins of the present invention. The partial peptides of the present invention comprise at least 7 or more amino acids, preferably 8 or more amino acids, more preferably 9 or more amino acids. The partial peptides can be used, for example, for generating antibodies against a protein of the present invention, screening of compounds binding to a protein of the present invention, or screening of stimulators or inhibitors of a protein of the present invention. Additionally, they may be antagonists or competitive inhibitors of the proteins of the present invention. The partial peptides of the proteins of the present invention include those that include, for example, functional domains of the human "ALEX1" protein (SEQ ID NO:3). Such functional domains include, for example, the Arm domain. A partial peptide containing one or more Arm domains (Arm1 and/or Arm2) (see FIG. 2) is included in the partial peptides of the present invention. In addition, a partial protein of "ALEX1" in which the transmembrane domain has been deleted (e.g. a protein without $1^{st}$ to $27^{th}$ amino acids) may also be included. The partial peptides of the present invention can be produced by genetic engineering methods, known peptide synthesis methods, or by cutting the proteins of the present invention by appropriate peptidases. Synthesis of the peptides may be conducted according to, for example, the solid phase synthesis method, or the liquid phase synthesis method.

In addition to being utilized in the above-described in vivo or in vitro production of a protein of the present invention, DNA encoding a protein of the present invention may also be applied, for example, in the gene therapy of diseases caused by an aberration in a gene encoding a protein of the present invention or diseases treatable by a protein of the present invention. Any type of DNA, such as cDNA synthesized from mRNA, genomic DNA, or synthetic DNA can be used so long as the DNA encodes a protein of the present invention. Also as long as they can encode a protein of the present invention, DNA comprising arbitrary sequences based on the degeneracy of the genetic code are also included.

The DNA of the present invention can be prepared by using methods known in the art. For example, a cDNA library can be constructed from cells expressing a protein of the present invention and hybridization can be conducted using a part of the DNA sequence of the present invention (for example, SEQ ID NO:1 or 2) as a probe. The cDNA library may be prepared, for example, according to the method described by Sambrook J. et al. (Molecular Cloning, Cold Spring Harbor Laboratory Press (1989)), or instead, commercially available cDNA libraries may be used. Alternatively, DNA of the present invention can be obtained by preparing RNA from cells expressing a protein of the present invention, synthesizing cDNA by using a reverse transcriptase, synthesizing oligo-DNA based on a DNA sequence of the present invention (for example, SEQ ID NO:1 or 2), and amplifying the cDNA encoding a protein of the present invention by PCR using the oligo-DNA as primers.

The nucleotide sequence of the obtained cDNA is determined to find an open reading frame, and thereby, the amino acid sequence of a protein of the invention can be obtained. The cDNA obtained may also be used as a probe for screening a genomic library to isolate genomic DNA. Similarly, endogenous transcriptional regulators of genes encoding proteins of this invention can be obtained.

More specifically, mRNA may first be isolated from a cell, tissue, or organ in which a protein of the invention is expressed (e.g. tissues such as ovary, heart, testis, prostate, brain, spleen, skeletal muscle, and colon). Known methods can be used to isolate mRNA; for instance, total RNA is prepared by guanidine ultracentrifugation (Chirgwin J. M. et al. Biochemistry 18:5294-5299 (1979)) or AGPC method (Chomczynski P. and Sacchi N. Anal. Biochem. 162:156-159 (1987)), and mRNA is purified from total RNA using an mRNA Purification Kit (Pharmacia) and such. Alternatively, mRNA may be directly prepared by QuickPrep mRNA Purification Kit (Pharmacia).

The obtained mRNA is used to synthesize cDNA using reverse transcriptase. cDNA may be synthesized by using a kit such as the AMV Reverse Transcriptase First-strand cDNA Synthesis Kit (Seikagaku Kogyo). Alternatively, cDNA may be synthesized and amplified following the 5'-RACE method or 3'-RACE method (Frohman M. A. et al. Proc. Natl. Acad. Sci. U.S.A. 85:8998-9002 (1988); Belyaysky A. et al. Nucleic Acids Res. 17:2919-2932 (1989)) that uses primers and such described herein, the 5'-Ampli FINDER RACE Kit (Clontech), and polymerase chain reaction (PCR).

A desired DNA fragment is prepared from the PCR products and linked to vector DNA. The recombinant vector is used to transform E. coli and such, and the desired recombinant vector is prepared from a selected colony. The nucleotide sequence of the desired DNA can be verified by conventional methods, such as dideoxynucleotide chain termination.

DNA of the invention may be designed to have a sequence that is expressed more efficiently by taking into account the frequency of codon usage in the host used for expression (Grantham R. et al. Nucleic Acids Res. 9:43-74 (1981)). The DNA of the present invention may be altered by a commercially available kit or a conventional method. For instance, the DNA may be altered by digestion with restriction enzymes, insertion of a synthetic oligonucleotide or an appropriate DNA fragment, addition of a linker, or insertion of the initiation codon (ATG) and/or the stop codon (TAA, TGA, or TAG), etc.

Specifically, the DNA of the present invention include DNA having the following nucleotide sequences: from A at position 372 to C at position 1730 of SEQ ID NO:1, and from A at position 364 to C at position 1722 of SEQ ID NO:2.

Furthermore, the DNA of the present invention include DNA capable of hybridizing with DNA having the nucleotide sequence of SEQ ID NO:1 or 2, and encoding a protein functionally equivalent to a protein of the invention described above. Hybridization conditions may be appropriately chosen by one skilled in the art. Specifically, conditions described above may be used. Under the conditions, DNA having higher homologies can be obtained by increasing temperature. The above hybridizing DNA is preferably natural DNA, for example, cDNA or chromosomal DNA.

The present invention also provides a vector into which DNA of the present invention is inserted. The vectors of the present invention are useful in maintaining the DNA of the present invention within the host cell, or expressing a protein of the present invention.

When E. coli is used as the host cell, there is no limitation other than that the vector should have an "ori", to amplify and mass-produce the vector in E. coli (e.g., JM109, DH5α, HB101, or XL1Blue), and such, and a marker gene for selecting the transformed E. coli (e.g., a drug-resistance gene selected by a drug (e.g., ampicillin, tetracycline, kanamycin, or chloramphenicol)). For example, M13-series vectors, pUC-series vectors, pBR322, pBluescript, pCR-Script, and such can be used. Besides the vectors, pGEM-T, pDIRECT, pT7, and so on can also be used for the subcloning and excision of the cDNA as well. When a vector is used to produce a protein of the present invention, an expression vector is especially useful. When the expression vector is expressed, for example, in E. coli, it should have the above characteristics in order to be amplified in E. coli. Additionally, when E. coli, such as JM109, DH5α, HB101, or XL1-Blue, are used as the host cell, the vector should have a promoter, e.g. lacZ promoter (Ward E S et al. (1989) Nature 341:544-546; Ward E S et al. (1992) FASEB J. 6:2422-2427), araB promoter (Better M et al. (1988) Science 240:1041-1043), or T7 promoter, that can efficiently promote the expression of the desired gene in E. coli. Other examples of the vectors are pGEX-5X-1 (Pharmacia), "QIAexpress system" (QIAGEN), pEGFP, and pET (for this vector, BL21, a strain expressing T7 RNA polymerase, is preferably used as the host).

Further, the vector may comprise a signal sequence to secrete the polypeptide. For producing the protein into the periplasm of E. coli, the pelB signal sequence (Lei S. P. et al. J. Bacteriol. 169:4379 (1987)) may be used as the signal sequence for protein secretion. For example, the calcium chloride method or electroporation may be used to introduce the vector into host cells.

As vectors used to produce the proteins of the present invention, for example, expression vectors derived from mammals (e.g. pcDNA3 (Invitrogen), pEF-BOS (Mizushima, S, and Nagata, S, Nucleic Acids Res. (1990) 18:5322), pEF, pCDM8), insect cells (e.g. "Bac-to-BAC baculovirus expression system" (GIBCO-BRL), pBacPAK8), plants (e.g. pMH1, pMH2), animal viruses (e.g. pHSV, pMV, pAdexLcw), retroviruses (e.g. pZIPneo), yeasts (e.g. "*Pichia* Expression Kit" (Invitrogen), pNV11, SP-Q01), and *Bacillus subtilis* (e.g. pPL608, pKTH50) can be mentioned other than those for E. coli.

In order to express proteins in animal cells, such as CHO, COS, and NIH3T3 cells, the vector must have a promoter necessary for expression in such cells (e.g. SV40 promoter (Mulligan R C et al. (1979) Nature 277:108-114), MMLV-LTR promoter, EF1α promoter (Mizushima, S, and Nagata, S. (1990) Nucleic Acids Res. 18:5322), CMV promoter, etc.). It is more preferable if the vector additionally had a marker gene for selecting transformants (for example, a drug resistance gene selected by a drug (e.g., neomycin, G418, etc.)). Examples of vectors with such characteristics include pMAM, pDR2, pBK-RSV, pBK-CMV, pOPRSV, pOP13, and so on.

Furthermore, in order to stably express the gene and to amplify the copy number in cells, the method using CHO cells deficient in nucleic acid synthetic pathways as the host, incorporating into the CHO cells a vector (such as pCHOI) having a DHFR gene that compensates for the deficiency, and amplifying the vector with methotrexate (MTX) can be used. Furthermore, for transiently expressing a gene, the method that transforms COS cells that have the gene for SV40 T antigen on the chromosome with a vector (such as pcD) having the SV40 replication origin can be mentioned. The replication origin may be that of a polyomavirus, adenovirus, bovine papilloma virus (BPV), and the like. Further, to amplify the gene copy number in the host cells, selection markers such as the aminoglycoside transferase (APH) gene, thymidine kinase (TK) gene, E. coli xanthine-guanine phosphoribosyl transferase (Ecogpt) gene, and the dihydrofolate reductase (dhfr) gene may be comprised in the expression vector.

DNA of the present invention can be expressed in animals by, for example, inserting DNA of the invention into an appropriate vector and introducing the vector into a living body by the retrovirus method, liposome method, cationic liposome method, adenovirus method, and so on. Thus, it is possible to perform gene therapy of diseases caused by a mutation of the "ALEX1" gene of the present invention. The vectors used in these methods include, but are not limited to, adenovirus vectors (e.g. pAdexlcw), retrovirus vectors (e.g. pZIPneo), and so on. General techniques for gene manipulation, such as insertion of the DNA of the invention into a vector, can be performed according to conventional methods (Sambrook, J. et al. (1989) Molecular Cloning 2nd ed., 5.61-5.63, Cold Spring Harbor Lab. press). Administration to the living body may be performed according the ex vivo method or the in vivo method.

The present invention also provides a host cell into which a vector of the present invention has been introduced. The host cell into which the vector of the invention is introduced is not particularly limited. For example, E. coli, various animal cells, and such, can be used. The host cell of the present invention can be used, for example, as a production system to produce and express a protein of the present invention. Protein production systems include in vitro and in vivo systems. Such production systems using eukaryotic cells or prokaryotic cells can be given as in vitro production systems.

As eukaryotic host cells, for example, animal cells, plant cells, and fungi cells can be used. Mammalian cells, for example, CHO, COS, 3T3, myeloma, BHK (baby hamster kidney), HeLa, Vero, amphibian cells (e.g. platanna oocytes (Valle et al. (1981) Nature 291:358-340), and insect cells (e.g. Sf9, Sf21, Tn5) are known as animal cells. Among CHO cells, those deficient in the DHFR gene, dhfr-CHO (Urlaub, G. and Chasin, L. A. Proc. Natl. Acad. Sci. USA (1980) 77:4216-4220) and CHO K-1 (Kao, F. T. and Puck, T. T. Proc. Natl. Acad. Sci. USA (1968) 60:1275-1281), are particularly preferable. Among animal cells, CHO cells are particularly preferable for mass expression. A vector can be introduced into a host cell by, for example, the calcium phosphate method, the DEAE-dextran method, methods using cationic liposome DOTAP (Boehringer-Mannheim), electroporation, lipofection, etc.

As plant cells, for example, plant cells originating from Nicotiana tabacum are known as protein producing systems and may be used as callus cultures. As fungal cells, yeast cells such as Saccharomyces, including Saccharomyces cerevisiae, or filamentous fungi such as Aspergillus, including Aspergillus niger, are known.

Useful prokaryotic cells include bacterial cells. Bacterial cells such as E. coli, for example, JM109, DHSα, HB101, and such, as well as Bacillus subtilis are known.

These cells are transformed by desired DNA, and the resulting transformants are cultured in vitro to obtain the protein. Transformants can be cultured using known methods. For example, culture medium such as DMEM, MEM, RPMI1640, or IMDM may be used with or without serum supplements such as fetal calf serum (FCS) as culture medium for animal cells. The pH of the culture medium is preferably between about 6 and 8. Such cells are typically cultured at about 30 to 40° C. for about 15 to 200 hr, and the culture medium may be replaced, aerated, or stirred if necessary.

Animal and plant hosts may be used for in vivo production. For example, desired DNA can be introduced into an animal or plant host. Encoded proteins are produced in vivo, and then recovered. These animal and plant hosts are included in the "host" of the present invention.

Animals to be used for the production system described above include mammals and insects. Mammals such as goats, pigs, sheep, mice, and cattle may be used (Vicki Glaser, SPECTRUM Biotechnology Applications (1993)). Alternatively, the mammals may be transgenic animals.

For instance, desired DNA may be prepared as a fusion gene with a gene such as goat β casein gene that encodes a protein specifically produced into milk DNA fragments comprising the fusion gene are injected into goat embryos, which are then introduced back to female goats. Proteins are recovered from milk produced by the transgenic goats (i.e., those born from the goats that had received the modified embryos) or from their offspring. To increase the amount of milk containing the proteins produced by transgenic goats, appropriate hormones may be administered (Ebert K. M. et al. (1994) Bio/Technology 12:699-702).

Alternatively, insects, such as the silkworm, may be used. Baculoviruses into which DNA encoding a desired protein has been inserted can be used to infect silkworms, and the desired protein is recovered from the body fluid (Susumu M. et al. (1985) Nature 315:592-594).

As plants, for example, tobacco can be used. When using tobacco, DNA encoding a desired protein may be inserted into a plant expression vector, such as pMON 530, which is introduced into bacteria, such as Agrobacterium tumefaciens. Then, the bacteria is used to infect tobacco, such as Nicotiana tabacum, and the desired polypeptide is recovered from the leaves (Ma, J K et al. (1994) Eur. J. Immunol. 24:131-138).

A protein of the present invention obtained as above may be isolated from inside or outside of hosts (medium, etc.), and purified as a substantially pure homogeneous protein. The method for protein isolation and purification is not limited to any specific method; in fact, any standard method may be used. For instance, column chromatography, filters, ultrafiltration, salting out, solvent precipitation, solvent extraction, distillation, immunoprecipitation, SDS-polyacrylamide gel electrophoresis, isoelectric focusing, dialysis, and recrystallization may be appropriately selected and combined to isolate and purify the protein.

For chromatography, for example, affinity chromatography, ion-exchange chromatography, hydrophobic chromatography, gel filtration chromatography, reverse phase chromatography, adsorption chromatography, and such may be used (Strategies for Protein Purification and Characterization: A Laboratory Course Manual. Ed. Daniel R. Marshak et al., Cold Spring Harbor Laboratory Press (1996)). These chromatographies may be performed by liquid chromatographies such as HPLC and FPLC. Thus, the present invention provides highly purified proteins produced by the above methods.

A protein may be optionally modified or partially deleted by treating it with an appropriate protein-modifying enzyme before or after purification. For example, trypsin, chymotrypsin, lysylendopeptidase, protein kinase, glucosidase, and such are used as protein-modifying enzymes.

The present invention also provides antibodies binding to a protein of the present invention. The antibodies of the present invention may take any form, including monoclonal antibodies, as well as polyclonal antibodies. Furthermore, antiserum obtained by immunizing animals such as rabbits and the like with a protein of the invention, all classes of polyclonal and monoclonal antibodies, as well as human and humanized antibodies produced by genetic recombination are included.

A protein of the invention used as an antigen to obtain antibodies may be derived from any animal species, but preferably it is from a mammal such as human, mouse, or rat, and more preferably from a human. A human-derived protein may be obtained by using a nucleotide or amino acid sequence disclosed herein.

A full-length protein or a partial peptide thereof may be used as an antigen in the present invention. A partial peptide may be, for example, an amino (N)-terminus or carboxy (C)-terminus fragment of the protein. Alternatively, a peptide having a transmembrane region of "ALEX1" and such may be used. Herein, an "antibody" is defined as an antibody that reacts with either the full length or a fragment of the protein.

A gene encoding a protein of the invention or its fragment may be inserted into a known expression vector used to transform a host cell as described herein. The desired protein or its fragment may be recovered from the outside or inside of host cells by any standard method, and may be used as the antigen. Alternatively, cells expressing the protein or their lysates, or a chemically synthesized protein may be used as an antigen. Preferably, short peptides are used as antigens by appropriately binding to carrier proteins such as keyhole limpet hemocyanin, bovine serum albumin, or ovalbumin.

Any mammal may be immunized with the antigen, but preferably, the compatibility with parental cells used for cell fusion is taken into account. In general, animals of Rodentia, Lagomorpha, or Primates are used.

Animals of Rodentia include, for example, mice, rats, and hamsters Animals of Lagomorpha include, for example, rabbits Animals of Primates include, for example, monkeys of Catarrhini (old world monkeys) such as *Macaca fascicularis*, rhesus monkeys, sacred baboons, or chimpanzees.

Methods for immunizing animals with antigens are well known. Intraperitoneal injection or subcutaneous injection of antigens is used as a standard method. More specifically, antigens may be diluted and suspended in an appropriate amount with phosphate buffered saline (PBS), physiological saline, etc. If desired, the antigen suspension may be mixed with an appropriate amount of a standard adjuvant, such as Freund's complete adjuvant, made into an emulsion, and then administered to mammals. Preferably, this is followed by several administrations of the antigen mixed with an appropriate amount of Freund's incomplete adjuvant every 4 to 21 days. An appropriate carrier may also be used for immunization. After the above immunization, the serum is examined for an increase of the amount of desired antibodies by a standard method.

Polyclonal antibodies raised against a protein of the present invention may be prepared by collecting blood from the immunized mammal after confirming the increase of desired antibodies in the serum, and by separating serum from the blood by any conventional method. Serum containing a polyclonal antibody may also be used as a polyclonal antibody, or if necessary, the fraction containing the polyclonal antibody may be isolated from the serum. For example, fractions that recognize only a protein of the present invention are obtained by using affinity columns to which the present protein is coupled, and by further purifying the fraction using a protein A or G column, immunoglobulin G or M may be prepared.

To prepare monoclonal antibodies, immune cells are collected from a mammal immunized with an antigen after checked for an increase of the level of the desired antibodies in the serum as described above, and these cells are subjected to cell fusion. The immune cells used for cell fusion are preferably obtained from the spleen. The other parent cell fused with the above immune cell is preferably a mammalian myeloma cell, and more preferably, a myeloma cell that has acquired a special feature that can be used for selecting fusion cells by a drug.

The above immune cell and myeloma cell may be fused by basically any standard method, such as those described in literature (Galfre G. and Milstein C. Methods Enzymol. 73:3-46 (1981)).

Resulting hybridomas obtained by the cell fusion may be selected by cultivating them in a standard selection medium, such as the HAT medium (hypoxanthine, aminopterin, and thymidine containing medium). The cell culture is typically continued in the HAT medium for a period of time that is sufficient to allow all cells except the desired hybridoma (non-fused cells) to die, usually from several days to several weeks. Then, standard limiting dilution is performed to screen and clone a hybridoma cell producing the desired antibody.

Besides the above method in which a nonhuman animal is immunized with an antigen for preparing a hybridoma, human lymphocytes such as those infected by the EB virus may be immunized with a protein, protein-expressing cells, or their lysates in vitro. Then, the immunized lymphocytes are fused with human-derived myeloma cells that are capable of indefinite division, such as U266, to yield a hybridoma producing a desired human antibody capable of binding to a protein of the invention (Unexamined Published Japanese Patent Application (JP-A) No. Sho 63-17688).

Subsequently, the hybridomas thus obtained are transplanted into the peritoneal cavity of a mouse from which the ascites is collected. The monoclonal antibodies thus obtained can be purified by, for example, ammonium sulfate precipitation or column chromatography using a protein A or protein G column, a DEAE ion exchange column, an affinity column and such to which a protein of the invention is coupled. An antibody of the invention can be used not only for purifying and detecting a protein of the invention, but also as a candidate for an agonist or antagonist of a protein of the present invention. An antibody of this invention may be a human antibody or humanized antibody.

For example, transgenic animals having a repertory of human antibody genes may be immunized with a protein, protein expressing cells, or their lysates as antigen. Antibody producing cells are collected from the animals, and fused with myeloma cells to obtain hybridoma, from which human antibodies against the protein can be prepared (see WO92-03918, WO93-2227, WO94-02602, WO94-25585, WO96-33735, and WO96-34096).

Alternatively, an immune cell that produces antibodies, such as an immunized lymphocyte, may be immortalized by an oncogene and used for preparing monoclonal antibodies.

Such monoclonal antibodies can also be recombinantly prepared using genetic engineering techniques (see, for example, Borrebaeck C. A. K. and Larrick J. W. Therapeutic Monoclonal Antibodies, published in the United Kingdom by MacMillan Publishers LTD (1990)). A recombinant antibody can be prepared by cloning DNA encoding the antibody from an immune cell such as a hybridoma or an immunized lymphocyte producing the antibody, inserting this into an appropriate vector, and introducing the vector into a host cell. The present invention also encompasses recombinant antibodies prepared as described above.

An antibody of the present invention may be a fragment of an antibody or modified antibody, so long as it binds to one or more of the proteins of the invention. For instance, the antibody fragment may be Fab, F(ab')$_2$, Fv, or single chain Fv (scFv), in which Fv fragments from H and L chains are linked by an appropriate linker (Huston J. S. et al. (1988) Proc. Natl. Acad. Sci. U.S.A. 85:5879-5883). More specifically, an antibody fragment may be generated by treating an antibody with an enzyme such as papain or pepsin. Alternatively, a gene encoding the antibody fragment may be constructed, inserted into an expression vector, and expressed in an appropriate host cell (see, for example, Co M. S. et al. (1994) J. Immunol. 152:2968-2976; Better M. and Horwitz A. H. (1989) Methods Enzymol. 178:476-496; Pluckthun A. and Skerra A. (1989) Methods Enzymol. 178:497-515; Lamoyi E. Methods Enzymol. (1986) 121:652-663; Rousseaux J. et al. (1986) Methods Enzymol. 121:663-669; Bird R. E. and Walker B. W. (1991) Trends Biotechnol. 9:132-137).

An antibody may be modified by conjugation with a variety of molecules, such as polyethylene glycol (PEG). The present invention provides such modified antibodies. A modified antibody can be obtained by chemically modifying an antibody. These modification methods are conventional in the field.

Alternatively, an antibody of the present invention may be obtained as a chimeric antibody comprising a variable region derived from a nonhuman antibody and the constant region derived from a human antibody, or as a humanized antibody comprising the complementarity determining region (CDR) derived from a nonhuman antibody, the framework region (FR) derived from a human antibody, and the constant region, by using well-known methods.

Obtained antibodies may be purified to homogeneity. Any standard method protein separation and purification method may be used for antibody separation and purification. For example, chromatographies such as affinity chromatography, filters, ultrafiltration, salting out, dialysis, SDS polyacrylamide gel electrophoresis, isoelectric focusing, and such may be appropriately combined to isolate and purify the antibody (Antibodies: A Laboratory Manual. Ed Harlow and David Lane, Cold Spring Harbor Laboratory, 1988). However, the methods are not limited thereto. The concentration of the obtained antibody may be determined by measuring absorbance, by enzyme-linked immunosorbent assay (ELISA), etc.

Columns used for affinity chromatography include, protein A column and protein G column For example, Hyper D, POROS, Sepharose F. F. (Pharmacia), and such may be mentioned as columns using protein A columns.

Chromatographies other than affinity chromatography are, for example, ion exchange chromatography, hydrophobic chromatography, gel filtration chromatography, reverse phase chromatography, adsorption chromatography, and so on (Strategies for Protein Purification and Characterization: A Laboratory Course Manual. Ed Daniel R. Marshak et al., Cold Spring Harbor Laboratory Press, 1996). These chromatographies can be conducted using liquid chromatographies such as HPLC, and FPLC.

For example, measurement of absorbance, enzyme-linked immunosorbent assay (ELISA), enzyme immunoassay (EIA), radioimmunoassay (RIA), or immunofluorescence may be used to measure the antigen binding activity of an antibody of the invention. In ELISA, an antibody of the present invention is immobilized on a plate, a protein of the invention is applied, and then a sample containing a desired antibody, such as culture supernatant of antibody producing cells or a purified antibody, is applied. Then, a secondary antibody labeled with an enzyme such as alkaline phosphatase that recognizes the primary antibody is applied, and the plate is incubated. After washing, an enzyme substrate, such as p-nitrophenyl phosphate, is added to the plate, and the absorbance is measured to evaluate the antigen binding activity of the sample. A fragment of a protein, such as the C-terminus fragment, may be used as the protein. BIAcore (Pharmacia) may be used to evaluate the activity of an antibody according to the present invention.

The above methods allow the detection or measurement of a protein of the invention, by exposing an antibody of the invention to a sample assumed to contain the protein of the invention, and detecting or measuring the immune complex formed by the antibody and the protein. Because the method of detection or measurement of a protein according to the invention can specifically detect or measure a protein, the method may be useful in a variety of experiments in which the protein is used. The method is useful in testing for Alzheimer's disease or cancer as described below.

The present invention also provides a polynucleotide comprising at least 15 nucleotides that is complementary to DNA encoding the human "ALEX1" protein (SEQ ID NO:1 or 2) or to the complementary strand thereof. Polynucleotides of this invention are useful in, for example, to detect or amplify the proteins of the invention, to detect the expression of DNA, or regulate the expression. Herein, the detection of DNA includes the detection of mutations in the DNA.

"Complementary strand" herein refers to one strand of a double strand nucleic acid comprising A:T (U for RNA) and G:C base pairs, when viewed against the other strand. Furthermore, "complementary" means not only when a nucleotide sequence is completely complementary to a continuous nucleotide sequence with at least 15 nucleotides, but also when there is a homology of at least 70% or more, preferably 80% or more, more preferably 90% or more, and much more preferably 95% or more at the nucleotide sequence level. Homology can be determined by using the algorithm described herein.

Such a polynucleotide includes a polynucleotide having at least 15 nucleotides that hybridizes to DNA encoding the human "ALEX1" protein (SEQ ID NO:1 or 2), or to its complementary strand. Preferably, the polynucleotide specifically hybridizes to DNA encoding the human "ALEX1" protein (SEQ ID NO:1 or 2), or to its complementary strand. "Specifically hybridize" means that the polynucleotide does not significantly hybridize to DNA encoding another protein under ordinary hybridization conditions, preferably under the above-described stringent conditions.

Such polynucleotides include probes and primers used for the detection and amplification of DNA encoding a protein of the present invention, probes and primers used for the detection of the expression of the DNA, nucleotides and nucleotide derivatives (for example, antisense oligonucleotides, ribozymes, or DNA encoding them, etc.) used for regulating the expression of a protein of the present invention. Furthermore, such polynucleotides can be used in the preparation of DNA chips or microarray. Polynucleotides of this invention include DNA and RNA, and also sense nucleotides and antisense nucleotides.

If the polynucleotide is used as a primer, the 3' region thereof may be the complementary site, and restriction enzyme recognition sites, tag sequences, and such may be attached to the 5' region.

Antisense oligonucleotides comprise, for example, an antisense oligonucleotide that hybridizes with any portion of the nucleotide sequence of SEQ ID NO:1 or 2. The antisense oligonucleotide is preferably an antisense of a continuous sequence comprising at least 15 nucleotides or more within the nucleotide sequence of SEQ ID NO:1 or 2. More preferably, the above continuous sequence comprising at least 15 nucleotides or more contains a translation initiation codon.

A derivative or modified form of an antisense oligonucleotide may also be used. The latter form may be prepared by modifying an antisense oligonucleotide with lower alkylphosphonates such as methylphosphonate or ethylphosphonate, or with phosphorothioate, or phosphoroamidate.

The antisense oligonucleotide is not restricted to one in which all nucleotides are complementary to the corresponding nucleotides within a given region of DNA or mRNA. As long as it can specifically hybridize with the nucleotide sequence of SEQ ID NO:1 or 2, it may have one or more nucleotide mismatches.

A derivative of an antisense oligonucleotide of the present invention may act on cells producing a protein of the invention and bind to DNA or mRNA encoding the protein, and then, it may inhibit the expression of the protein of the invention by inhibiting its transcription or translation, or by promoting the degradation of mRNA, and thereby inhibiting the function of the protein.

A derivative of an antisense oligonucleotide of the present invention may be mixed with an appropriate base that is inactive against the derivative, and used as a medicine for external application, such as an ointment or poultice.

If necessary, it may be mixed with an excipient, isotonizing agent, solubilizing agent, stabilizer, preservative, pain-killer, or the like, and prepared as a tablet, powder, granule, capsule, liposome capsule, injectable solution, liquid formulation, nose drops, freeze-dried agent, etc. The above may be achieved according to standard methods.

For treating patients, a derivative of an antisense oligonucleotide of the present invention may be, for example, directly applied to the affected area of a patient, or administered into blood vessels so as to finally reach the affected area. Moreover, the derivative may be encapsulated in antisense-encapsulating materials such as liposomes, poly-L-lysine, lipid, cholesterol, lipofectin, or their derivatives in order to increase durability and/or membrane permeability.

Dose of the derivative of the antisense oligonucleotide of the present invention may be appropriately adjusted depending on the patient's conditions, and a favorable amount such as 0.1 to 100 mg/kg, or more, preferably 0.1 to 50 mg/kg, may be administered.

As an antisense oligonucleotide of the present invention inhibits the expression of a protein of the invention, it is useful as an inhibitor of a biological activity of the protein of the invention. An inhibitor of expression comprising an antisense oligonucleotide of the present invention is useful due to its ability to inhibit a biological activity of a protein of the invention.

The antibodies of this invention and the polynucleotides of this invention are useful for testing cancer and Alzheimer's disease. The expression of "ALEX1" gene of this invention was significantly low in cancer cells. This indicates that "ALEX1" can be used for testing cancer. For example, it is possible to test the presence of cancer cells and progress of cancer by detecting the protein of this invention or mRNA encoding this protein in a test sample. Also, since "ALEX1" protein interacts with IDE that is involved in the β-amyloid metabolism, and in addition interacts with PS-1, it is thought to be deeply involved with the onset and progress of Alzheimer's disease. Therefore, "ALEX1" may be used for testing and diagnosing Alzheimer's disease.

In this invention, "testing Alzheimer's disease or cancer" is not only testing patients expressing symptoms of Alzheimer's disease or cancer caused by a mutation of the ALEX1 gene, but also testing ALEX1 gene expression level and genetic mutation performed to decide whether the subject is likely to have Alzheimer's disease or cancer due to an aberration in ALEX1 gene expression level or genetic mutation. That is, even when symptoms have not yet been expressed, the danger of contracting Alzheimer's disease or cancer is thought to be very high when there is an aberration in ALEX1 gene expression, or when a mutation occurs in one of the ALEX1 alleles.

The test for Alzheimer's disease or cancer of this invention can be performed using, for example, antibodies that bind to the protein of this invention, or polynucleotides comprising at least 15 nucleotides that are complementary to DNA encoding the protein of this invention, or to its complementary strand. When the antibodies of this invention and the polynucleotides of this invention are used as test reagents, they can be combined appropriately with stabilizers, preservatives, and salt, solutes such as buffers, water, and solvents such as physiological saline.

One of the test methods for Alzheimer's disease and cancer of this invention is a method comprising detecting the expression level of DNA encoding a protein of this invention in a test sample. Such a test method includes methods comprising (a) contacting the above-mentioned polynucleotide with a patient-derived RNA sample, and (b) detecting binding of the polynucleotide to the RNA sample. Such tests can be performed, for example, by Northern hybridization or RT-PCR. A test of this invention that uses RT-PCR specifically comprises (a) synthesizing cDNA from a patient-derived RNA sample, (b) performing a polymerase chain reaction using the synthesized cDNA as a template and the above-mentioned polynucleotide as a primer, and (c) detecting the DNA amplified by polymerase chain reaction. Northern hybridization and RT-PCR can be performed by well-known genetic engineering techniques. Also, detection by DNA chips or DNA microarrays are also possible.

The test method for Alzheimer's disease or cancer of this invention may comprise detecting the level of a protein of this invention present in a patient-derived test sample. Such tests can be performed, for example, using antibodies against the protein of this invention. Specifically, a test using an antibody of this invention comprises (a) contacting an antibody of this invention with a patient-derived protein sample, and (b) detecting binding of the antibody to the protein sample. Proteins can be detected by immunoprecipitation using the antibodies of this invention, Western blotting, immunohistochemistry, ELISA, and such.

Specifically, these tests may specify cancer and Alzheimer's disease foci by investigating expression by methods such as immunohistological staining or in situ hybridization on tissues collected by biopsy. Decrease in expression of ALEX1 suggests the possibility of onset and/or progress of cancer or Alzheimer's disease. Diseases such as cancer and Alzheimer's are thought to occur due to various reasons. For example, when a decrease in ALEX1 expression is confirmed in cancer, since the activation of the JNK pathway is expected, these tests may be used for diagnosis in performing tailor-made therapy where treatment targeting this pathway is performed.

In addition, the test for Alzheimer's disease or cancer of this invention may be performed by detecting a mutation in the protein of this invention, or a mutation in the DNA encoding this protein. Since the ALEX1 gene is thought to be involved with the onset and/or progress of Alzheimer's disease and cancer, mutations of the protein or the DNA suggest the danger of onset and progress of Alzheimer's disease or cancer.

A mutation of a protein of this invention includes structural and functional mutations. For example, a structural mutation of a protein in a patient-derived protein sample can be tested by using an antibody of this invention and comparing the molecular weight of the protein with a protein derived from a healthy person using Western blotting. Also, it is possible to detect mutations of a protein of this invention by using as indexes, changes in protein modification, changes in binding of proteins or antibodies that bind to the protein of this invention. For these tests, it is possible to use, for example, ELISA, immunoprecipitation, pull-down method, and such that use an antibody against a protein of this invention.

The test for Alzheimer's disease or cancer of this invention may also be performed by detecting the binding of a protein of this invention with the IDE protein, PS-1 protein, or JIP-1 protein. Otherwise, it may be performed by detecting binding of a protein of this invention with p0071 (plakophilin-4), SART-1, MSP58, ATRX, CSA2 (RED protein), p68 (RNA helicase/ATPase), OS-9, ZNF189, KIAA1221, α-Actinin4, or ZIP kinase Inhibition of the binding between a protein of this invention and such a protein is thought to contribute to the onset and progress of Alzheimer's disease or cancer. Binding of proteins can be evaluated, for example, by ELISA, immunoprecipitation, and pull-down method, using an antibody against a protein of this invention.

For detecting a mutation in DNA encoding a protein of this invention, a nucleotide sequence of cDNA encoding the protein of this invention, and oligonucleotide (probe and primer) complementary to the nucleotide sequence of a genomic DNA sequence (including endogenous transcription regulatory sequence) or to its complementary strand may be used. Incidentally, testing a mutation includes a testing that specifies patients (carriers) having a mutation in one of the ALEX1 alleles.

When used as a primer, polynucleotides are normally 15 to 100 bp, and preferably 17 to 30 bp. There are no limitations on the primer as long as it can amplify at least a portion of the ALEX1 gene region or a region that regulates its expression. Examples of such regions include, for example, exons, introns, promoters, and enhancer regions of the ALEX1 gene.

On the other hand, as a probe, the polynucleotide normally comprises at least 15 by or longer if it is a synthetic polynucleotide. Double-stranded DNA obtained from a clone that has been inserted into a vector such as plasmid DNA may also be used as a probe. There are no limitations on the probe as long as it is complementary to the nucleotide sequence of at least a portion of the ALEX1 gene or the region regulating its expression, or to its complementary strand. The region to which the probe hybridizes includes, for example, the exon, intron, promoter, and enhancer regions of the ALEX1 gene. When used as probes, the polynucleotide or the double stranded DNA are labeled appropriately, and then used. The labeling methods are, for example, phosphorylating the 5'-end of polynucleotide with $^{32}P$ using T4 polynucleotide kinase, or incorporating a substrate nucleotide labeled with biotin, fluorescent dye, isotope such as $^{32}P$, and such, and using a random hexamer oligonucleotide as a primer and DNA polymerase such as Klenow enzyme (random priming method).

One embodiment of a method for detecting mutations of the ALEX1 gene is to directly determine the nucleotide sequence of the ALEX1 gene of a patient. For example, using the above-mentioned nucleotide as a primer, and DNA isolated from a patient suspected to have a disease caused by mutation of ALEX1 as a template, a portion or whole of the patient's ALEX1 gene (for example, regions including exon, intron, promoter, and enhancer) is amplified by, for example, PCR (Polymerase Chain Reaction), and its nucleotide sequence is determined. By comparing this to the sequence of a normal person's ALEX1 gene, diseases caused by a mutation of the ALEX1 gene can be tested.

As the testing method of this invention, various methods are used besides the method of directly determining the nucleotide sequence of DNA derived from patients. In one embodiment, the method comprises, (a) preparing a DNA sample from a patient, (b) amplifying the patient-derived DNA using the polynucleotide of this invention as a primer, (c) dissociating the amplified DNA into single-stranded DNA, (d) separating the dissociated single stranded DNA on a non-denaturing gel, and (e) comparing the mobility of the separated single-stranded DNA on the gel with a control from a healthy person.

An example of such methods is PCR-SSCP (single-strand conformation polymorphism) method (Cloning and polymerase chain reaction-single-strand conformation polymorphism analysis of anonymous Alu repeats on chromosome 11. Genomics. 1992 Jan. 1; 12(1): 139-146, Detection of p53 gene mutations in human brain tumors by single-strand conformation polymorphism analysis of polymerase chain reaction products. Oncogene. 1991 Aug. 1; 6(8): 1313-1318, Multiple fluorescence-based PCR-SSCP analysis with postlabeling, PCR Methods Appl. 1995 Apr. 1; 4(5): 275-282). This method is relatively facile and has the advantage of requiring a small amount of samples. Therefore, it is especially preferable when screening many DNA samples. Its principles are as follows. When a double-stranded DNA fragment is dissociated into single strands, each strand forms an independent higher-order structure according to its nucleotide sequence. When this dissociated DNA strand is electrophoresed in a polyacrylamide gel that does not contain a denaturant, depending on the difference in each higher-order structure, complementary single-stranded DNA having the same chain length move to a different position. Higher order structure of such single-stranded DNA changes even with replacement of a single nucleotide, and indicates different mobility in polyacrylamide gel electrophoresis. Therefore, by detecting this change in mobility, existence of a mutation in the DNA fragment such as point mutation, deletion, or insertion can be detected.

Specifically, first the whole ALEX1 gene, or a portion of it, is amplified by PCR and such. Normally, the amplified range preferably has approximately 200 to 400 bp. Also, the amplified range includes all exons and all introns of the ALEX1 gene and also, promoters and enhancers of the ALEX1 gene. During gene fragment amplification by PCR, synthesized DNA fragments are labeled by performing PCR using a primer labeled with isotopes such as $^{32}$P or with fluorescent dyes, biotin, and such, or by adding a substrate nucleotide labeled with isotopes such as $^{32}$P, or with fluorescent dyes, biotin, and such into the PCR solution. Otherwise, labeling can be performed by adding a substrate nucleotide labeled with isotopes such as $^{32}$P, or with fluorescent dyes, biotin, and such to a synthesized DNA fragment using Klenow enzyme, and such, after PCR. The labeled DNA fragment obtained this way is denatured by heating and such, and electrophoresis is performed using a polyacrylamide gel that does not contain denaturants such as urea. Here the conditions for DNA fragment separation can be improved by adding an appropriate amount (approximately 5 to 10%) of glycerol to the polyacrylamide gel. Also, electrophoretic conditions change with properties of each DNA fragment, but normally, it is performed at room temperature (20 to 25° C.). When a favorable separation cannot be obtained, the temperature that gives the most appropriate mobility is tested between 4 to 30° C. After electrophoresis, mobility of the DNA fragment is detected by autoradiography using an X-ray film, a scanner detecting fluorescence, and such, and then analyzed. When a band having a difference in mobility is detected, this band is directly cut out from the gel, then re-amplified by PCR, and by direct sequencing, the existence of a mutation can be confirmed. Also, even when labeled DNA is not used, by staining the gel after electrophoresis with ethidium bromide or silver staining and such, bands can be detected.

Another embodiment of the testing method of this invention includes (a) preparing a DNA sample from a patient, (b) amplifying the patient-derived DNA using a polynucleotide of this invention as a primer, (c) cleaving the amplified DNA, (d) separating the DNA fragments according to their size, (e) hybridizing the detectably labeled probe DNA of this invention to the separated DNA fragment, and (f) comparing the size of the detected DNA fragment with a control of a healthy person.

Examples of such methods are methods using restriction fragment length polymorphism (RFLP), PCR-RFLP, and such. Normally, restriction enzymes are used as enzymes to cleave DNA. Specifically, when a mutation exists at the restriction enzyme recognition site, or when there is a nucleotide insertion or deletion in the DNA fragment formed by restriction enzyme treatment, the size of the fragment formed after restriction enzyme treatment changes compared to that of a healthy person. This portion containing the mutation is amplified by PCR, and by treatment with each restriction enzyme, these mutations can be detected as differences in band mobility after electrophoresis. Otherwise, chromosomal DNA is treated with these restriction enzymes and after electrophoresis, by performing Southern blotting using the probe DNA of this invention, the presence or absence of mutation can be detected. The restriction enzyme to be used can be selected appropriately depending on each mutation. In this method, besides genomic DNA, RNA prepared from a patient is made into cDNA by reverse transcriptase and after cleaving it in its original form by a restriction enzyme, Southern blotting can be performed. Also, using this cDNA as a template, a portion or whole of the ALEX1 gene can be amplified by PCR, and after cleaving them with restriction enzyme, their difference in mobility can be investigated.

Furthermore, instead of using DNA prepared from a patient, a similar detection is possible using RNA as well. Such a method comprises (a) preparing a RNA sample from a patient, (b) separating the prepared RNA according to size, (c) hybridizing the polynucleotide of this invention that has a detectable label as a probe to the separated RNA, and (d) comparing the size of the detected RNA with a control from a healthy person. An example of a specific method comprises electrophoresing RNA prepared from a patient, performing Northern blotting using a polynucleotide of this invention as a probe, and detecting differences of mobility.

Another embodiment of the test methods of this invention comprises (a) preparing a DNA sample from a patient, (b) amplifying the patient-derived DNA using the polynucleotide of this invention as a primer, (c) separating the amplified DNA on a gel in which the concentration of DNA denaturant gradually rises, and (d) comparing mobility of the separated DNA on the gel compared to a control of a healthy person.

An example of such a method is denaturant gradient gel electrophoresis (DGGE). The whole ALEX1 gene, or a portion of it, is amplified by PCR using the primer of this invention, and such. This is then electrophoresed in a polyacrylamide gel in which the concentration of a denaturant such as urea gradually becomes higher as the material moves, and this is compared to that of a healthy person. For a DNA fragment in which a mutation exists, the DNA fragment becomes single stranded at a position of lower denaturant concentration, and the rate of movement becomes extremely slow. Therefore, by detecting this difference in mobility, the presence or absence of a mutation can be detected.

Besides these methods, for the purpose of detecting mutations only at a particular position, allele specific oligonucleotide (ASO) hybridization can be used. An oligonucleotide containing a sequence in which a mutation is thought to exist is prepared, and when this is hybridized with sample DNA, if a mutation exists, the efficiency of hybrid formation decreases. This can be detected by Southern blotting or by a method that utilizes the property of quenching by intercalation of a specialized fluorescent reagent into a gap in the hybrid, or such a method. Also, detection by ribonuclease A mismatch cleavage method is possible. Specifically, the whole ALEX1 gene, or a portion of it, is amplified by PCR and such, and the product is hybridized with labeled RNA prepared from ALEX1 cDNA and such inserted in a plasmid vector, and such. In the portion in which a mutation exists, the hybrid becomes a single-stranded structure, therefore, this portion is cleaved by ribonuclease A, and by detecting this with autoradiography, and such, existence of a mutation can be detected.

A protein of the invention may be useful for screening for a compound that binds to the protein. Specifically, the protein may be used in a method of screening for the compound binding to the protein of the invention, such a method comprising the steps of exposing the protein of the present invention to a test sample expected to contain a compound binding to the protein, and selecting a compound having the activity of binding to the protein.

Proteins of the invention used for screening may be recombinant or natural proteins, or partial peptides. For example, screening can be performed using a partial peptide lacking the transmembrane domain, or a partial peptide containing a transmembrane domain, and such. Compounds that bind to the transmembrane domain of ALEX1 protein may regulate intracellular localization of the protein by interfering with transmembrane domain function. Proteins used for screening may be in the form expressed on the surface of a cell, or in the form of a membrane fraction. Samples tested include, but are not limited to, cell extracts, cell culture supernatants, products of fermentation microorganisms, marine organism extracts, plant extracts, purified or crude preparations of proteins, peptides, non-peptide compounds, synthetic low-molecular weight compounds, and natural compounds. A protein of the present invention contacted with a test sample may be brought into contact with the test sample, for example, as a purified protein, as a soluble protein, in the form attached to a carrier, a fusion protein with other proteins, in the form expressed on the cell membrane, or as a membrane fraction.

Various methods known to one skilled in the art may be used as the screening method of, for example, a protein that binds to a protein of the present invention using a protein of the present invention. Such a screening can be carried out, for example, by the immunoprecipitation method. Specifically, the method can be carried out as follows. A gene encoding a protein of this invention is expressed by inserting the gene into vectors for foreign gene expression such as pSV2neo, pcDNA I, and pCD8, and expressing the gene in animal cells, etc. Any generally used promoter may be employed for the expression, including the SV40 early promoter (Rigby In Williamson (ed.), Genetic Engineering, Vol. 3. Academic Press, London, p. 83-141 (1982)), EF-1α promoter (Kim, D M et al. Gene 91, p. 217-223 (1990)), CAG promoter (Niwa, H. et al. Gene 108, p. 193-200 (1991)), RSV LTR promoter (Cullen, B R, Methods in Enzymology 152, p. 684-704 (1987)), SR α promoter (Takebe Y et al., Mol. Cell. Biol. 8, p. 466-472 (1988)), CMV immediate early promoter (Seed B and Aruffo A, Proc. Natl. Acad. Sci. USA 84, p. 3365-3369 (1987)), SV40 late promoter (Gheysen D and Fiers W, J. Mol. Appl. Genet. 1, p. 385-394 (1982)), Adenovirus late promoter (Kaufman R J et al., Mol. Cell. Biol. 9, p. 946-958 (1989)), HSV TK promoter, etc. Transfer of a foreign gene into animal cells for expression therein can be performed by any of the following methods, including the electroporation method (Chu, G. et al., Nucl. Acid Res. 15, 1311-1326 (1987)), the calcium phosphate method (Chen, C. and Okayama, H. Mol. Cell. Biol. 7, 2745-2752 (1987)), the DEAE dextran method (Lopata, M. A. et al. Nucl. Acids Res. 12, 5707-5717 (1984); Sussman, D. J. and Milman, G. Mol. Cell. Biol. 4, 1642-1643 (1985)), the lipofectin method (Derijard, B. Cell. 7, 1025-1037 (1994); Lamb, B. T. et al. Nature Genetics 5, 22-30 (1993)), Rabindran, S. K. et al. Science 259, 230-234 (1993)), etc. A protein of this invention can be expressed as a fusion protein having a recognition site for a monoclonal antibody whose specificity has been established by introducing the recognition site (epitope) into the N- or C-terminal of a protein of this invention. For this purpose, a commercial epitope-antibody system can be utilized (Jikken Igaku (Experimental Medicine) 13, 85-90 (1995)). Vectors that are capable of expressing fusion proteins with β-galactosidase, maltose-binding protein, glutathione S-transferase, green fluorescence protein (GFP), and such, via a multi-cloning site are commercially available.

To minimize the alteration in properties of a protein of this invention due to fusion protein formation, a method for preparing a fusion protein by introducing only a small epitope portion comprising several to ten amino acid residues has been reported. For example, the epitopes of polyhistidine (His-tag), influenza agglutinin (HA), human c-myc, FLAG, Vesicular stomatitis virus glycoprotein (VSV-GP), T7 gene 10 protein (T7-tag), human herpes simplex virus glycoprotein (HSV-tag), E-tag (epitope on the monoclonal phage), and such, and monoclonal antibodies to recognize these epitopes can be utilized as the epitope-antibody system for screening for proteins binding to the protein of this invention (Jikken Igaku (Experimental Medicine) 13, 85-90 (1995)).

In immunoprecipitation, immune complexes are formed by adding these antibodies to the cell lysate prepared using suitable detergents. This immune complex comprises a protein of this invention, a protein capable of binding to the protein, and an antibody. The immunoprecipitation can also be performed using an antibody to a protein of this invention, besides antibodies to the above-described epitopes. An antibody to a protein of this invention can be prepared by, for example, inserting a gene encoding a protein of this invention into an appropriate expression vector of E. coli to express it in the bacterium, purifying the protein thus expressed, and immunizing rabbits, mice, rats, goats, chicken, and such, with the purified protein. The antibody can also be prepared by immunizing the above-described animals with synthetic partial peptides of a protein of this invention.

Immune complexes can be precipitated using, for example, Protein A Sepharose and Protein G Sepharose when the antibody is a murine IgG antibody. In addition, when the protein of this invention is prepared as a fusion protein with the epitope of, for example, GST, and such, the immune complex can be precipitated using a substance that specifically binds to these epitopes, such as glutathione-Sepharose 4B, and such, giving the same result as in the case where the antibody for the protein of this invention is used.

Immune precipitation, in general, may be carried out according to, or following the method described in literature (Harlow, E. and Lane, D.: Antibodies, pp. 511-552, Cold Spring Harbor Laboratory publications, New York (1988)).

SDS-PAGE is generally used for the analysis of immunoprecipitated proteins. Bound proteins can be analyzed based on the molecular weights of proteins using a gel of an appropriate concentration. In this case, although proteins bound to the protein of this invention, are in general hardly detectable by the usual protein staining method, such as Coomassie staining and silver staining, the detection sensitivity can be improved by culturing cells in a medium containing radio isotope-labeled $^{35}$S-methionine and $^{35}$S-cysteine to incorporate radiolabels biosynthetically, and detecting the labeled proteins. Once the molecular weight of the protein is determined, the desired protein can be purified directly from SDS-polyacrylamide gel and sequenced.

Isolation of a protein that binds to a protein of the present invention using the protein may be carried out by, for example, using the West-Western blotting method (Skolnik E. Y. et al. (1991) Cell 65:83-90). Specifically, a cDNA library is constructed from cells, tissues, or organs (for example, tissues from ovary, heart, testis, prostate, brain, spleen, skeletal muscle, colon, and so on) in which a protein binding to a protein of the present invention is expected to be expressed, by using phage vectors (λgt11, ZAP, etc.). Then, this is expressed on LB-agarose, transferred to a filter membrane, which is reacted with a purified labeled protein of the invention. The plaques expressing proteins that bind to the protein of the invention can be identified by detecting the label. The protein of the invention may be labeled by a method utilizing the binding between biotin and avidin, or a method utilizing an antibody that specifically binds to the protein of the present invention, or a peptide or polypeptide (e.g. GST and such) that is fused to the protein of the present invention. Methods using radioisotope or fluorescence and such may also be used.

Alternatively, in another embodiment of the method for screening of the present invention, a two-hybrid system utilizing cells may be used (Fields S, and Sternglanz R. (1994) Trends Genet. 10:286-292; Dalton S, and Treisman R. (1992) Characterization of SAP-1, a protein recruited by serum response factor to the c-fos serum response element, Cell 68:597-612; "MATCHMAKER Two-Hybrid System", "Mammalian MATCHMAKER Two-Hybrid Assay Kit", "MATCHMAKER One-Hybrid System" (products of Clontech); "HybriZAP Two-Hybrid Vector System" (Stratagene)).

The two-hybrid system can be used as follows: (1) a protein of the present invention or a partial peptide thereof is fused to the SRF DNA binding region or GAL4 DNA binding region and expressed in yeast cells; (2) a cDNA library, which expresses proteins as fusion proteins with VP16 or GAL4 transcription activating regions, is prepared from cells expected to express proteins binding to the protein of the present invention; (3) the library is introduced to above mentioned yeast cells; and (4) library-derived cDNA are isolated from the positive clones detected (positive clones can be confirmed by activation of reporter genes due to the binding of the present protein and the binding protein expressed in the yeast cell). The protein encoded by the cDNA can be obtained by introducing the isolated cDNA into E. coli and expressing it. Thus, a protein binding to a present protein or genes thereof can be prepared. For example, in addition the HIS3 gene, Ade2 gene, LacZ gene, CAT gene, luciferase gene, PAI-1 (Plasminogen activator inhibitor type1) gene, and so on, can be mentioned as reporter genes used in the 2-hybrid system, but are not restricted thereto. In addition to yeast, mammalian cells and such can be used for the 2-hybrid screening.

Alternatively, a protein binding to a protein of the present invention can be screened by affinity chromatography. For example, a protein of the invention is immobilized on a carrier of an affinity column, and a test sample, in which a protein capable of binding to the protein of the invention is presumed to be expressed, is applied to the column. The test sample used herein may be a cell extract, cell lysate, etc. After loading the test sample, the column is washed, and a protein bound to the protein of the invention can be obtained.

The DNA encoding the protein may be obtained by analyzing the amino acid sequence of the obtained protein, synthesizing oligo DNA based on the sequence information, and screening a cDNA library using the DNA as the probe.

A biosensor utilizing the surface plasmon resonance phenomenon may be used as a means for detecting or measuring bound proteins. When such a biosensor is used, the interaction between a protein of the invention and a test protein can be observed at real-time as a surface plasmon resonance signal, using only a minute amount of proteins without labeling (for example, BIAcore, Pharmacia). Therefore, it is possible to evaluate the binding between a protein of the invention and a test compound using a biosensor such as BIAcore.

In addition, methods for isolating not only proteins, but also compounds binding to the proteins of the invention (including agonists and antagonists) are known in the art. Such methods include, for example, the method of screening for a binding molecule by contacting synthesized compounds or natural substance libraries, or random phage peptide display libraries with an immobilized protein of the invention, and the high-throughput screening method using the combinatorial chemistry technique (Wrighton, N. C. et al., Small peptides as potent mimetics of the protein hormone erythropoietin, Science, 1996, 273 p 458-64; Verdine G. L., The combinatorial chemistry of nature, Nature, 1996, 384, p 11-13; Hogan J. C. Jr., Directed combinatorial chemistry, Nature, 1996, 384, p 17-9).

This invention also provides a screening method for compounds that regulate binding between the protein of this invention and the IDE protein. This screening method comprises, (a) contacting the protein of this invention with the IDE protein in the presence of a test sample, (b) detecting the binding between these proteins, and (c) selecting a compound having activity to promote or inhibit the binding between these proteins, compared to when the detection is made in the absence of the test sample.

This invention also provides a screening method for compounds that regulate the binding between the protein of this invention and the PS-1 protein. This screening method comprises, (a) contacting the protein of this invention with the PS-1 protein in the presence of a test sample, (b) detecting the binding between these proteins, and (c) selecting a compound having activity to promote or inhibit the binding between these proteins, compared to when the detection is made in the absence of the test sample.

This invention also provides a screening method for compounds that regulate binding between the protein of this invention and the JIP-1 protein. This screening method comprises, (a) contacting the protein of this invention with the JIP-1 protein in the presence of a test sample, (b) detecting the binding between these proteins, and (c) selecting a compound having activity to promote or inhibit the binding between these proteins, compared to when the detection is made in the absence of the test sample.

This invention also provides a screening method for compounds that regulate the binding between the protein of this invention and a protein selected from the group consisting of p0071 (plakophilin-4), SART-1, MSP58, ATRX, CSA2 (RED protein), p68 (RNA helicase/ATPase), OS-9, ZNF189, KIAA1221, α-Actinin4, and ZIP kinase. This screening method comprises, (a) contacting the protein of this invention with a protein selected from the group consisting of p0071 (plakophilin-4), SART-1, MSP58, ATRX, CSA2 (RED protein), p68 (RNA helicase/ATPase), OS-9, ZNF189, KIAA1221, α-Actinin4, and ZIP kinase in the presence of a test sample, (b) detecting the binding between these proteins, and (c) selecting a compound having activity to promote or inhibit the binding between these proteins, compared to when the detection is made in the absence of the test sample.

Each protein used for these screenings is not restricted by its form as long as it has the ability to form a complex or has a binding ability. It does not have to be a full length protein, and it can be a mutant or a partial peptide. It may also be a natural protein or a recombinant protein. It may be a fusion protein with another peptide. These proteins may be prepared similarly to the above-mentioned case relating to screening of compounds that bind to the protein of this invention. Also, human derived proteins, or proteins derived from other animals can be used as proteins, such as IDE protein, PS-1 protein, and JIP-1 protein, that are contacted with the protein of this invention. Samples tested include, but are not limited to, cell culture supernatants, products of fermentation microorganisms, marine organism extracts, plant extracts, prokaryotic cell extracts, eukaryotic single cell extracts, animal cell extracts, libraries thereof, purified or crude preparations of proteins, peptides, non-peptide compounds, synthetic low-molecular weight compounds, and natural compounds. A protein used for the screening may be used, for example, as a purified protein, as a soluble protein, in the form attached to a carrier, a fusion protein with other proteins, in the form expressed on the cell membrane, or as a membrane fraction.

This type of screening can be performed, for example, by a two-hybrid method using yeast or animal cells. Specifically, DNA encoding the protein of this invention, and DNA encoding a protein contacted with the protein of this invention, such as IDE, PS-1, or JIP-1, are fused to either a sequence encoding a transcription activation domain or a DNA binding sequence of an appropriate transcription factor such as GAL4, intracellularly co-expressed with a GAL4 luciferase reporter vector and such, and a promoter or inhibitor substance can be screened using this luciferase activity as an index.

It is also possible to perform screening using, for example, immunoprecipitation. The protein of this invention and a protein such as IDE, PS-1, or JIP-1, contacted with the protein of this invention are incubated in the presence of a test sample, a complex is collected with an antibody against one of the proteins or with an antibody against a tag fused to the protein, and such, and then by detecting the other protein using antibodies and such against that protein, binding with the protein of this invention can be evaluated. If the other protein is labeled with a different tag, and such, detection can be easily done. One of the proteins is bound to a support, then the other protein is bound, and then, a test sample is applied. By detecting whether the bound protein dissociates, the effect of the test sample can be investigated. Also, it is possible to perform screening using ELISA.

Screening can also be performed by utilizing surface plasmon resonance as indicated in the screening of proteins that bind to the protein of this invention, high-throughput screening utilizing combinatorial chemistry, etc.

This invention also provides a screening method that uses as an index, inhibition of MKK7/JNK-mediated signal transduction by expression of a protein of this invention. This screening method comprises (a) contacting a test sample with a cell expressing the protein of this invention, (b) detecting MKK7/JNK-mediated signal transduction in the cell, and (c) selecting a compound having activity to promote or inhibit the signal transduction. There are no particular limitations on the test sample.

The proteins of this invention, MKK7, JNK, and such may be endogenous or those externally introduced for expression, but to confirm specificity of compounds obtained by screening to ALEX1, it is preferable to externally introduce the ALEX1 gene using a cell that does not have endogenous ALEX1 expression. Most epithelial cancer cells match this criterion. By comparison with cells to which the ALEX1 gene had not been introduced, specificity towards ALEX1 can be confirmed. For example, HeLaS3 cells used in Example 10 are thought to be preferable for screening as they have no endogenous expression of ALEX1 and have an endogenous expression of MKK7. Also, to avoid too much complexity of screening system, a cell in which components of the JNK pathway and JIP1 are expressed endogenously, and the JNK pathway operates responding to stimuli, is preferred. For this type of example, there are no particular limitations, but MCF7 breast cancer cells (Monno, S. et al., Endocrinology 2000, 141(2):544-550) or KB3 cells (Stone, A. A. & Chambers, T. C., Exp. Cell Res. 2000, 254(1):110-119) may be used. Especially in the former, since activation of the JNK pathway by IGF-1 stimulus has been reported, introduction of MEKK1 is not necessary, and a screening system may be constructed with relative ease.

It is also considered preferable to use, for example, human epithelial cancer cell line derived from oral cavity, KB (ATCC #CCL-17). KB cells include MKK7 and JNK, and the JNK pathway is activated by TNFα (Moriguchi, T. et al. (1997) EMBO J. 16, 7045-7053). The JNK pathway of KB cells can be also activated with IL-1 (Krause, A. et al. (1998) J. Biol. Chem. 273, 23681-23689). A549 cells can also be used. Expression of ALEX1 cannot be detected by the Northern blotting, nor by RT-PCR in A549 cells (see Examples). The JNK pathway of this cell can be activated by EGF (Bost, F. et al. (1997) J. Biol. Chem. 272, 33422-33429). An example of other cells is ovarian cancer cell line SK-OV-3, in which the JNK pathway can be activated by Cisplatin treatment, but is not limited to this example (Persons et al. (1999) Clin. Cancer Res. 5, 1007-1014).

Substances affecting MKK7/JNK-mediated signal transduction can be screened, for example, as shown in Example 10, by detecting c-Jun-dependent transcription. Specifically, a vector expressing the c-Jun protein that has been fused with an appropriate DNA binding protein such as GAL4, and a reporter vector in which a reporter gene such as luciferase is linked downstream of a binding sequence of the DNA binding protein are introduced into cells expressing the protein of this invention, and by detecting the reporter in the presence or absence of a test sample, screening can be performed using the effect of the test sample on promotion or inhibition of c-Jun-dependent transcription by the protein of this invention as an index. As another method, ATF2-dependent reporter activity reported to be activated by JNK (Adamson, A. L. et al., J. Virol. 2000, 74(3):1224-33) can be detected. It is also possible to detect phosphorylation of c-Jun or ATF2 protein through MKK7 using antibodies. Specifically, for c-Jun, detection is possible by sandwich ELISA using an antibody against phosphorylated (N-terminal) c-Jun and an antibody against another portion of c-Jun (or anti-tag antibody). A similar system can be used in the case of ATF2.

Compounds that bind to the proteins of this invention, compounds that regulate binding between the proteins of this invention and proteins that bind to them, and compounds that regulate MKK7/JNK-mediated signal transduction, isolable by the above-mentioned screening, become, for example, candidates of drugs that promote or inhibit the activity of the proteins of this invention. Therefore, such a compound can be and applied to the treatment of diseases caused by an expressional or functional abnormality, and such, of a protein of this invention and diseases that are treatable by regulating the activity of a protein of this invention.

It may also be possible to utilize genes encoding the proteins of this invention or their expression regulatory regions to screen for compounds that may adjust the expression (including transcription and translation) of these genes in vivo or in cells. This screening may be used, for example, for screening for candidate compounds for therapeutic and prophylactic agents for cancer and Alzheimer's disease.

This screening may be performed by the method comprising, (a) contacting a test sample with a cell that endogenously expresses the DNA of this invention, (b) detecting the expression, and (c) selecting a compound having activity to promote or inhibit the expression compared to when the cell is not contacted with the test sample (control). Transcription and translation are included in this DNA expression.

For example, screening of the desired compound can be performed by cultivating cells expressing the ALEX1 gene with a test sample, detecting expression (including transcription and translation) of the gene by mRNA detection methods such as Northern analysis and RT-PCR, or protein detection methods such as Western blotting, immunoprecipitation, and ELISA, or by methods in which these are improved, and selecting compounds that promote or inhibit expression of the gene compared to when the test sample is not added.

There are no particular limitations on the cells used for screening, but from the viewpoint of cancer therapy where induction of ALEX1 expression is expected to lead to treatment, screening of compounds that promote expression of ALEX1 using various cancer cell lines in which the expression of ALEX1 is decreased, such as cervical adenocarcinoma cell line HeLa, lung carcinoma cell line A549, non-small cell lung carcinoma cell line ABC-1, and cervical adenocarcinoma cell line C-33A can be considered. On the contrary when decrease in expression is the objective, screening can be performed using glioblastoma cell line A172, osteosarcoma cell line TE-85, or normal fibroblastic cell line MRC5, and such.

In methods to detect mRNA such as Northern analysis and RT-PCR, for example, a polynucleotide containing at least 15 nucleotides complementary to DNA comprising the nucleotide sequence of SEQ ID NO:1 or 2 or to its complementary strand may be used as a probe or a primer. In methods to detect proteins such as Western blotting, immunoprecipitation, and ELISA, an antibody of this invention can be used.

Screening of compounds that regulate the expression of the gene of this invention in vivo or within a cell can also be done by a method that uses the activation or inactivation of expression regulatory region of the gene of this invention as an index. This screening may be performed by the method comprising (a) contacting a test sample with a cell into which a vector having a reporter gene operably linked downstream of an endogenous transcription regulatory sequence of the DNA of this invention has been introduced, (b) detecting expression of the reporter gene within the cell, and (c) selecting a compound having activity to promote or inhibit expression of the reporter gene compared to when the cell is not contacted with the test sample (control).

Here, "endogenous transcription regulatory sequence" refers to sequences regulating transcription of the DNA in cells naturally maintaining expression of the DNA of this invention. Such sequences include promoters, enhancers, and/or repressors. For these sequences, for example, DNA in the upstream region of a gene encoding the protein of this invention may be used. For example, a DNA fragment spanning several kb upstream from the transcription initiation site (or translation initiation codon) of a gene encoding the protein of this invention, is considered to contain the endogenous transcription regulatory sequence of the gene mentioned above. By joining this fragment with a reporter gene, it is possible to place expression of the reporter gene under transcriptional control of a gene encoding the protein of this invention. It is possible to measure transcription regulating activity by introducing deletions or mutations appropriately to the upstream region, and to identify the sequence involved in transcriptional regulation and to use that fragment. Currently, many transcription regulatory sequences that bind to transcription factors involved in various transcriptional regulations are known. Such known transcription regulatory sequences could be found in the upstream region of a gene encoding the protein of this invention, and regarded to be involved in the endogenous transcription regulatory sequence. Normally, multiple sequences regulating gene transcription exist on one gene, and in the screening of this invention, any one sequence or a combination of sequences may be used. Endogenous transcription regulatory sequences may be made as chimeras with other promoters. Chimeric promoters are often used for testing transcriptional regulation. Other promoters used to produce chimeric promoters include, for example, a minimum promoter derived from SV40 early promoter. "Operably linked" indicates that the transcription regulatory sequence and a reporter gene are linked so that the reporter gene linked downstream may be expressed in response to activation of the transcription regulatory sequence.

Specifically, for example, by screening a genomic DNA library using the nucleotide sequence of SEQ ID NO:1 or 2 or a portion of it as a probe, transcription regulatory region (promoter, enhancer, etc.) of the DNA of this invention is cloned, then an expression vector in which this is inserted upstream of an appropriate reporter gene (chloramphenicol acetyl transferase gene, luciferase gene, etc.) is prepared, and then, this is introduced to a mammalian cell. Next, a test sample is contacted with the cell line, reporter activity is detected, and by selecting compounds that increase or decrease reporter activity compared to reporter activity in cells that are not contacted with the test sample, compounds that may regulate the expression of the gene of this invention within a cell can be screened. Because this screening detects expression of the DNA of this invention using reporter activity as an index, it is very convenient, compared to direct detection such as the above-mentioned Northern analysis.

The compounds that regulate the expression of the genes of this invention, isolated by these screenings become candidates of drugs toward various diseases caused by an aberrant expression of the gene of this invention. Especially, use as a drug for preventing and treating diseases such as Alzheimer's disease and cancer is anticipated.

ALEX1 is thought to suppress the onset and progress of cancer. In Alzheimer's disease, it is thought to suppress the onset or progress by guiding IDE, which is thought to contribute to the breakdown of amyloid peptides, to the sites of amyloid production. Compounds that promote the binding between ALEX1 and JIP-1, compounds that inhibit MKK7/JNK signal transduction, and compounds that elevate expression of ALEX1 may contribute to the prevention and treatment of cancer. Similarly, in Alzheimer's disease, compounds that promote the binding between ALEX1 and IDE, compounds that promote the binding between ALEX1 and PS-1, and compounds that elevate the expression of ALEX1 are thought to contribute to the prevention and treatment of Alzheimer's disease. Furthermore, since JNK is involved in apoptosis, compounds obtained from the screenings of this invention may be applied to apoptosis-related diseases. JNK pathway is activated by various stresses, however, its involvement in apoptosis differs according to the cell type. In one example, in apoptosis of myocardial cells injured by high oxygen tension, the JNK pathway is suggested to function protectively by inhibiting TNF production (Minamino, T. et al., Proc. Natl. Acad. Sci. USA 1999, 96(26): 15127-32). On the other hand, mouse fibroblast cells lacking c-Jun are resistant to apoptosis caused by drugs that alkylate DNA, and this has been explained to be due to the involvement of c-Jun in inducing the expression of CD95L (FASL) caused by an alkylating agent (Kolbus, A. et al., Mol. Cell Biol. 2000 January; 20(2): 575-82). Therefore, in a combination of a stimulus and a cell system in which activation of JNK promotes apoptosis, cell protection due to an inhibition of JNK pathway can be expected. On the contrary, in a combination that suppresses apoptosis, induction of cell death due to inhibition of JNK pathway can be expected.

In addition, since compounds that inhibit the binding between ALEX1 and JIP-1, compounds that promote MKK7/JNK signal transduction, and compounds that decrease the expression of ALEX1 can inhibit the mechanism that is normally regulated negatively by ALEX1, they may be used for organ regeneration, and such. Also, compounds that inhibit the binding between ALEX1 and IDE, compounds that inhibit the binding between ALEX1 and PS-1, and compounds that decrease the expression of ALEX1 are useful for pathological analysis of Alzheimer's disease and for producing animal models of Alzheimer's disease.

Also, since proteins such as p0071 (plakophilin-4), SART-1, MSP58, ATRX, CSA2 (RED protein), p68 (RNA helicase/ATPase), OS-9, ZNF189, KIAA1221, α-Actinin4, and ZIP kinase that interact with ALEX1 are suggested to be related to Alzheimer's disease and/or cancer, compounds that regulate the binding between ALEX1 and these proteins are also expected to have a utility as drugs for preventing or treating diseases such as Alzheimer's disease or cancer.

Compounds that may be isolated by the screenings of this invention become candidates of drugs regulating the activity or expression of the proteins of this invention. Thus, therapeutic application is possible for diseases caused by expressional aberrations, functional aberrations, and such of the protein of this invention, and diseases treatable by regulating the activity and expression of a protein of this invention. Substances in which a part of the structure of compounds that may be isolated by the screening method of this invention has been modified by an addition, deletion, and/or substitution are included in the compounds that bind to the proteins of this invention.

When using a compound that can be isolated by the screenings of this invention as a pharmaceutical agent for humans and other mammals, such as mice, rats, guinea-pigs, rabbits, cats, dogs, sheep, pigs, cattle, monkeys, baboons, and chimpanzees, and also for chicken, the protein or the isolated compound can be directly administered or can be formulated using known pharmaceutical preparation methods. For example, according to the need, the drugs can be taken orally as sugarcoated tablets, capsules, elixirs and microcapsules or non-orally in the form of injections of sterile solutions or suspensions with water or any other pharmaceutically acceptable liquid. For example, the compounds can be mixed with pharmacologically acceptable carriers or medium, specifically, sterilized water, physiological saline, plant-oil, emulsifiers, solvents, surfactants, stabilizers, flavoring agents, excipients, vehicles, preservatives and binders, in a unit dose form required for generally accepted drug implementation. The amount of active ingredients in these preparations makes a suitable dosage within the indicated range acquirable.

Examples of additives that can be mixed to tablets and capsules are, binders such as gelatin, corn starch, tragacanth gum and arabic gum; excipients such as crystalline cellulose; swelling agents such as corn starch, gelatin and alginic acid; lubricants such as magnesium stearate; sweeteners such as sucrose, lactose or saccharin; flavoring agents such as peppermint, Gaultheria adenothrix oil and cherry. When the unit dosage form is a capsule, a liquid carrier, such as oil, can also be included in the above ingredients. Sterile composites for injections can be formulated following normal drug implementations using vehicles such as distilled water used for injections.

Physiological saline, glucose, and other isotonic liquids including adjuvants, such as D-sorbitol, D-mannose, D-mannitol, and sodium chloride, can be used as aqueous solutions for injections. These can be used in conjunction with suitable solubilizers, such as alcohol, specifically ethanol, polyalcohols such as propylene glycol and polyethylene glycol, non-ionic surfactants, such as Polysorbate 80 ™ and HCO-50.

Sesame oil or Soy-bean oil can be used as a oleaginous liquid and may be used in conjunction with benzyl benzoate or benzyl alcohol as a solubilizer; may be formulated with a buffer such as phosphate buffer and sodium acetate buffer; a pain-killer such as procaine hydrochloride; a stabilizer such as benzyl alcohol, phenol; and an anti-oxidant. The prepared injection is filled into a suitable ampule.

Methods well known to one skilled in the art may be used to administer a pharmaceutical agent to patients, for example as intraarterial, intravenous, subcutaneous injections and also as intranasal, transbronchial, intramuscular, percutaneous, or oral administrations. The dosage varies according to the body-weight and age of a patient, and the administration method, but one skilled in the art can suitably select the dosage. If said compound can be encoded by DNA, the DNA can be inserted into a vector for gene therapy to perform the therapy. The dosage and method of administration vary according to the body-weight, age, and symptoms of a patient, but one skilled in the art can select them suitably.

Although varying according to the subject, target organ, symptoms, and method of administration, the dose of a compound that binds to a protein of this invention, a compound that inhibits or promotes the activity of a protein of this invention, a compound that inhibits or promotes the expression of the protein, and such, which can be isolated by the screening of this invention, are generally in the range of about 0.1 to 100 mg, preferably about 1.0 to 50 mg, and more preferably about 1.0 to 20 mg per day for adults (body weight: 60 kg) in the case of an oral administration.

Although varying according to the subject, target organ, symptoms, and method of administration, a single dose of a compound for parenteral administration is preferably, for example, when administered intravenously to normal adults (60 kg body weight) in the form of injection, in the range of about 0.01 to 30 mg, preferably about 0.1 to 20 mg, and more preferably about 0.1 to 10 mg per day. Doses converted to 60 kg body weight or per body surface area can be administered to other animals.

In vitro translated ALEX1 protein was incubated with either IDE-Flag-immobilized beads or control beads. After washing the beads, the bound proteins were separated by SDS-PAGE and observed by autoradiography. In vitro translated luciferase used as a negative control ([$^{35}$S]Lucifer) did not bind to IDE-Flag beads. The [$^{35}$S]ALEX1 and [$^{35}$S]luciferase used for the reactions (containing 10% of proteins added to the reactions) are shown for comparison (lanes "input"). In this figure, lane M shows [$^{14}$C]methylated protein molecular weight markers.

FIG. 2 shows multiple alignment of the amino acid sequences of the human ALEX1, ALEX2 (GenBank Accession No. BAA25438), and ALEX3.

The amino acid sequence for ALEX3 is the translation of the putative human cDNA sequence (257925) in the TIGR database Amino acid sequences were aligned by ClustalW, and homologous amino acids were shaded using Boxshade 3.21 program. Black residues are identical amino acids. Arm motifs are boxed.

FIG. 3 shows multiple alignment of the amino acid sequences of the human ALEX1, ALEX2, and ALEX3 (SEQ ID NOS:3, 14, 15) (continued from FIG. 2).

Figure 4:
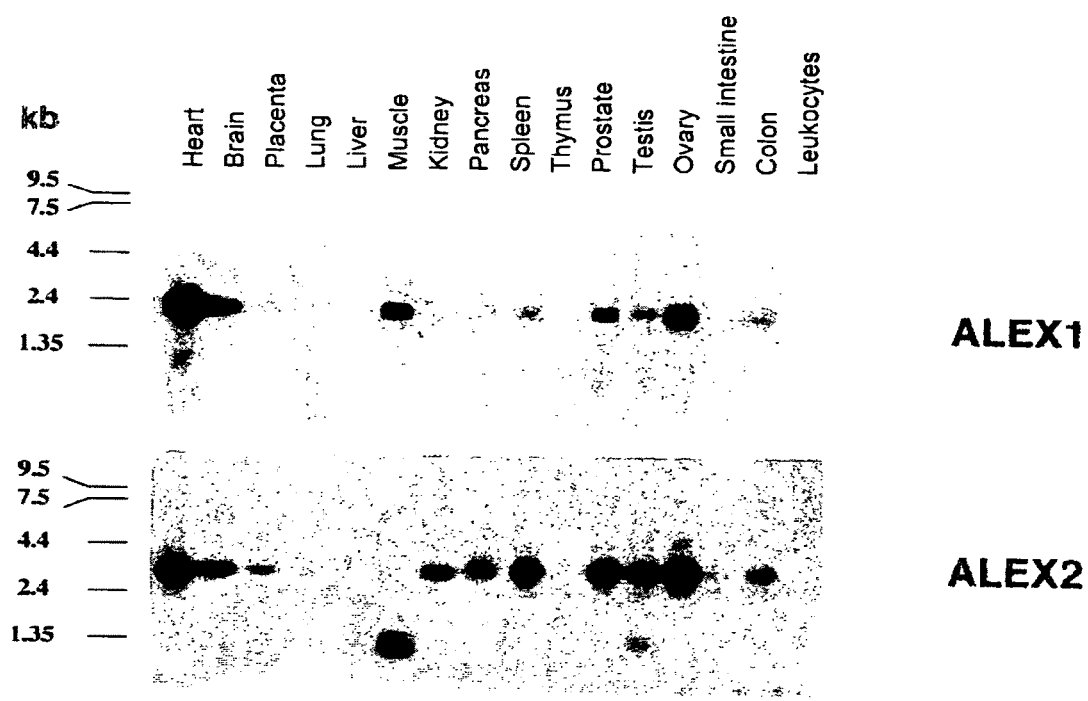

FIG. 4 shows Northern blot analysis of ALEX1 and ALEX2 mRNA expression.

Northern blot containing 2 µg poly (A)$^+$ RNA from various human adult tissues (Clontech) was hybridized with the probe against the coding region of the ALEX1 and ALEX2. Molecular size markers are shown on the left.

Figure 5:
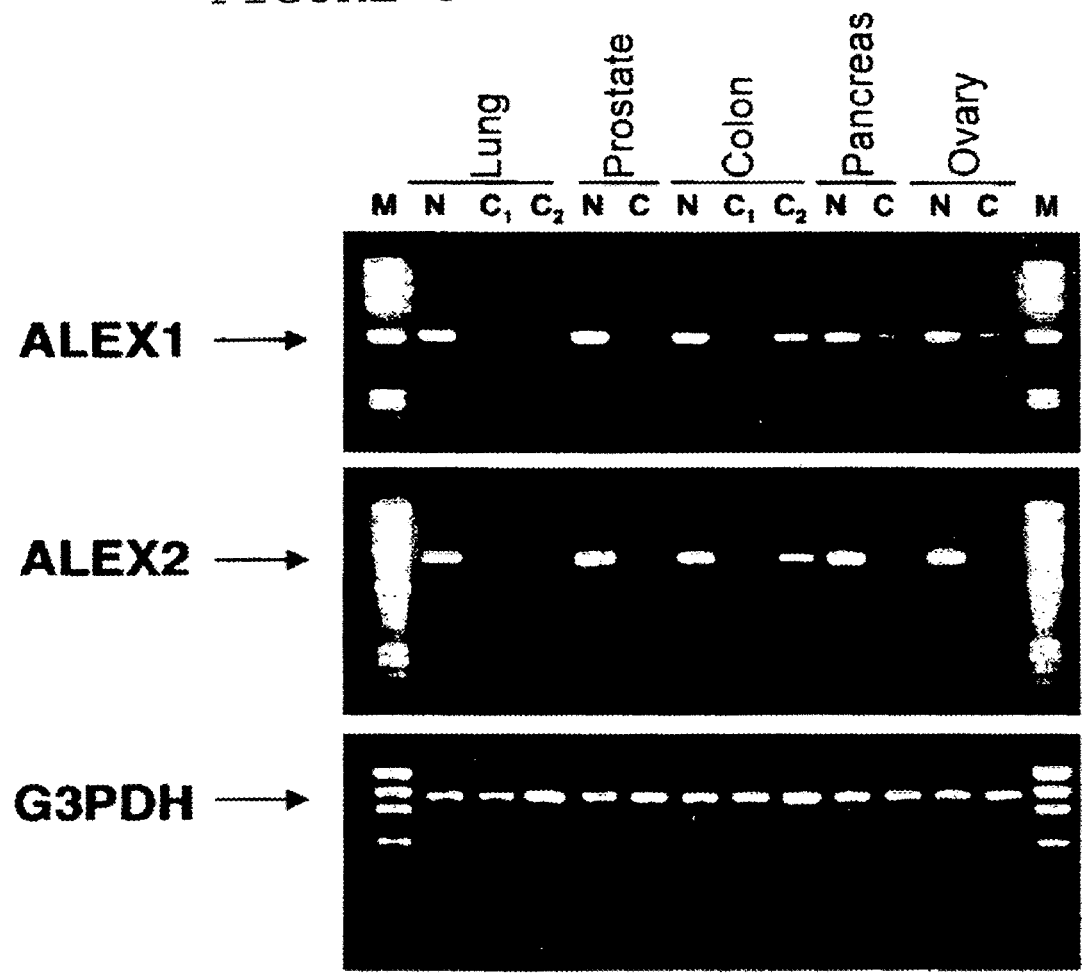

FIG. 5 shows tissue-specific expression pattern of ALEX1 and ALEX2 mRNA in normal tissues compared with tumor samples.

cDNA prepared from various tumor samples and corresponding normal tissues (Multiple Tissue cDNA Panels, Clontech) were used as templates for PCR with the primers specific for ALEX1 and ALEX2. PCR products were then analyzed by electrophoresis using 2% agarose/EtBr gel. N, normal tissues. Lung carcinomas: $C_1$, Human Lung Carcinoma (LX-1); $C_2$, Human Lung Carcinoma (GI-117). Prostate carcinoma: C, Human Prostatic Adenocarcinoma (PC3). Colon carcinomas: $C_1$, Human Colon Adenocarcinoma (CX-1); $C_2$, Human Colon Adenocarcinoma (GI-112). Pancreatic carcinoma: C, Human Pancreatic Adenocarcinoma (GI-103). Ovarian carcinoma: C, Human Ovarian Carcinoma (GI-102). DNA size markers (φX174 digested with HaeIII) are shown in lane M.

Figure 6:
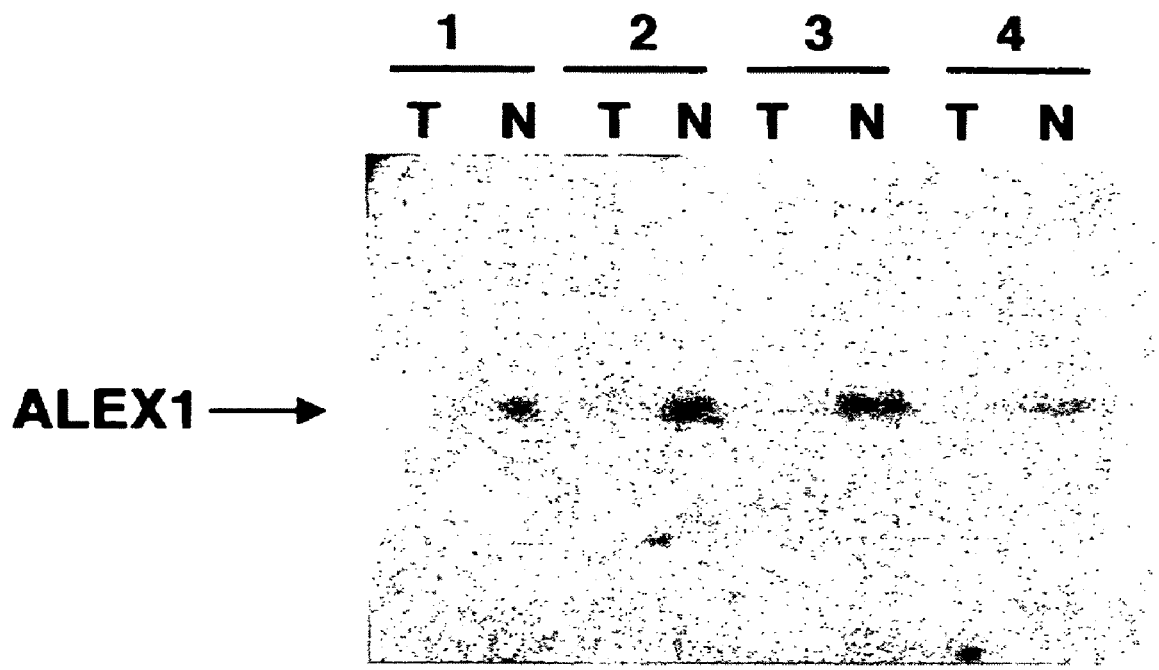

FIG. 6 shows Northern blot analysis of ALEX1 in human tumor and normal ovaries.

Northern blot contains 20 μg of total RNA prepared from each of tumor and corresponding normal tissues excised at the same operational site (Human Ovarian Tumor Blot, Invitrogen). Donors: 1—serous cystadenocarcinoma of left ovary (age—48 years old); 2—serous cystadenocarcinoma (30 years); 3—granulosa-theca cell tumor (42 years); 4—adenocarcinoma (28 years). T, tumor tissue; N, normal tissue.

Figure 7:
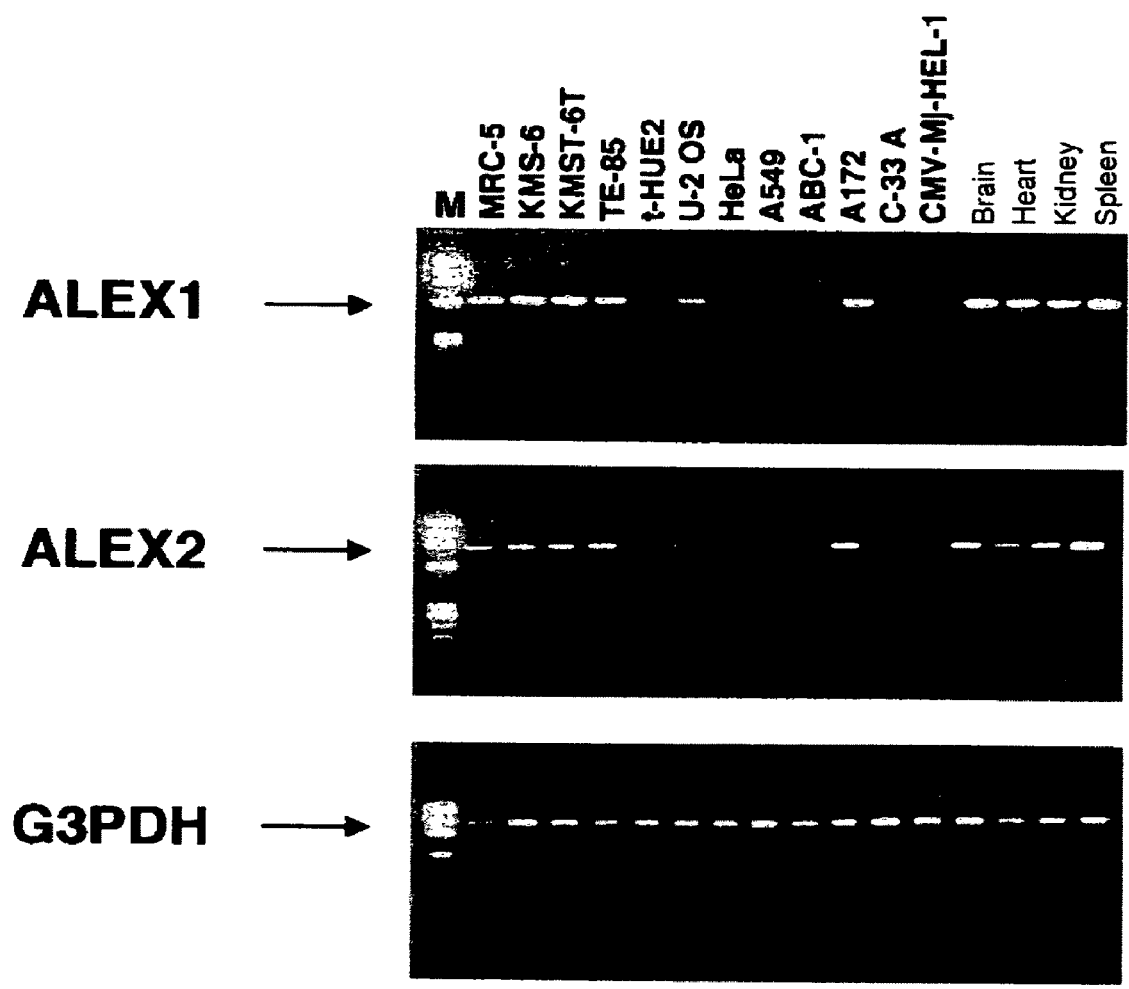

FIG. 7 shows expression of ALEX1 and ALEX2 mRNA in human normal compared with transformed cell lines.

cDNA prepared from various human cell lines and normal tissues were used as templates for PCR with the same primers combinations used in the above figure. PCR products were then analyzed by electrophoresis using 2% agarose/EtBr gel. Normal tissues (Human MTC Panel, Clontech): brain, heart, kidney, and spleen. Cell lines of human origin: MRC-5, normal fetal lung diploid fibroblast cell line; KMS-6, normal diploid fetal fibroblast cell line; KMST-6T, neopastically transformed cell line derived from KMS-6; TE-85, malignant osteosarcoma cell line; t-HUE2, immortal cell line established from endothelial cell line ECV304; U-2 OS, osteosarcoma cell line; HeLa, cervix adenocarcinoma cell line; A549, lung carcinoma cell line; ABC-1, non-small cell lung carcinoma cell line; A172, malignant glioma cell line; C-33 A, cervical carcinoma cell line; CMV-Mj-HEL-1, CMV-transformed embryo lung fibroblast cell line. DNA size markers (φX174 digested with HaeIII) are shown in lane M.

Figure 8:
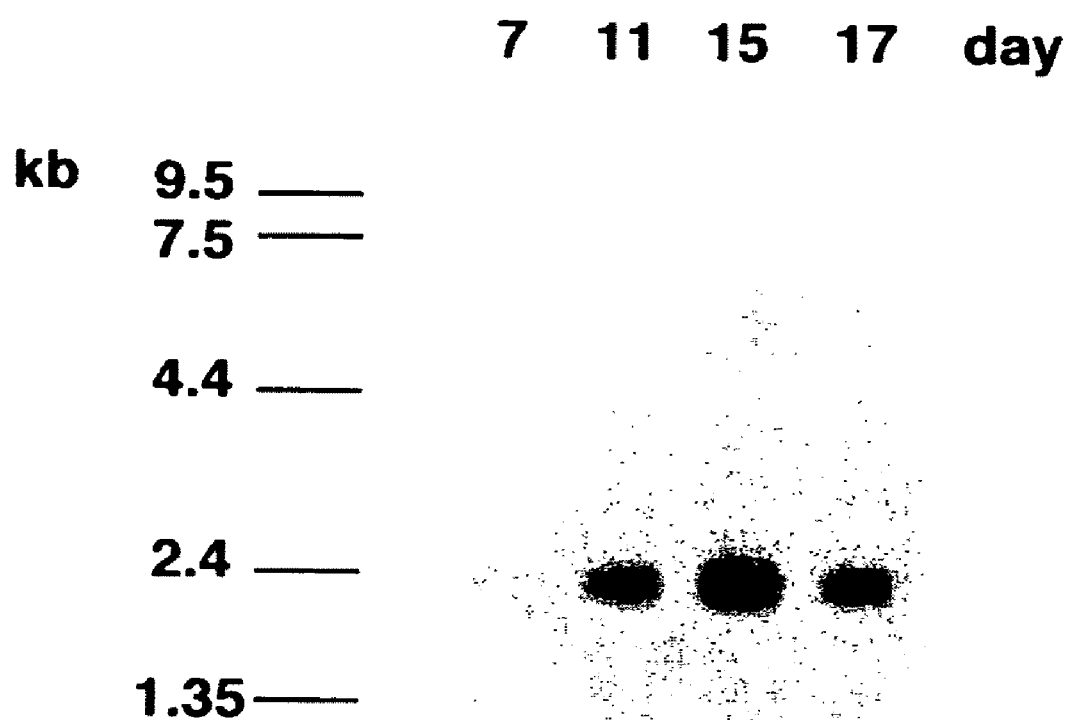

FIG. 8 shows expression analysis of ALEX1 mRNA during mouse embryo development.

Northern blot containing 2 μg poly (A)$^+$ RNA from whole mouse embryo at different stages of development (Clontech) was hybridized to the probe prepared based on the ALEX1-homologous sequence found in mouse EST database. Molecular size markers are shown on the left.

Figure 9:
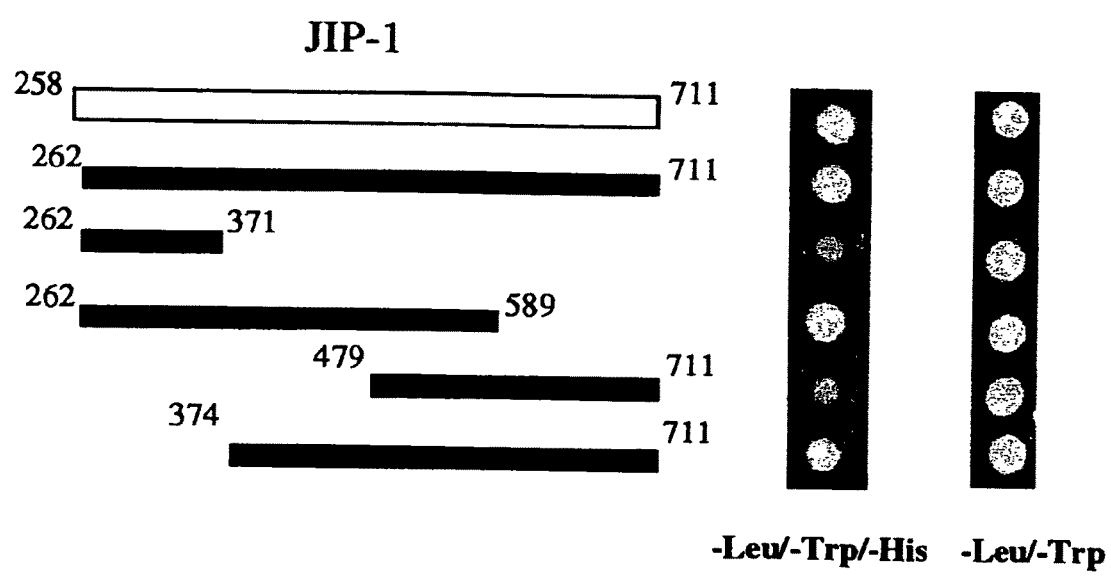

FIG. 9 shows the analysis of interaction of JIP-1 fragments with ALEX1 protein.

JIP-1 deletion constructs were transformed into PJ69-4A yeast carrying pODB-80-ALEX1 using a plasmid to which a Gal-4 transcription activation domain was ligated. This was then plated on plates that lacked Leu, Trp, and His, and contained 1 mM 3-AT. Growth on -Leu-Trp-His plate indicates interaction. In parallel, the yeast were plated onto -Leu-Trp plate to confirm successful transformation. Fragment of amino acid numbers 258 to 711 indicates the smallest JIP-1 clone (19A3) found originally in the yeast two-hybrid screen.

Figure 10:
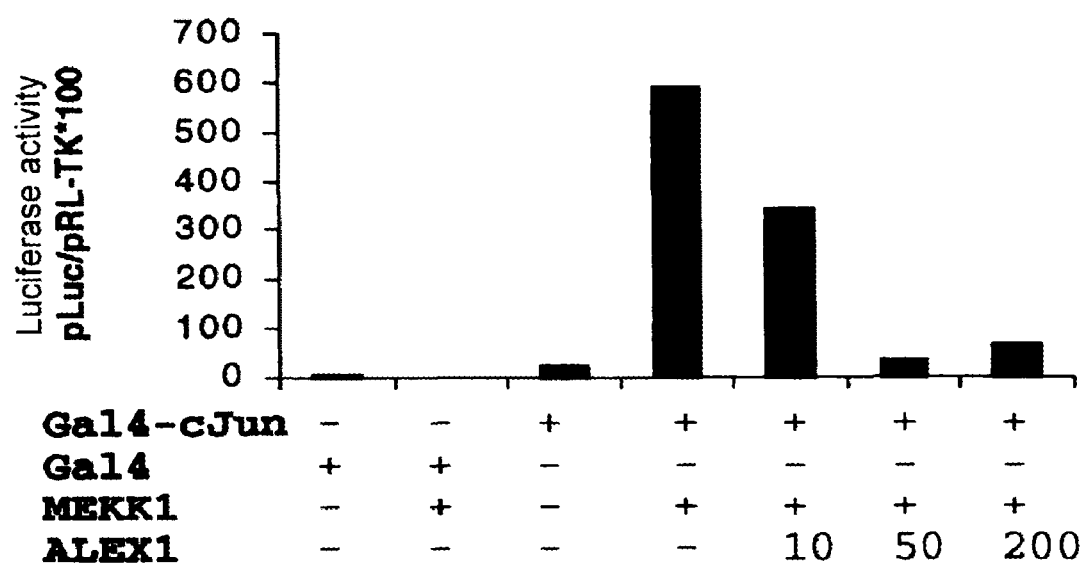

FIG. 10 shows inhibition of c-Jun-dependent transcription activation by ALEX1.

The c-Jun-dependent reporter gene pG5-Luc (encoding firefly luciferase protein) (500 ng) together with the *Renilla* luciferase-encoding plasmid pRL-TK (50 ng) as the internal control, and expression vectors for Gal14 (25 ng), Gal4-cJun (25 ng), MEKK1 (50 ng), and ALEX1 were transfected into HeLa S3 cells as indicated. Luciferase activity was measured 42 h post-transfection. The values shown on the vertical axis represent the relative level of firefly luciferase to the *Renilla* luciferase activity used as the internal control. The assay was performed in duplicates.

BEST MODE FOR CARRYING OUT THE INVENTION

The present invention will be explained in detail below with reference to Examples, but it is not to be construed as being limited thereto. All references cited herein are incorporated into this description. Primers used in Examples are as follows:

```
ALEX 1 specific primers:
F1, GTGCTCGGGTTAAGAGATTTGTC;      (SEQ ID NO: 4)

F2, TCACAATGATCTGGTGGTG;          (SEQ ID NO: 5)

F3, CAACATGACTGTGACTAATC;         (SEQ ID NO: 6)

R1, AGCTCCTTTCACAGTCTC;           (SEQ ID NO: 7)

R2, ACCCAACCATTACAACCAACATCAG;    (SEQ ID NO: 8)

R3, GGCCATGTTGTAGCTGGAGCCCTGGTGC; (SEQ ID NO: 9)

ALEX2 specific primers:
F4, TAGCAGCACCTACCAAGGTAG;        (SEQ ID NO: 10)

F5, TGCCTTGCTTCAGAAATCTG;         (SEQ ID NO: 11)

R4, CCCAGTTCGTCTACTTCAACT;        (SEQ ID NO: 12)
and

R5, CTTCCACACTCICAAAATCATG.       (SEQ ID NO: 13)
```

Sequences were determined on both strands of double stranded-DNA using the ABI dRhodamine Terminator Cycle Sequencing Ready Reaction Kit, and an ABI Prism 377 Genetic Analyzer (Perkin-Elmer/Applied Biosystems). The nucleotide sequences obtained were assembled and analyzed using Auto Assembler DNA Sequence Assembly Software (Applied Biosystems). Homologies with known nucleic acids and proteins registered in the GenBank and EMBL databases were analyzed using the BLAST algorithm (Altschul S. F. et al. (1990) J. Mol. Biol. 215, 403-410) Amino acid sequences were compared using the BLASTP and PROSITE programs (Altshul, S. F. et al. (1997) Nucleic Acids Res. 25, 3389-3402; Bairoch, A. et al. (1997) Nucleic Acids Res. 25, 189-196). Motif searches were performed with Pfam at the Sanger Center, UK. Prediction of protein transmembrane domains was performed with SOSUI program (Hirokawa, T. et al. (1998) Bioinformatics 14, 378-379) Amino acid sequence alignment was obtained with Clustal W (Thompson, J. D. et al. (1994) Nucleic Acids Res. 22, 4673-4680).

EXAMPLE 1 cDNA Cloning and Protein Analysis

The yeast two-hybrid system was used to isolate proteins that interact with IDE. Yeast two-hybrid screening was performed with the strain PJ69-4A (James, P. et al. (1996) Genetics 144, 1425-1436) carrying three reporter genes, HIS3, ADE, and LacZ under the control of GAL4 promoter. Mutation-introduced full-length insulin-degrading enzyme IDE (H108Q; the mutant lacking catalytic activity but preserving substrate-binding activity) was linked to Gal4-DB (DNA-binding domain of Gal4) in frame, and cloned into pODB-80 vector. This was used as a bait plasmid. Yeast cells were transformed with the bait plasmid and the expression of fusion proteins was confirmed by Western blot. Then, the yeast cells carrying the bait plasmid were transformed with a prey plasmid, the pACT2-human brain cDNA library (Clontech). Double transformants carrying both of the bait and prey were directly selected on synthetic medium (SD) lacking Leu, Trp, and His plus 1 mM 3-aminotriazole (3-AT). Growing clones were then selected on SD lacking Leu, Trp, His, and adenine, and assayed for β-galactosidase activity by filter assay. Plasmid DNA was extracted from positive colonies using Plasmid Mini Kit from Qiagen and electroporated into *E. coli* DH5αstrain. Human brain-derived inserts obtained were sequenced with GAL4-AD specific primer.

During this process, several candidate cDNA were obtained from normal human brain library. Sequencing of the 1290 by cDNA insert from clone B4 revealed that the sequence has an 879-bp-long open reading frame (ORF), encoding a polypeptide of 293 amino acids. Analysis of the predicted amino acid sequence against Pfam database identified within it two 42 amino acid armadillo/beta-catenin-like repeats. The insert from clone B4 already contained polyA-sequence at its 3'-end. Therefore, 5'-RACE was employed to obtain the rest of the sequence using human heart cDNA as a template.

The 5'-RACE was performed using Advantage cDNA Polymerase Mix (Clontech) with primer R3 and pAP3neo human heart cDNA library (Takara) as a template. The touchdown PCR was conducted under the conditions as follows: 94° C. for 1 min, for 1 cycle; 94° C. for 30 sec, 72° C. for 5 min for 5 cycles; 94° C. for 30 sec, 70° C. for 5 min for 5 cycles; 94° C. for 20 sec, 68° C. for 5 min for 25 cycles; 72° C. for 7 min for 1 cycle; and the temperature was held at 4° C. The PCR-product obtained was purified via electrophoresis, cloned into the vector pCR2.1-TOPO (Invitrogen), and sequenced using T7 primer, M13 primer, and a series of insert-specific primers.

The largest amplified product contained additional 851 by to the sequence of B4 toward 5' direction, bringing total length of the sequence to 2141 by together with the B4 sequence (named ALEX1). The nucleotide sequence and predicted amino acid sequence of this ALEX1 cDNA are shown in SEQ ID NOS: 1 and 3, respectively. Because of possibility of errors introduced during RACE-PCR, B4 cDNA was cloned also by hybridization-based screening of cDNA library.

Namely, Human Testis cDNA library cloned in pCMV-SPORT vector (Gibco BRL) was divided into 36 pools each containing 3072 clones and gridded onto Nylon filters. The pools were screened by PCR with F1/R1 primers and ALEX1 cDNA-positive filters were hybridized to the 208-bp probe generated by PCR using same primers. The probe was radio-labeled with [$\alpha$-$^{32}$P] dCTP (3000 Ci/mmol) (Amersham) using the Megaprime DNA Labeling System (Amersham). Inserts from respective positive clones were sequenced.

As compared with the sequence obtained in the above RACE method (SEQ ID NO:1), the sequence of clone 144D10 having the largest insert length (2124 bp) obtained through this screening (SEQ ID NO:2) differs in the 44 nucleotides at the 5'-end, and its $45^{th}$ (G) corresponds to $51^{st}$ (G) of SEQ ID NO:1. There is a single nucleotide insertion of (A) at the $77^{th}$ nucleotide, and three nucleotides at positions 129 to 131 (AGT) are deleted. There are differences in the 3'-end as well: substitution of the $2130^{th}$ nucleotide of A to C; $2132^{nd}$ nucleotide of A to G; and there is no poly(A). Other parts including the coding regions are identical. As will be shown later on, the divergence in the latter nucleotide sequence occurs exactly at the junction of exon 1 and exon 2 of the gene.

E. coli containing the ALEX1 cDNA clone isolated by screening the human testis-derived cDNA library has been deposited as "pCMV-SPORT-ALEX1" in the following depository.

(a) Name and Address of Depository
Name: National Institute of Bioscience and Human-Technology, Advanced Industrial Science and Technology, Ministry of Economy, Trade and Industry
(Old name: National Institute of Bioscience and Human-Technology, Agency of Industrial Science and Technology)
Address: 1-1-3 Higashi, Tsukuba, Ibaraki, Japan (Zip code 305-8566)

(b) Date of Deposition (Date of Original Deposition): Feb. 25, 2000
(c) Accession Number: FERM BP-7056

The putative initiation codon of the ALEX1 cDNA sequence (SEQ ID NO:1) is the ATG starting from position 372 and located within a nucleotide sequence adequate for translation initiation signal (ACCATGG) (Kozak, M. (1984) Nucleic Acids Res. 12, 857-873). The first in-frame stop codon (TAA) was identified at nucleotide 1731, predicting a protein product of 453 amino acids with a calculated molecular weight of 49,178 and a calculated isoelectric point (pI value) of 9.56. The polyadenylation signal AATAAA is located 19 by upstream of the polyadenylation starting site (SEQ ID NO:1).

Sequence analysis of the ALEX1 protein revealed in addition to the above-described two Arm repeats, an ATP/GTP-binding site at $162^{nd}$ to $169^{th}$ amino acids. Potential phosphorylation sites present in ALEX1 protein include eight potential protein kinase C sites and five potential casein kinase II sites. The SOSUI algorithm predicts a transmembrane domain at the N-terminus of the protein ($1^{st}$ to $25^{th}$ amino acids). The transmembrane domain contains four putative myristoylation sites. At the C-terminus, ALEX1 contains microbodies targeting signal.

EXAMPLE 2

Interaction of ALEX1 with IDE

As described above, the yeast two-hybrid screen with full-length IDE mutant (H108Q) as a bait identified clone B4 corresponding to C-terminal part of ALEX1 protein (amino acid numbers 161 to 453). This prompted additional studies to determine whether IDE interacts with full-length ALEX1 and also whether the interaction between two proteins is direct. For this purpose, the full-length ALEX1- and IDE-encoding cDNA were subcloned into the E. coli expression vector pGEX-5X to express ALEX1 and IDE as fusion proteins with GST. Both proteins were found in E. coli insoluble fraction. ALEX1 was solubilized from the inclusion bodies using a denaturant. Obtained protein, however, was likely to be misfolded as it interacted with several unrelated $^{35}$S-labeled proteins (data not shown). Such difficulties associated with the expression of mammalian proteins in E. coli were widely known. To overcome this, the inventors switched to the insect expression system. Flag-tagged IDE mutant (H108Q) was expressed in Sf9 cells and purified using agarose beads onto which M2-anti-Flag antibody was immobilized.

Specifically, IDE mutant (H108Q) cDNA fused to the Flag epitope at the 5'-end was cloned into the insect cell expression vector pIZ/V5-His (InsectSelect System, Invitrogen). The construct was transfected into the insect cell line Sf9. Stably transfected cells were selected by the growth in a medium containing Zeocin at 0.4 mg/ml.

For in vitro binding assays, the gene-introduced cells were collected, washed in PBS, resuspended in lysis buffer (containing 50 mM Tris-HCl, pH 7.2, 150 mM NaCl, 1% Triton X-100 and Complete protease inhibitor cocktail, Boehringer Mannheim), sonicated to disrupt the cells, and centrifuged 10 min at 15,000×g. Supernatant after the centrifugation was purified through the affinity column in which the M2 anti-Flag antibody was immobilized (Sigma). Specifically, the supernatant after the centrifugation was applied onto the column, and then the column was washed with the binding buffer (containing 20 mM Tris-HCl, pH 7.2, 150 mM NaCl, 1 mM EDTA, 0.1% Tween-20, and Complete protease inhibitor cocktail). Bound IDE-Flag protein was eluted with Flag peptide (Sigma) at 0.1 mg/ml and dialyzed against the binding buffer to remove the Flag peptide.

On the other hand, the biosynthesis of full-length ALEX1 protein was performed to produce the protein labeled with [$^{35}$S]-methionine in rabbit reticulocyte lysates. For binding experiments, 5 μl of $^{35}$S-labeled ALEX1 or luciferase (negative control) was mixed with 2.5 μg of IDE in 0.4 ml of the binding buffer and incubated for 2 h at 4° C. Then 15 μl of the anti-Flag M2 antibody-immobilized affinity beads was added and incubation continued for 2.5 h at 4° C. The beads were washed five times in the binding buffer. Bound protein was eluted with 0.1 mg/ml Flag peptide, resolved by SDS-PAGE, stained with Coomassie blue and analyzed with a Phosphoimager (BAS2000, Fuji).

Figure 1:
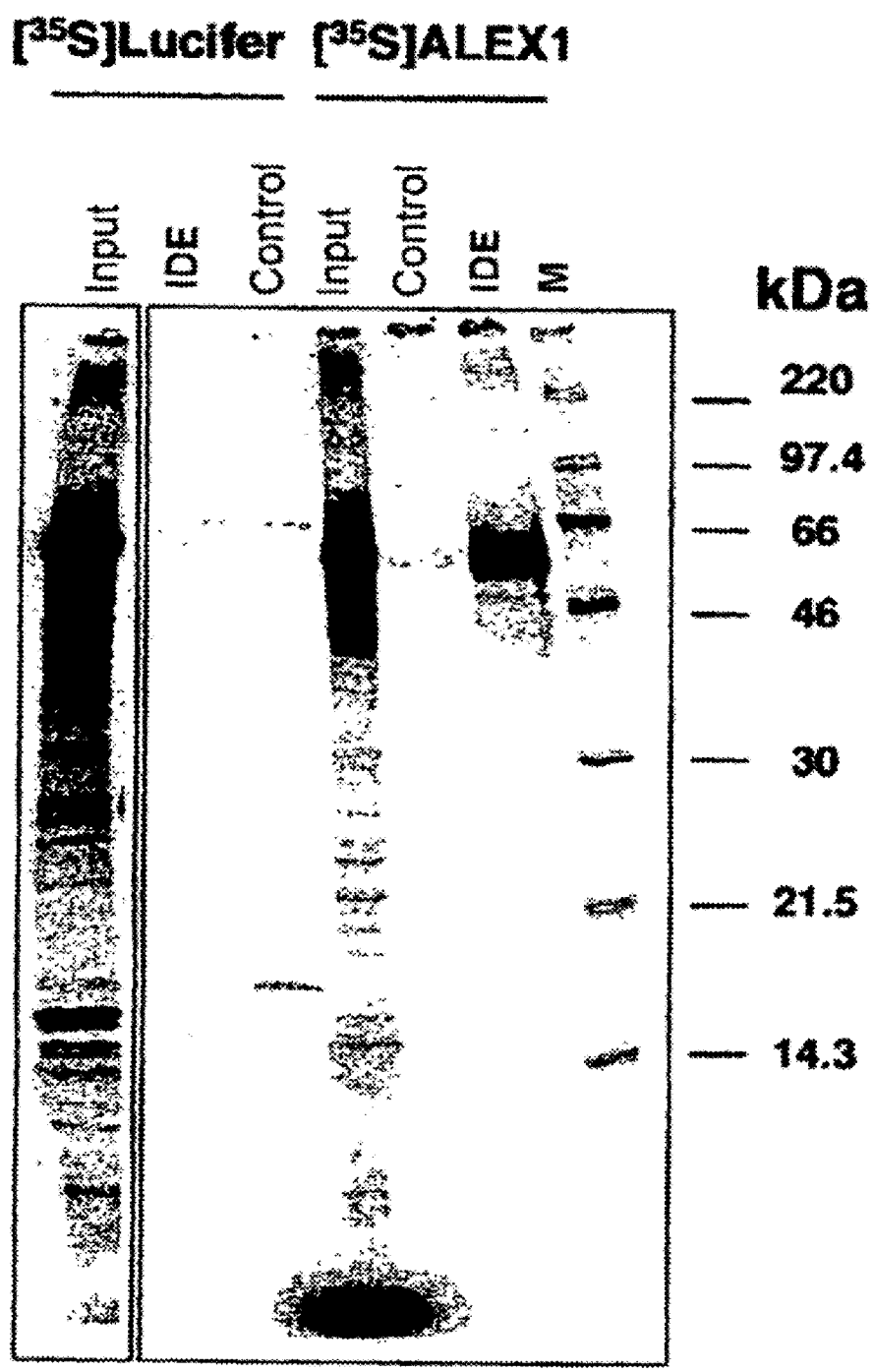
FIG. 1 shows in vitro interaction of ALEX1 with IDE.

The interaction of the both proteins was examined as above, ALEX1 bound to the IDE-beads but not control beads (FIG. 1). The IDE-beads were unable to adsorb $^{35}$S-labeled luciferase as the negative control, demonstrating the specificity of the observed binding.

EXAMPLE 3

Genomic Structure of ALEX1 Gene BLASTN analysis against GenBank and EMBL databases revealed that the clone U61B11 derived from the human chromosome X (GenBank Accession No. Z73913), sequenced by the Sanger Center, contains the sequence of the ALEX1 gene. Therefore, the inventors used this genomic sequence to determine the exon/intron organization of ALEX1 gene. As a result, it was revealed that the ALEX1 gene comprises 4.2 kb in length and is composed of four exons, ranging in size from 54 to 1892 nucleotides, with the coding region residing entirely in a single exon (exon 4). All exon-intron junctions conform to the consensus sequence for splice donor/acceptor sites (gt/ag).

EXAMPLE 4

Homology Search of Human ALEX1 Protein with Other Proteins

A homology search of public databases using the BLASTP program revealed that the full-length ALEX1 protein shares highest homology to previously uncharacterized ORF KIAA0512 of 632 amino acids. The homology region is present in the C-terminal parts of the both amino acid sequences with 51% identity and, when substitutions of similar amino acids were taken into account, there was a 72% homology over the 234 amino acids region (FIGS. 2 to 3). ALEX1 and KIAA0512 proteins have also almost identical N-terminal amino acid sequence (amino acid position 1 to 25) predicted to target these proteins to the endoplasmic reticulum (ER) membrane through this region. Similarly with ALEX1, the C-terminus of KIAA0512 contains microbodies targeting signal.

Although weaker than KIAA0512, ALEX1 shares homology to another uncharacterized ORF KIAA0443 (31% identity and, when substitutions of similar amino acids were taken into account, there was 55% homology over the 225 amino acids region) (FIGS. 2 to 3).

ALEX1 sequence was analyzed also by PSI-BLAST program. The PSI-BLAST method significantly increases the database-search sensitivity by incorporating information embedded in a multiple sequence alignment into a position-dependent weight matrix, which is employed as the query for iterating the search (Altshul, S. F. et al. (1997) Nucleic Acids Res. 25, 3389-3402). This allows the detection even of very low sequence homologies at a statistically significant level. Second iteration with E-value of 0.01 actually revealed that ALEX1 exhibits significant homologies to members of the Arm repeat family. In this search, ALEX1 showed the highest homology to importin α and yeast vacuolar protein 8 (Vac8p). Lower homology is shared with armadillo, β-catenin, and plakoglobin. The homology region is confined to the two Arm repeat regions present in ALEX1 protein.

BLASTN searches of dbEST database with the ALEX1 cDNA sequence as a query identified a number of highly homologous ESTs. These contained ESTs corresponding to the above-mentioned KIAA0512, KIAA0443 and an additional previously unknown cDNA. When several representative ESTs for this unknown cDNA were screened trough the dbTHC database at NCBI, the contig sequence of 2,036 nucleotides composed of 44 ESTs was identified (THC257925). A conceptual translation product of the THC257925 is 342 amino-acid protein with strong homology to ALEX1, KIAA0512 and the C-terminal half of KIAA0443 (FIGS. 2 to 3). This novel protein shares 55% identity and, when substitutions of similar amino acids were taken into account, there was 74% homology over the region of 259 amino acids with ALEX1 protein. Pfam algorithm detects in this amino acid sequence one Arm motif sequence, which corresponds to the first Arm motif in ALEX1.

No protein with less than six Arm repeats has been described so far among the known proteins of Arm family, and the classical members of the arm-family proteins including catenins and importins contain six or more Arm repeats. Thus, ALEX1 and its homologues do not represent true members of Arm repeat family proteins and constitute rather a new family, which the inventors name as ALEX family. Therefore, KIAA0512 and the novel ORF THC257925 are named as "ALEX2" and "ALEX3", correspondingly.

EXAMPLE 5

Determination of Chromosomal Location of ALEX Genes

The search of the UniGene collection at NCBI established that the 3' region of ALEX1 corresponds to cluster Hs.9728. This cluster is linked to the chromosomal marker sequence stSG9550 (DXS990-DXS1059). Similarly, the cDNA sequences of ALEX2 (KIAA0512) and ALEX3 (THC257925) match to the clusters Hs.48924 and Hs. 172788, respectively, linked to stSG22124 and stSG13135 that reside at the same interval DXS990-DXS1059. The DXS990-DXS1059 interval is mapped to band q21.33-q22.2 on the long arm of human chromosome X (Xq21.33-q22.2). BLASTN analysis further revealed that a clone 769N13 from human chromosome Xq22.1-23 region sequenced at the Sanger Center comprises the sequence of KIAA0443. Thus, all described ALEX family genes including ALEX1 to 3 and KIAA0443 are shown to locate in the same region on human chromosome X.

EXAMPLE 6

Analysis of ALEX1 and ALEX2 Gene Expression in Human Normal and Cancer Tissues

To investigate the gene expression of ALEX1 and ALEX2 in various human tissues, Northern blots prepared from poly (A)$^+$ RNA purified from a variety of human tissues were hybridized with the probes derived from the region of least homology between the two ALEXs.

Human Multiple Tissue Northern Blots containing 2 μg each of poly(A)+ RNA from various tissues and ExpressHyb hybridization solution were purchased from Clontech. Hybridization was conducted with labeled probe at 1×10$^6$ cpm/ml for 1 h at 68° C. The filters were washed with a final stringency of 0.1×SSC, 0.1% SDS at 50° C. for 40 min and exposed to Hyperfilm using intensifying screens at −80° C. The probes used were generated by PCR, purified through electrophoresis, and $^{32}$P-labeled as described above. The 227-bp ALEX1 probe was generated using primers F2/R2. The 328-bp ALEX2 probe was prepared with primers F4/R4.

As can be seen in FIG. 4, when ALEX1 probe was used, a clear single band corresponding to a transcript of about 2.2-kb was detected in the majority of the tissues. The size of the transcript indicates that the cloned cDNA represents the full-length ALEX1 mRNA. When the blots were hybridized with a probe specific for ALEX2, a transcript of about 2.7-kb was detected in most tissues. An additional transcript of 1.4 kb is prominently present in the skeletal muscle, testis, and placenta, and weak band of about 7 kb is seen in the brain. The analysis reveals that ALEX1 and ALEX2 have remarkably similar distribution of expression. Both mRNA were higher in ovary, heart, testis, prostate, brain, spleen, and colon. The transcripts were only barely detectable in liver and thymus. The expression of both mRNA in peripheral blood leukocytes was below the limits of detection. Even highly sensitive RT-PCR failed to detect ALEX1 and ALEX2 transcripts in leukocytes (data not shown).

Next, the expression of ALEX1 and ALEX2 in various human tumors was analyzed by RT-PCR. cDNA prepared from five normal tissues corresponding to respective tumors were used as positive controls. PCR analysis of the expression of ALEX1 and ALEX2 in human normal and cancer tissues was performed with Human I, Human II, and Human Tumor Multiple Tissue cDNA panels from Clontech. Primer combinations were F3/R2 for ALEX1 and F5/R5 for ALEX2. As shown in FIG. 5, no expression of ALEX1 and ALEX2 mRNA was detected in two lung carcinoma samples, in a prostatic adenocarcinoma sample, and in a colon adenocarcinoma sample. In addition, ALEX2 transcripts were not detectable in pancreas and ovarian carcinoma samples, while ALEX1 expression was significantly reduced in these samples as compared to the corresponding normal tissues. cDNA used in these experiments were prepared from tumor tissues that have been explanted and propagated as xenografts in nude mice.

To eliminate the possibility of changes of cell characteristics during xenograft maintenance, the inventors utilized the blot containing mRNA isolated from tumor ovaries and corresponding normal tissues of ovaries from four different donors to investigate the expression of ALEX1. Northern Territory Ovarian Tumor Blot containing 20 μg each of RNA isolated from human normal tissues and ovarian cancer tissues excised at the same operational site was obtained from Invitrogen. Northern hybridization was performed as described above. As shown in FIG. 6, ALEX1 mRNA is expressed in the normal part but undetectable in the tumor part of the ovaries from all four donors.

EXAMPLE 7

Investigation of Expression Pattern of ALEX1 and ALEX2 in Various Human Tumor-Derived Cell Lines Using RT-PCR, the present inventors examined ALEX1 and ALEX2 expression in various human tumor-derived cell lines. Namely, 2 μg of total RNA was reverse-transcribed using the Superscript II first-strand cDNA synthesis kit (Gibco BRL) with oligo(dT) primers according to the manufacturer's specifications. Obtained cDNA was subjected to PCR amplification using primers described above. As shown in FIG. 7, four normal tissues and two normal human diploid fibroblast cell lines were included as positive controls. Both transcripts are expressed in the glioblastoma-derived cell line A172 and the osteosarcoma-derived cell line TE-85. Low levels of ALEX1 and ALEX2 expression were found in the osteosarcoma-derived cell line U-2OS. However, no signal was detected in the immortal endothelial cell line t-HUE2, the cervix adenocarcinoma cell line HeLa, the lung carcinoma cell line A549, the non-small cell lung carcinoma cell line ABC-1, the cervical adenocarcinoma cell line C-33, and cytomegalovirus-transformed embryo lung fibroblast cell line CMV-Mj-HEL-1. The present inventors also examined ALEX1 and ALEX2 expression in four additional cell lines. These four cell lines were the normal human mammary gland epithelial cell line HBL-100, the breast adenocarcinoma cell line MDA-MB-468, and the neuroblastoma cell lines SH-SY5Y and IMR-32. ALEX1 and ALEX2 mRNA was detected in HBL-100 and both neuroblastoma cell lines but not in MDA-MB-468 (data not shown). Thus, it was shown that ALEX1 and ALEX2 are expressed in human sarcoma, glioblastoma, and neuroblastoma-derived cell lines but are not detectable in cell lines derived from human carcinomas of epithelial origin.

EXAMPLE 8

ALEX1 is Developmentally Regulated

Next the present inventors analyzed expression of ALEX1 mRNA at different stages of mouse embryo development. Based on the sequence available from mouse EST database, the inventors designed a probe for isolating the mouse homologous gene of ALEX1. As seen in FIG. 8, mouse ALEX1 transcript has a size of about 2.3-kb, practically identical to human ALEX1. Low levels of ALEX1 expression are already detectable in 7 day-old mouse embryo and the levels markedly elevated between day 7 and 11.

EXAMPLE 9

Yeast Two-Hybrid Screen for ALEX1-Interacting Proteins

The yeast two-hybrid method was used to identify proteins that interact with the ALEX1. Full-length ALEX1 was linked to Gal4-DB (DNA-binding domain of Gal4) in frame, and inserted into pODB-80 vector. The resulting plasmid was used as a bait to perform two-hybrid screening as Example 1. As a result of screening human brain cDNA library using full-length ALEX1 cDNA as the bait, three independent clones corresponding to overlapping fragments of JNK interacting protein-1 (JIP-1) have been identified. These represented amino acid numbers 160 to 711, 199 to 711, and 258 to 711 of human JIP-1. JIP-1 was characterized initially as a JNK-interacting protein and inhibitor of JNK signaling, by virtue of its ability to prevent nuclear translocation of JNK (Dickens, M. et al. (1997) Science 277, 693-696). To identify the binding site of ALEX1 on JIP-1, various fragments of JIP-1 were prepared and used in the yeast two-hybrid assay. As shown in FIG. 9, the results indicate that the region of amino acid numbers 374 to 479 of JIP-1 is mainly involved in ALEX1 binding. However, the residues N-terminal to amino acid number 374 and C-terminal to amino acid number 479 might be necessary for more rigid binding because a fragment comprising amino acid numbers 262 to 589 conferred faster growth of yeast cells as compared to that for amino acid numbers 374 to 711 (FIG. 9).

EXAMPLE 10

Effect of ALEX1 Overexpression on c-Jun-Dependent Transcriptional Activation

Because ALEX1 binds to JIP-1 in the yeast two-hybrid screen, the effects of forced expression of ALEX1 in cells lacking ALEX1 expression on JNK signaling pathway were investigated. Activated JNK phosphorylates transcriptional factor c-Jun whereby increasing its transcription activating ability. Therefore, for the experiments the human cervical carcinoma cell line HeLa S3 which does not express ALEX1 was used.

Gal4-c-Jun fusion protein was used as c-Jun, and its transcription activating ability was measured in co-transfection assays with the reporter plasmid pG5-Luc. This pG5-Luc contains five GAL4 sites cloned upstream of a minimal promoter element and the firefly luciferase gene. The plasmid pRL-TK having *Renilla* luciferase gene under the control of thymidine kinase gene promoter was co-transfected to provide an internal control. These plasmids were transfected into HeLa cells with GenePORTER transfection reagent (Gene Therapy Systems) in 12-well dishes. After transfection, cells were cultured in 0.5% FBS and reporter activities were analyzed after 42 h.

The MEKK1 protein, a known JNK activator, increased the expression of the c-Jun-dependent luciferase reporter gene by about 30-fold (FIG. 10), indicating activation of the Gal4-cJun fusion protein. The pFC-dbd plasmid (Gal4), which comprises the Gal4 DNA binding domain only and no activation domain, could not be activated by overexpression of the MEKK1 demonstrating the specificity of the assay. Forced expression of the ALEX1 significantly inhibited MEKK1-induced c-Jun-dependent transcription activating ability with the inhibition displaying a dose-dependent manner (FIG. 10).

EXAMPLE 11

Interaction Between ALEX1 and Presenilin-1 (PS1)

Interaction between ALEX1 and presenilin-1 (PS1) was investigated by pull-down assay. The large loop region of PS1 protruding into the cytoplasm reported to be the binding site with delta-catenin (PS1-CL: amino acid numbers 263-407 of PS-1 according to accession number L76517), and the N-terminal region (PS1-N: amino acid numbers 1-81 of PS-1 according to accession number L76517) as a negative control respectively were cloned into pGEX-5X-1 by PCR method, and were expressed in *E. coli* as GST fusion proteins. GST or GST fusion proteins, GST-PS1-CL ($263^{rd}$ to $407^{th}$ amino acids) and GST-PS1-N ($1^{st}$ to $81^{st}$ amino acids), were immobilized onto glutathione-Sepharose beads by incubating 80 µg of the proteins with 20 µl of the beads for 16 hr at 4° C. in immobilization buffer (20 mM Tris/Cl, pH 7.2 at 25° C., 140 mM NaCl, 1 mM EDTA, 0.1% Tween-20 and Complete™ Protease Inhibitor, Boehringer Mannheim). The mixture was centrifuged, unbound protein was discarded, and the beads were resuspended in 500 µl of binding buffer (20 mM Tris/Cl, pH 7.2 at 25° C., 140 mM NaCl, 0.1% Tween-20, 0.1 mM DTT, 4 mg/ml BSA and Complete™ Protease Inhibitor). In vitro-translated, [$^{35}$S]methionine-labeled (Promega TNT reticulocyte lysate system) ALEX1 was added to the mixture and incubated for 2.5 h at 4° C. to form complexes. Instead of ALEX1, luciferase as a negative control, and delta-catenin (615-1225) and delta-catenin (826-1225) as positive controls were used for same experiments. The beads were washed five times in wash buffer (20 mM Tris/Cl, pH 7.2 at 25° C., 140 mM NaCl, 0.1% Tween-20 and Complete™ Protease Inhibitor), resuspended in 40 µl of 2×SSC sample buffer and incubated at 90° C. A half of the eluted protein was resolved by SDS-PAGE (4-20%) and visualized by BAS2000.

As a result, bands were confirmed by coprecipitation of the labeled protein by GST-PS1-CL, only in 2 types of delta-catenin fragments and in ALEX1. These bands were not confirmed by GST or GST-PS1-N. Also for the negative control luciferase, bands were not confirmed at all.

EXAMPLE 12

Search of ALEX1 Binding Proteins by the Yeast Two-Hybrid Method

Since many false positive clones were obtained as a result of preliminary examination of yeast two-hybrid method using full-length ALEX1 as a bait, further examinations were made. It was elucidated that a large reduction in the number of false positive clones is possible by using as a bait, ALEX1 in which the transmembrane domain (amino acid numbers 1 to 27) existing at the N-terminal is removed. Therefore, after transforming yeast PJ69-2A with an expression vector in which delta (1-27) ALEX1 is linked to Gal4-DBD, human brain-derived cDNA library that is cloned onto a pACT2 vector (Human Brain Matchmaker cDNA Library: Clontech) was directly transfected, and then selection of nutritional demand indicated below was performed. As a result of screening a total of 2,100,000 clones, 476 clones grew under -His conditions, and furthermore approximately 40% of these were able to grow under -His/-Ade conditions. Further selection was continued, and ultimately 180 clones were selected under -His/-Ade/-Leu/-Trp conditions. Next, by rescuing library plasmids from these positive colonies to *E. coli*, and collecting them upon purification, nucleotide sequence determination on a total of 155 clones were performed. As a result, it was elucidated that approximately 10% of the colonies simultaneously carried two different library plasmids, and in such cases, the possibility that one of them was a false positive was considered. Therefore, for the purpose of further eliminating false positive clones, co-transfection with Gal4-DBD-delta (1-27) ALEX1 or Gal4-DBD that does not contain the bait into yeast PJ69-2A was further performed on all 155 clones obtained, and then clones capable of bait-dependent growth under -His/-Leu/-Trp conditions were selected. From this assay, approximately 20% of the clones could be eliminated as being false positive. Next, after transforming yeast Y187 strain with the same combination of plasmids, β-gal assay was performed. Several colonies showed negative β-gal activity. The following lists those that passed all of the above-mentioned tests, and in addition that were included in two or more independent clones, and summarizes their expected functions.

p0071 (plakophilin-4): Arm repeat-containing presenilin binding protein
GenBank Ac. No. X81889; *H. sapiens* mRNA for p0071 protein, GenBank Ac. No. NM_003628; *Homo sapiens* plakophilin 4 (PKP4), mRNA
SART-1: human squamous cell carcinoma antigen, expressed in growing cells only GenBank Ac. No. AB006198; *Homo sapiens* mRNA for SART-1, GenBank Ac. No. Y14314; *Homo sapiens* mRNA for IgE autoantigen MSP58: nucleoprotein, interacting to the growth-related nucleoprotein p120, expressed in growing cells only GenBank Ac. No. AF015308; *Homo sapiens* nucleolar protein (MSP58) mRNA, GenBank Ac. No. AF068007; *Homo sapiens* cell cycle-regulated factor p78 mRNA ATRX: murine colon adenocarcinoma antigen, cell cycle-dependently phosphorylated, a helicase/ATPase member of the SNF2 family GenBank Ac. No. U72938; *Homo sapiens* putative DNA dependent ATPase and helicase (ATRX) mRNA, alternatively spliced product 3, GenBank Ac. No. NM_000489; *Homo sapiens* alpha thalassemia/mental retardation syndrome X-linked (RAD54 (*S. cerevisiae*) homolog) (ATRX), mRNA CSA2 (RED protein): chondrosarcoma-associated protein, distributed in nuclei as dots, transcription-related function?

GenBank Ac. No. AF182645; *Homo sapiens* chondrosarcoma-associated protein 2 (CSA2) mRNA p68: RNA helicase/ATPase GenBank Ac. No. X52104; Human mRNA for p68 protein, GenBank Ac. No. NM_004396; *Homo sapiens* DEAD/H (Asp-Glu-Ala-Asp/His) box polypeptide 5 (RNA helicase, 68 kD) (DDX5), mRNA OS-9: amplified in human sarcoma, containing nuclear localization signal GenBank Ac. No. NM_006812; *Homo sapiens* amplified in osteosarcoma (OS-9), mRNA ZNF189: $C_2H_2$ Zinc Finger protein GenBank Ac. No. AF025770; *Homo sapiens* $C_2H_2$ zinc finger protein (ZNF189) mRNA KIAA1221: $C_2H_2$ Zinc Finger protein GenBank Ac. No. AB033047; *Homo sapiens* mRNA for KIAA1221 protein, partial cds α-Actinin4: involved in actin polymerization, cell motility, and cancer infiltration GenBank Ac. No. NM_004924; *Homo sapiens* actinin, alpha 4 (ACTN4), mRNA ZIP kinase GenBank Ac. No. AB022341; *Homo sapiens* mRNA for ZIP kinase ALEX1: homodimer formation

EXAMPLE 13

Examination of Intracellular (COS7 Cell) Localization Using ALEX1 with GFP Added to the N or C-Terminal End When a fusion protein in which ALEX1 was added to the C-terminal (N-EGFP-ALEX1-C) or to the N-terminal (N-ALEX1-EGFP-C) of EGFP was expressed in COS7 cells, and the intracellular localization was examined using a fluorescence microscope, it was confirmed that N-EGFP-ALEX1-C was distributed as spots within the nucleus (thought to be nucleoli), and in contrast, N-ALEX1-EGFP-C was observed to be eliminated from the nucleus and localized in the cytoplasm. This result was thought to be due to masking of the transmembrane domain existing near the N-terminal of ALEX1 in N-EGFP-ALEX1-C by added GFP. Therefore, the possibility of regulation of intracellular localization mediated by blocking or enzymatic cleavage of the transmembrane domain of ALEX1 was suggested.

INDUSTRIAL APPLICABILITY

This invention provides a novel armadillo repeat-containing protein ALEX1, and its gene. Expression of ALEX1 protein is significantly decreased in epithelial cancer. ALEX1 is also expected to be involved in Alzheimer's disease. Accordingly, by detecting the expression level of ALEX1, it is possible to test for cancer and Alzheimer's disease. In addition, it is possible to develop new pharmaceutical agents for preventing or treating these diseases by screening for drugs that regulate the expression or activity of ALEX1.

The invention claimed is:

1. An isolated protein comprising an amino acid sequence encoded by the nucleotide sequence of SEQ ID NO:1 or 2.

2. A fusion protein comprising the protein of claim 1 fused to one or more other proteins or peptides.

3. An isolated protein comprising the amino acid sequence of SEQ ID NO:3.

4. An isolated protein comprising an armadillo repeat structure encoded by a nucleotide sequence selected from the group consisting of:
   (a) a nucleotide sequence encoding a protein comprising the amino acid sequence of SEQ ID NO:3;
   (b) a nucleotide sequence comprising the coding region of the nucleotide sequence of SEQ ID NO:1 or 2; and
   (c) a nucleotide sequence encoding a protein in which 10 or less amino acids of the amino acid sequence of SEQ ID NO:3 have been substituted, deleted, inserted, and/or added wherein the encoded protein retains the biological activity of the protein comprising the amino acid sequence of SEQ ID NO: 3.

5. An isolated protein that binds to a protein selected from the group consisting of insulin-degrading enzyme (IDE), presenilin-1 (PS-1), p0071 (plakophilin-4), SART-1, MSP58, ATRX, CSA2 (RED protein), p68 (RNA helicase/ATPase), OS-9, ZNF189, KIAA1221, α-Actinin4, and ZIP kinase, wherein the isolated protein is encoded by a nucleotide sequence selected from the group consisting of:
   (a) a nucleotide sequence encoding a protein comprising the amino acid sequence of SEQ ID NO:3;
   (b) a nucleotide sequence comprising the coding region of the nucleotide sequence of SEQ ID NO:1 or 2; and
   (c) a nucleotide sequence encoding a protein in which 10 or less amino acids of the amino acid sequence of SEQ ID NO:3 have been substituted, deleted, inserted, and/or added wherein the encoded protein retains the biological activity of the protein comprising the amino acid sequence of SEQ ID NO: 3.

6. An isolated protein that binds to JNK interacting protein 1 (JIP-1), wherein the protein is encoded by a nucleotide sequence selected from the group consisting of:
   (a) a nucleotide sequence encoding a protein comprising the amino acid sequence of SEQ ID NO:3;
   (b) a nucleotide sequence comprising the coding region of the nucleotide sequence of SEQ ID NO:1 or 2; and
   (c) a nucleotide sequence encoding a protein in which 10 or less amino acids of the amino acid sequence of SEQ ID NO:3 have been substituted, deleted, inserted, and/or added wherein the encoded protein retains the biological activity of the protein comprising the amino acid sequence of SEQ ID NO: 3.

7. The isolated protein of claim 6 that inhibits c-Jun-dependent transcription.

* * * * *